(12) United States Patent
Buturovic et al.

(10) Patent No.: US 8,473,217 B1
(45) Date of Patent: Jun. 25, 2013

(54) METHOD AND SYSTEM FOR STANDARDIZATION OF MICROARRAY DATA

(75) Inventors: Ljubomir J. Buturovic, East Palo Alto, CA (US); Glenda G. Anderson, San Jose, CA (US); Jorge Moraleda, Menlo Park, CA (US)

(73) Assignee: Pathwork Diagnostics, Inc., Redwood City, CA (US)

( * ) Notice: Subject to any disclaimer, the term of this patent is extended or adjusted under 35 U.S.C. 154(b) by 934 days.

(21) Appl. No.: 12/378,187

(22) Filed: Feb. 10, 2009

Related U.S. Application Data

(63) Continuation of application No. 11/982,064, filed on Oct. 31, 2007, now abandoned.

(51) Int. Cl.
 *G01N 33/48* (2006.01)
(52) U.S. Cl.
 USPC .......................................................... 702/19
(58) Field of Classification Search
 None
 See application file for complete search history.

(56) References Cited

U.S. PATENT DOCUMENTS

2003/0182066 A1 9/2003 Konishi

OTHER PUBLICATIONS

Affymetrix Power Tools: Affymetrix Power Tools (APT)—Release 1.14.3. [online]. [retrieved on Nov. 9, 2011]. Retrieved from the Internet: <URL: http://www.affymetrix.com/support/developer/powertools/changelog/index.html>.
Affymetrix Power Tools: Manual: apt-probeset-summarize (1.14.3). [online]. [retrieved on Nov. 9. 2011] Retrieved from the Internet: <URL: http://www.affymetrix.com/support/developer/powertools/changelog/apt-probeset-summarize.html>.
Affymetrix Power Tools: Change Log, Jan. 2, 2006 through Nov. 1, 2011. [online] [retrieved on Nov. 8. 2011] Retrieved from the Internet: <URL: http://www.affymetrix.com/support/developer/powertools/changelog/CHANGE.html>.
Bolstad et al., 2003, "A Comparison of Normalization Methods for High Density Oligonucleotide Array Data Based on Variance and Bias," Bioinformatics 19, 185-193.
Draghici, 2003, *Data Analysis for DNA Microarrays*, Chapman & Hall, Boca Raton, pp. 33-58 and 309-339.
Gautier et al., 2004, "Affy-analysis of Affymetrix GeneChip Data at the Probe Level," Bioinformatics 20, 307-315.
Irizarry et al., 2003, "Exploration, Normalization, and Summaries of High Density Oligonucleotide Array Probe Level Data," Biostatistics 4, 249-264.
Li et al., 2001, "Model-based Analysis of Oligonucleotide Arrays: Model Validation, Design Issues and Standard Error Application," Genome Biology 2, 0032.1-0032.11.
Ma et al., Apr. 2006, "Molecular Classification of Human Cancers Using a 92-Gene Real-Time Quantitative Polymerase Chain Reaction Assay," Arch Pathol Lab Med 130, 465-473.
Martin et al., 2004, "Rank Difference Analysis of Microarrays (RDAM), a Novel Approach to Statistical Analysis of Microarray Expression Profiling Data," BMC Bioinformatics 5, 1-48.
Saviozzi et al., 2003, "Microarray Probe Expression Measures, Data Normalization and Statistical Validation," Comp Funct Genom 4, 442-446.
Wang et al., 2005, "A Study of Inter-lab and Inter-platform Agreement of DNA Microarray Data," BMC Genomics 6, 1-9.

*Primary Examiner* — Pablo S Whaley
(74) *Attorney, Agent, or Firm* — Morgan, Lewis & Bockius LLP

(57) ABSTRACT

The present invention relates to a method and system for standardizing a test microarray dataset. The method requires obtaining a test microarray dataset comprising abundance values for a first plurality of cellular constituents, providing a standardization data structure associated with values of central tendency and identifies, and applying the standardization data structure to the test microarray dataset using a mathematical transformation in order to produce a standardized test microarray dataset.
This change has been made for purposes of compact prosecution and to better embrace the allowable subject matter.

14 Claims, 13 Drawing Sheets

| | | |
|---|---|---|
| 120-1 → Identifier 1 | Measure of central tendency 1 | ← 140-1 |
| 120-2 → Identifier 2 | Measure of central tendency 2 | ← 140-2 |
| 120-3 → Identifier 3 | Measure of central tendency 3 | ← 140-3 |
| 120-4 → Identifier 4 | Measure of central tendency 4 | ← 140-4 |
| 120-5 → Identifier 5 | Measure of central tendency 5 | ← 140-5 |
| ⋮ | ⋮ | |
| 120-P → Identifier P | Measure of central tendency P | ← 140-P |

METHOD AND SYSTEM FOR STANDARDIZATION OF MICROARRAY DATA

CROSS REFERENCE TO RELATED APPLICATIONS

This application is a continuation of application Ser. No. 11/982,064, filed on Oct. 31, 2007 now abandoned which is hereby incorporated by reference herein in its entirety.

1 FIELD OF THE INVENTION

The present invention relates to systems and methods for the conversion of microarray expression measurements from different sources are converted to mutually comparable values.

2 BACKGROUND OF THE INVENTION

Poor reproducibility of microarray expression measurements under varying experimental conditions has been a significant impediment to widespread adoption into clinical practice. Variation among expression values has been classified as biologically interesting and obscuring. See, for example, Bolstad et al., 2003 Bioinformatics 19, 185-193, which is hereby incorporated by reference herein in its entirety. Previous research, Bolstad et al., 2003 Bioinformatics 19, 185-193, and Lyons-Weiler, 2003, Applied Bioinformatics: 2, 193-195, has identified the following sources of obscuring variation among microarray datasets conducted on replicate samples in multiple laboratories: (i) differences in sample preparation (for example, total RNA preparation, amplification and labeling), (ii) differences in the production and age of the arrays, and (iii) differences in the processing of the arrays (for example, time, temperature, drying and washing protocols, scanner differences).

The computational process by which the microarray expression measurements are converted to mutually comparable values is referred to as standardization. Initial efforts at microarray standardization involved dividing the log-expression values on a microarray by the mean expression of all genes across the microarray. This approach works well if the relation between cellular constituent abundance for a given gene (which is the quantity microarrays are designed to measure) and hybridization signal measured by the scanner is approximately linear across replicate samples. However, it has been established (Bolstad et al. 2003, Bioinformatics 19, 185-193, Moraleda et al., 2004, Proceedings of the American Society of Clinical Oncology annual meeting Vol. 23, each of which is hereby incorporated by reference herein) that in practice this relation is non-linear for common microarray designs and typical clinical specimens, saturating at higher levels of mRNA abundance. As a result, focus of the research has shifted toward non-linear transformations that compensate for this effect.

Earlier approaches have used the notion of housekeeping genes to effect the transformation. See, for example, Kohane et al., 2003 *Microarrays for Integrative Genomics* The MIT Press, 2003. This method makes the fundamental assumption that genes with similar levels of expression are affected in similar ways by the obscuring variations. This idea is the basis for leading methods of microarray standardization, including quantile normalization (Bolstad et al. 2003, Bioinformatics 19, 185-193, which is hereby incorporated by reference herein) and invariant set normalization (Li et al., 2003, *The Analysis of Gene Expression Data Methods and Software*, Springer, pp. 120-141, which is hereby incorporated by reference herein). Quantile normalization considers a set of arrays, and normalizes each against all others such that the quantiles of all arrays agree after the normalization. Invariant set normalizes a pair of arrays at a time such that the non-differentially expressed genes in the two arrays have similar ranks after the normalization.

Earlier standardization approaches that make use of housekeeping genes are further based on the fundamental assumption that there exist housekeeping genes, defined as genes participating in fundamental cell processes, which have a well-understood level of expression among a wide variety of cell types and conditions. Existence of housekeeping genes and their utility in microarray studies has been recognized previously. See, for example, Warrington et al., 2000, Physiol. Genomics 2, 143-147; and de Kok et al., 2005, Laboratory Investigation 85, 154-159, each of which is hereby incorporated by reference herein in its entirety.

Known approaches to standardization have proven to be useful in situations where the microarray data is from a single laboratory source. However, such standardization approaches have proven to be deficient when the microarray is from multiple different sources. In particular, known standardization approaches have proven to be deficient when attempts are made to standardize data from a laboratory source that was not used in the standardization learning set. Given the above background, what is needed in the art are improved systems and methods for standardizing test microarray datasets.

3 SUMMARY OF THE INVENTION

The present invention addresses the shortcomings in the prior art. In the present invention, a standardization data structure is constructed from microarray data from several different laboratories and from specimens from each of several different phenotypic characterizations, such as disease state and cell morphology. Each such laboratory may have, for example, (i) differences in sample preparation (e.g., total RNA preparation, amplification and labeling), (ii) differences in the production and age of the microarrays, and/or (iii) differences in the processing of the microarrays (e.g., time, temperature, drying and washing protocols, scanner differences). Advantageously, the standardization data structure is capable of standardizing microarray data from a laboratory that did not contribute cellular constituent abundance data to the standardization data structure.

One aspect of the present invention provides a method of standardizing a test microarray dataset comprising a first plurality of cellular constituents. The test microarray dataset further comprises an abundance value of each cellular constituent in the first plurality of cellular constituents. In the method, a standardization data structure is applied to an abundance value of each cellular constituent in the first plurality of cellular constituents, thereby computing a standardized test microarray dataset. The standardization data structure comprises a plurality of values of central tendency and, for each respective value of central tendency in the plurality of values of central tendency, an identifier. In some embodiments, there are at least 30 values of central tendency in the standardization data structure, one for each of at least 30 different cellular constituents. In some embodiments, there are at least 50 values of central tendency in the standardization data structure, one for each of at least 50 different cellular constituents. In some embodiments, there are at least 75 values of central tendency in the standardization data structure, one for each of at least 75 different cellular constituents. In some embodiments, there are at least 100 values of central tendency in the standardization data structure, one for each of at least 100 different cellular constituents. In some embodiments, there are at least 200 values of central tendency in the standardization data structure, one for each of at least 200 different cellular constituents. In some embodiments, there are at least 300 values of central tendency in the standardization data structure, one for each of at least 300 different cellular constituents.

Each value of central tendency in the plurality of values of central tendency is a measure of central tendency of cellular constituent abundance values in a plurality of training microarray datasets. In typical embodiments, the test microarray dataset is not included in the plurality of training microarray datasets. In some embodiments, the test microarray dataset is included in the plurality of training microarray datasets. The standardized test microarray dataset is outputted to a user interface device, a monitor, a computer-readable storage medium, a computer-readable memory, or a local or remote computer system. Alternatively or additionally, the standardized test microarray dataset is displayed. In preferred embodiments, each training microarray dataset in the plurality of training microarray datasets is from a different microarray experiment. In preferred embodiments, a microarray experiment is the measurement of a plurality of cellular constituent abundance values from a single microarray.

In some embodiments each training microarray dataset in the plurality of training microarray datasets is for a specimen (e.g., biological specimen) in a plurality of specimens. In some embodiments, each training microarray dataset in the plurality of training microarray datasets comprises abundance values for a second plurality of cellular constituents.

In some embodiments, the plurality of training microarray datasets comprises microarray datasets for at least five different phenotypic characterizations, at least ten different phenotypic characterizations, at least fifty different phenotypic characterizations, or at least five hundred different phenotypic characterizations. In some embodiments, a phenotypic characterization in the different phenotypic characterizations represented by the plurality of training microarray datasets is a tissue type, an organ type, a cell type, a cell morphology, or a disease state. In some embodiments, a phenotypic characterization in the different phenotypic characterizations represented by the plurality of training microarray datasets is an abnormal phenotypic characterization (e.g., abnormal state in a tissue or organ, an abnormal cell type, an abnormal cell morphology, or a disease state). In some embodiments, there are at least ten different microarray datasets, at least 50 different microarray datasets, at least 100 different microarray datasets, or at least 500 different microarray datasets in the plurality of phenotypic characterizations for each phenotypic characterization represented by the plurality of training microarray datasets.

In some embodiments, a cellular constituent in the first plurality of cellular constituents is a gene, a protein, a peptide, a proteoglycan, a glycoprotein, a lipoprotein, a carbohydrate, a lipid, a nucleic acid, an mRNA, a cDNA, an oligonucleotide, a microRNA, a tRNA, or a protein with a selected modification (e.g., phosphorylation). In some embodiments, a cellular constituent in the second plurality of cellular constituents is a gene, a protein, a peptide, a proteoglycan, a glycoprotein, a lipoprotein, a carbohydrate, a lipid, a nucleic acid, an mRNA, a cDNA, an oligonucleotide, a microRNA, a tRNA, or a protein with a selected modification (e.g., phosphorylation).

In some embodiments, each cellular constituent in the first plurality of cellular constituents is a different gene. In some embodiments, each cellular constituent in the second plurality of cellular constituents is a different gene.

In some embodiments, each cellular constituent in the first plurality of cellular constituents is a different protein. In some embodiments, each cellular constituent in the second plurality of cellular constituents is a different protein.

In some embodiments, each cellular constituent in the first plurality of cellular constituents is a different peptide. In some embodiments, each cellular constituent in the second plurality of cellular constituents is a different peptide.

In some embodiments, each cellular constituent in the first plurality of cellular constituents is a different proteoglycan. In some embodiments, each cellular constituent in the second plurality of cellular constituents is a different proteoglycan.

In some embodiments, each cellular constituent in the first plurality of cellular constituents is a different glycoprotein. In some embodiments, each cellular constituent in the second plurality of cellular constituents is a different glycoprotein.

In some embodiments, each cellular constituent in the first plurality of cellular constituents is a different lipoprotein. In some embodiments, each cellular constituent in the second plurality of cellular constituents is a different lipoprotein.

In some embodiments, each cellular constituent in the first plurality of cellular constituents is a different carbohydrate. In some embodiments, each cellular constituent in the second plurality of cellular constituents is a different carbohydrate.

In some embodiments, each cellular constituent in the first plurality of cellular constituents is a different lipid. In some embodiments, each cellular constituent in the second plurality of cellular constituents is a different lipid.

In some embodiments, each cellular constituent in the first plurality of cellular constituents is a different mRNA. In some embodiments, each cellular constituent in the second plurality of cellular constituents is a different mRNA.

In some embodiments, each cellular constituent in the first plurality of cellular constituents is a different cDNA. In some embodiments, each cellular constituent in the second plurality of cellular constituents is a different cDNA.

In some embodiments, each cellular constituent in the first plurality of cellular constituents is a different oligonucleotide. In some embodiments, each cellular constituent in the second plurality of cellular constituents is a different oligonucleotide.

In some embodiments, each cellular constituent in the first plurality of cellular constituents is a different microRNA. In some embodiments, each cellular constituent in the second plurality of cellular constituents is a different microRNA.

In some embodiments, each cellular constituent in the first plurality of cellular constituents is a different tRNA. In some embodiments, each cellular constituent in the second plurality of cellular constituents is a different tRNA.

In some embodiments, each cellular constituent in the first plurality of cellular constituents is different protein with a selected modification. In some embodiments, each cellular constituent in the second plurality of cellular constituents is a different protein with a selected modification.

In some embodiments, each cellular constituent in the first plurality of cellular constituents is a different nucleic acid. In some embodiments, each cellular constituent in the second plurality of cellular constituents is a different nucleic acid.

In some embodiments, the test microarray dataset and/or a training microarray dataset is measured from a microarray comprising probes arranged with a density of 100 different probes per 1 $cm^2$ or higher or a density of at least 2,500 different probes per 1 $cm^2$. In some embodiments the test microarray dataset and/or a training microarray dataset is measured from a microarray wherein the microarray probes on the microarray consists of at least 10,000 different probes. In some embodiments, the test microarray dataset and/or a training microarray dataset is measured from an expression microarray, a comparative genomic hybridization microarray, an exon microarray, or a microRNA microarray.

In some embodiments, a value of central tendency in the plurality of values of central tendency is a geometric mean, an arithmetic mean, median or mode of a second plurality of cellular constituent abundance values in the plurality of training microarray datasets. In some embodiments, each cellular constituent abundance value in the second plurality of cellular constituent abundance values is the cellular constituent abundance of the same cellular constituent from a different training microarray dataset in the plurality of training microarray datasets and the identifier for the value of central tendency is an identity of the cellular constituent.

In some embodiments, each cellular constituent abundance value in the second plurality of cellular constituent abundance values is the cellular constituent abundance value for a cellular constituent from a different training microarray dataset in the plurality of training microarray datasets having the same cellular constituent abundance value ranking in the different training microarray dataset and the identifier for the value of central tendency is the cellular constituent abundance value ranking.

In some embodiments, the first plurality of cellular constituents is between 1,000 and $5 \times 10^6$ oligonucleotides, the first plurality of cellular constituents is between 1,000 and 50,000 mRNA, or the first plurality of cellular constituents is between 50 and 200,000 proteins. In some embodiments, the plurality of values of central tendency is between 25 and 50,000 values of central tendency. In some embodiments, the plurality of training microarray datasets is between 50 and 20,000 training microarray datasets. In some embodiments, the second plurality of cellular constituents is between 25 and 50,000 cellular constituents. In some embodiments, the second plurality of cellular constituents is a subset of the cellular constituents measured in the plurality of training microarray datasets.

In some embodiments, each respective value of central tendency in the plurality of values of central tendency is for a cellular constituent in the second plurality of cellular constituents and the method further comprises computing the plurality of values of central tendency before applying the standardization data structure to an abundance value for each cellular constituent in the plurality of cellular constituents. In this embodiment, each respective value of central tendency in the plurality of values of central tendency is a measure of central tendency (e.g., an arithmetic mean) of a respective collection of cellular constituent abundance values for a cellular constituent in the second plurality of cellular constituents. Further, each cellular constituent abundance value in the respective collection of cellular constituent abundance values is for the same cellular constituent from a different training microarray dataset in the plurality of training microarray datasets. In some such embodiments, the method further comprises identifying the second plurality of cellular constituents by the following method:

(i) standardizing, for each respective training microarray dataset in the plurality of training microarray datasets, the respective training microarray dataset by dividing each cellular constituent abundance value in the respective training microarray dataset by a measure of central tendency for all of the cellular constituent abundance values in the respective training microarray dataset;

(ii) dividing a third plurality of cellular constituents represented by the plurality of training microarray datasets into a plurality of abundance bins based on the measured abundance values for the third plurality of cellular constituents in the plurality of training microarray datasets, where each abundance bin represents an abundance value range exhibited by the third plurality of cellular constituents in the plurality of training microarray datasets;

(iii) computing a measure of variability for each respective cellular constituent in the third plurality of cellular constituents across the plurality of training microarray datasets;

(iv) designating, for each respective abundance bin in the plurality of abundance bins, a predetermined number of cellular constituents in the respective abundance bin having the lowest cellular constituent abundance variability in the plurality of training microarray datasets, relative to all other cellular constituents in the respective abundance bin, to be part of a candidate standardization data structure;

(v) calculating a training value for each respective cellular constituent in the candidate standardization data structure, where the training value for the respective cellular constituent is a measure of central tendency of an abundance of the respective cellular constituent across the plurality of training microarray datasets;

(vi) transforming each cellular constituent abundance value in a training microarray dataset in the third training microarray datasets using a kernel transformation based upon the training microarray dataset;

(vii) repeating the transforming step (vi) until cellular constituent abundance values in each training microarray dataset in the plurality of training microarray datasets have been transformed; and (viii) repeating steps (ii) through (vii) until a percent similarity between the identity of the cellular constituents in the candidate standardization data structure and the identity of the cellular constituents in a previous instance of the candidate standardization data structure is above a threshold value, where the cellular constituents in the candidate standardization data structure at a time when the percent similarity between the identity of the cellular constituents in the candidate standardization data structure and the identity of the cellular constituents in a previous instance of the candidate standardization data structure is above a threshold value is deemed to be the second plurality of cellular constituents.

In some embodiments, a first range of measured abundance values of cellular constituents in a first abundance bin in the plurality of abundance bins overlaps a second range of measured abundance values of cellular constituents in a second abundance bin in the plurality of abundance bins. In some embodiments, a first range of measured abundance values of cellular constituents in a first abundance bin in the plurality of abundance bins does not overlap a second range of measured abundance values of cellular constituents in a second abundance bin in the plurality of abundance bins.

In some embodiments, the threshold value is eighty percent, ninety percent, ninety-five percent or ninety-nine percent. In some embodiments, a percent similarity between the identity of the cellular constituents in the candidate standardization data structure and the identity of the cellular constituents in a previous instance of the candidate standardization data structure is deemed above a threshold value when there are less than one hundred cellular constituents in the candidate standardization data structure that are not in a previous instance of the candidate standardization data structure, less than fifty cellular constituents in the candidate standardization data structure that are not in a previous instance of the candidate standardization data structure, or less than five cellular constituents in the candidate standardization data structure that are not in a previous instance of the candidate standardization data structure. In some embodiments, a percent similarity between the identity of the cellular constituents in the candidate standardization data structure and the identity of the cellular constituents in a previous instance of the candidate standardization data structure is deemed above a threshold value when steps (ii) through (vii) have been repeated five or more times. In some embodiments, a percent similarity between the identity of the cellular constituents in the candidate standardization data structure and the identity of the cellular constituents in a previous instance of the candidate standardization data structure is deemed above a threshold value when steps (ii) through (vii) have been repeated one or more times.

In some embodiments, the measure of central tendency in step (i) is the median of cellular constituent abundance values in the respective training microarray dataset. In some embodiments, the plurality of abundance bins in step (ii) is between 3 and 15 abundance bins. In some embodiments, the measure of variability computed for each respective cellular constituent in step (iii) is based upon a coefficient of variation of cellular constituent abundance of the respective cellular constituent across the plurality of training microarray datasets. In some embodiments, the predetermined number in step (iv) is 5 or more cellular constituents, 10 or more cellular constituents, 40 or more cellular constituents, or 100 or more cellular constituents. In some embodiments, the measure of central tendency computed for a respective cellular constituent in step (v) is the arithmetic mean of the abundance values for the respective cellular constituent across the plurality of training microarray datasets.

In some embodiments, the kernel transformation transforms a cellular constituent abundance value x in the training microarray dataset to the cellular constituent abundance value y by the formula:

$$y = \frac{\sum_{j=0}^{m-1} w_j \cdot (t_j + s \cdot (x - h_j))}{\sum_{j=0}^{m-1} w_j}$$

where j is an index to a set of values M of cardinality m of central tendency in the standardization data structure having values within a threshold value w of x;

$t_j$ is a cellular constituent abundance value of central tendency, for a cellular constituent j, in the set of values M that is stored in the standardization data structure;

$h_j$ is a cellular constituent abundance value for the cellular constituent j in the training microarray dataset;

$w_j$ is $1 - \left|\frac{x - h_j}{w}\right|^p$;

w is the kernel function half-width;
p is the kernel function parameter; and
s is an average slope of the kernel function.
In some embodiments, $$s = \frac{t_{max} - t_{min}}{x_{max} - x_{min}}$$

where
$t_{max}$=the median value of a highest portion of the plurality of values of central tendency;

$t_{min}$=the median value of a lowest portion of the plurality of values of central tendency;

$x_{max}$=the median value of the cellular constituents in the training microarray dataset that are the same as the cellular constituents that form the highest portion of the plurality of values of central tendency;

$x_{min}$=the median value of the cellular constituents in the training microarray dataset that are the same as the cellular constituents that form the lowest portion of the plurality of values of central tendency.

In some embodiments, the highest portion of the plurality of values of central tendency is the highest q quantile of the plurality of values of central tendency and the lowest portion of the plurality of values of central tendency is the lowest q quantile of the plurality of values of central tendency, where the q quantile is expressed on the 0 to 1 scale (e.g., q=0.1).

In some embodiments, the standardization data structure is constructed before applying the standardization data structure to an abundance value for each cellular constituent in the first plurality of cellular constituents. In some such embodiments, each respective value of central tendency in the plurality of values of central tendency is an arithmetic mean of a respective collection of cellular constituent abundance values. In some such embodiments, a cellular constituent abundance of each cellular constituent in the respective collection of cellular constituent abundance values has the same cellular constituent abundance ranking in all of the training microarray datasets in the plurality of training microarray datasets. In some embodiments, a cellular constituent abundance value of a first cellular constituent and a cellular constituent abundance value of a second cellular constituent are used in a value of central tendency in the plurality of values of central tendency and an identity of the first cellular constituent is different than an identity of the second cellular constituent. In some embodiments, a cellular constituent abundance value of a first cellular constituent and a cellular constituent abundance value of a second cellular constituent are used in a value of central tendency in the plurality of values of central tendency and an identity of the first cellular constituent is the same as an identity of the second cellular constituent.

In some embodiments, each respective value of central tendency in the plurality of values of central tendency is an arithmetic mean of a respective collection of cellular constituent abundance values for a cellular constituent in the second plurality of cellular constituents, where each cellular constituent abundance value in the respective collection of cellular constituent abundance values is for the same cellular constituent from a different training microarray dataset in the plurality of training microarray datasets and where the standardization data structure is applied by to an abundance value x for a cellular constituent in the first plurality of cellular constituents in the test microarray dataset by transforming the value x to the cellular constituent abundance value y in a standardized test microarray dataset by the formula:

$$y = \frac{\sum_{j=0}^{m-1} w_j \cdot (t_j + s \cdot (x - h_j))}{\sum_{j=0}^{m-1} w_j}$$

where
j is an index to a set of values M of cardinality m of central tendency in the standardization data structure having values within a threshold value w of x;

$t_j$ is a value of central tendency, for a cellular constituent j, in the set M that is stored in the standardization data structure;

$h_j$ is a cellular constituent abundance value for the cellular constituent j in the first plurality of cellular constituents of the test microarray dataset;

$$w_j \text{ is } 1 - \left|\frac{x - h_j}{w}\right|^p;$$

w is the kernel function half-width;
p is the kernel function parameter; and
s is an average slope of the kernel function.
In some embodiments $$s = \frac{t_{max} - t_{min}}{x_{max} - x_{min}}$$

where $t_{max}$=the median value of a highest portion of the plurality of values of central tendency;

$t_{min}$=the median value of a lowest portion of the plurality of values of central tendency;

$x_{max}$=the median value of the cellular constituents in the first plurality of cellular constituents of the test microarray dataset that are the same as the cellular constituents that form the highest portion of the plurality of values of central tendency; and $x_{min}$=the median value of the cellular constituents in the first plurality of cellular constituents of the test microarray dataset that are the same as the cellular constituents that form the lowest portion of the plurality of values of central tendency.

In some embodiments, the highest portion of the plurality of values of central tendency is the highest q quantile of the plurality of values of central tendency and the lowest portion of the plurality of values of central tendency is the lowest q quantile of the plurality of values of central tendency, where q is between 0 and 1 (e.g., q=0.1).

In some embodiments, each respective value of central tendency in the plurality of values of central tendency is an arithmetic mean of a respective collection of cellular constituent abundance values. Furthermore, a cellular constituent abundance of each cellular constituent in the respective collection of cellular constituent abundance values has the same cellular constituent abundance ranking in all of the training microarray datasets in the plurality of training microarray datasets. In some such embodiments, the standardization data structure is applied to an abundance value x for a cellular constituent in the first plurality of cellular constituents in the test microarray dataset by transforming the value x to the cellular constituent abundance value y in the standardized test microarray dataset by the method comprising (i) determining a rank of the abundance value x for the cellular constituent in a ranking of the first plurality of cellular constituents in the test microarray dataset, and (ii) assigning the cellular constituent abundance value y in the standardized test microarray dataset the value of central tendency in the plurality of values of central tendency that has the same rank as the rank of the abundance value x for the cellular constituent in the ranking of the first plurality of cellular constituents.

In some embodiments, the test microarray dataset is received from a remote source over a wide area network and the standardized test microarray dataset is communicated to the remote source over the wide area network.

In some embodiments, the first plurality of cellular constituents is greater than a number of cellular constituents in a training microarray dataset in the plurality of training microarray datasets. In some embodiments, the first plurality of cellular constituents is equal to a number of cellular constituents in a training microarray dataset in the plurality of training microarray datasets. In some embodiments, the first plurality of cellular constituents is less than a number of cellular constituents in a training microarray dataset in the plurality of training microarray datasets.

Another aspect of the present invention provides a method of computing a standardization data structure for standardizing a test microarray dataset, where (i) the test microarray dataset comprises an abundance value for each cellular constituent in a first plurality of cellular constituents, (ii) the standardization data structure comprises a plurality of values of central tendency and, for each respective value of central tendency in the plurality of values of central tendency, an identifier, where the standardization data structure is computed from a plurality of training microarray datasets, (iii) the test microarray dataset is not included in the plurality of training microarray datasets; and (iv) each training microarray dataset in the plurality of training microarray datasets comprises abundance values for a second plurality of cellular constituents. The method in this aspect of the invention comprises computing the plurality of values of central tendency, where each respective value of central tendency in the plurality of values of central tendency is a measure of central tendency of a respective collection of cellular constituent abundance values for a cellular constituent in the second plurality of cellular constituents, and where each cellular constituent abundance value in the respective collection of cellular constituent abundance values is for the same cellular constituent from a different training microarray dataset in the plurality of training microarray datasets. An identifier is computed for each value of central tendency in the plurality of values of central tendency and the standardization data structure comprising the plurality of values of central tendency and the identifier for each value of central tendency in the plurality of values of central tendency is outputted to a user interface device, a monitor, a computer-readable storage medium, a computer-readable memory, or a local or remote computer system (or the standardization data structure is displayed).

Another aspect of the present invention provides computer-readable mediums, computer systems, and apparatus for performing any of the methods herein.

It should be noted that the phrase "comprises" and the phrase "comprises at least" are used interchangeably in this application, and that "comprises" and "comprises at least" are both open ended terms.

4 BRIEF DESCRIPTION OF THE DRAWINGS

FIG. 1C illustrates an exemplary standardization data structure in accordance with an embodiment of the present invention.

Figure 2A:
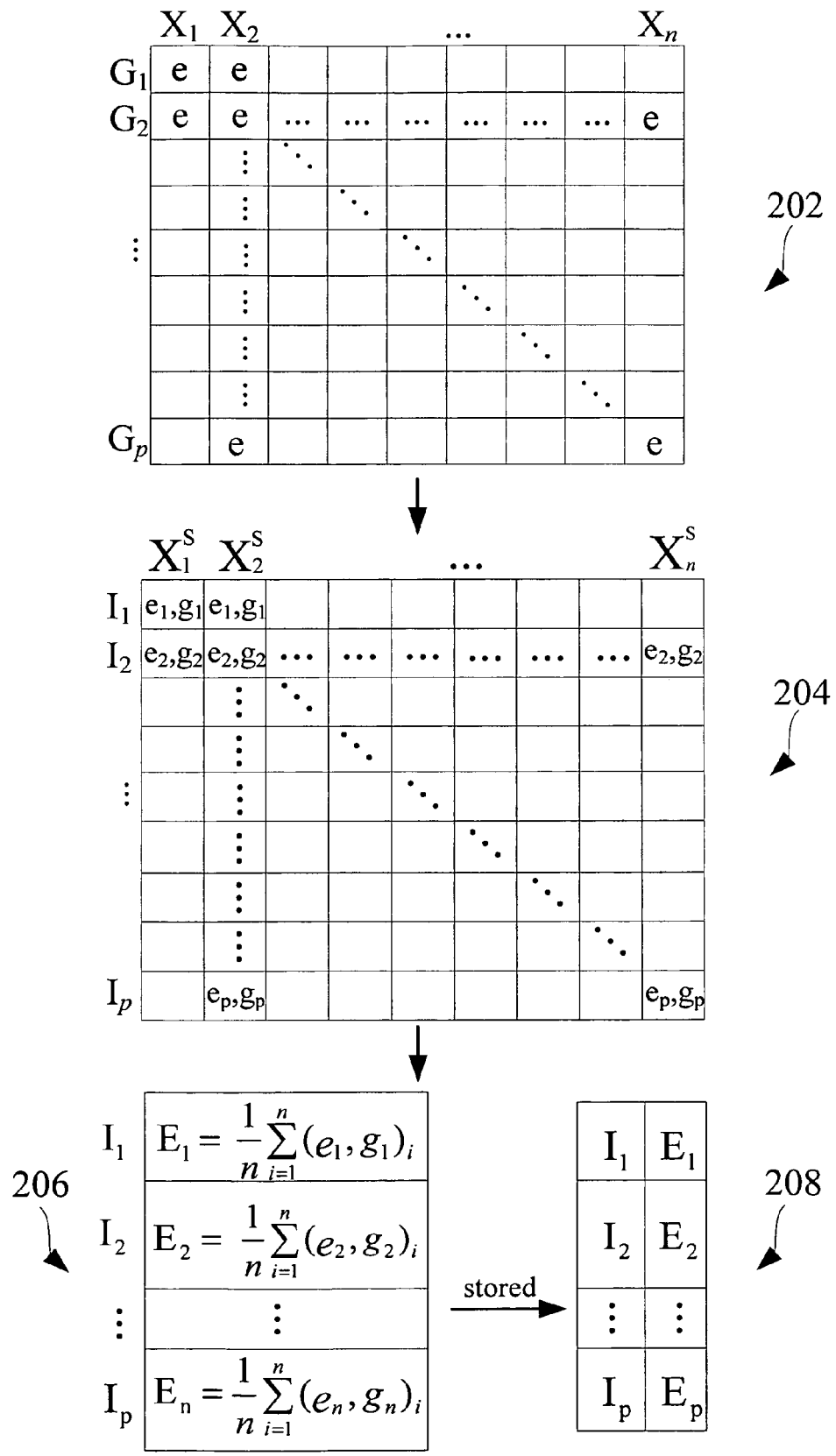
FIG. 2A illustrates an algorithm for constructing a standardization data structure in accordance with one embodiment of the present invention.
Figure 2B:
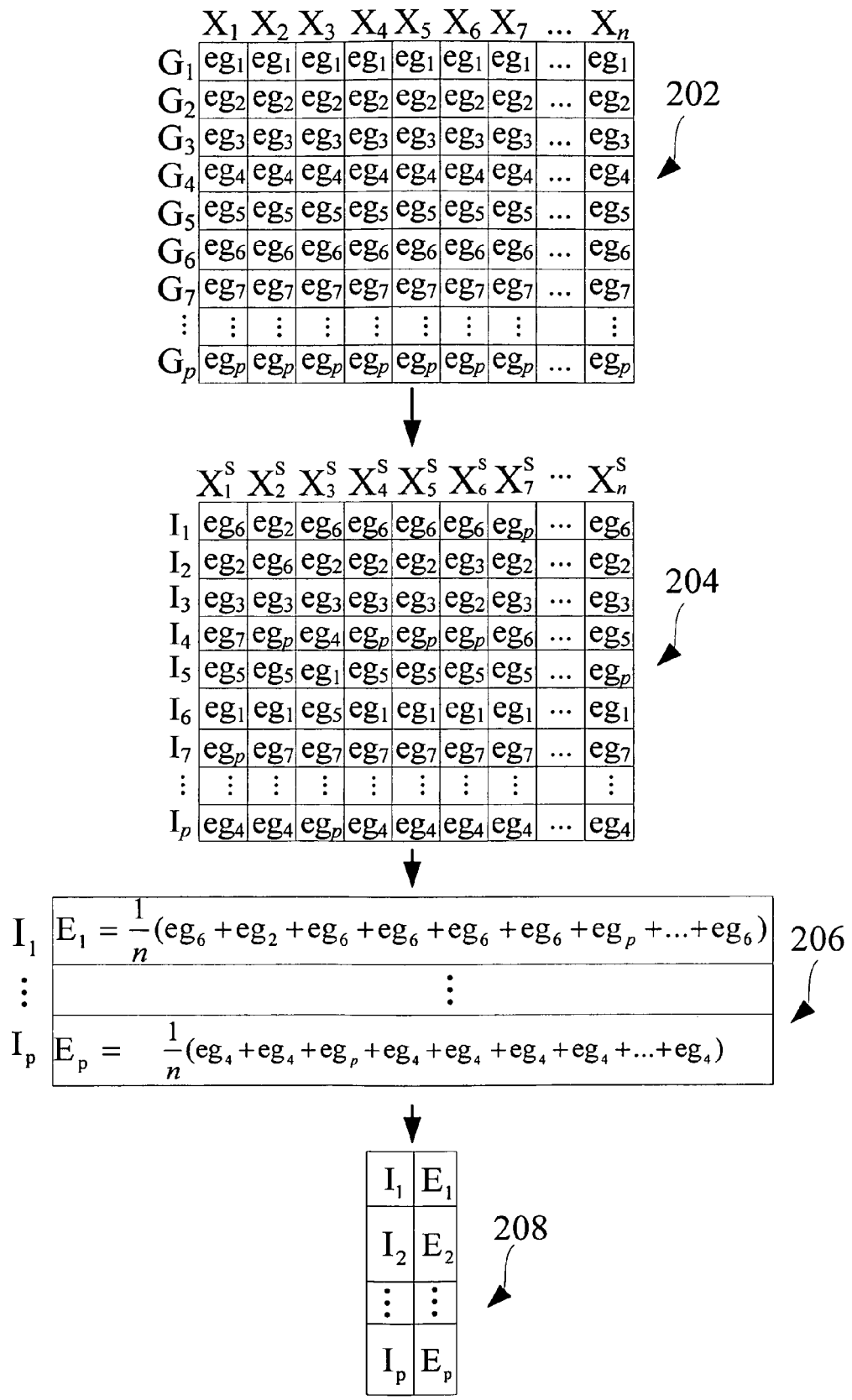
FIG. 2B illustrates the use of the algorithm of FIG. 2A in constructing a standardization data structure.
Figure 2C:
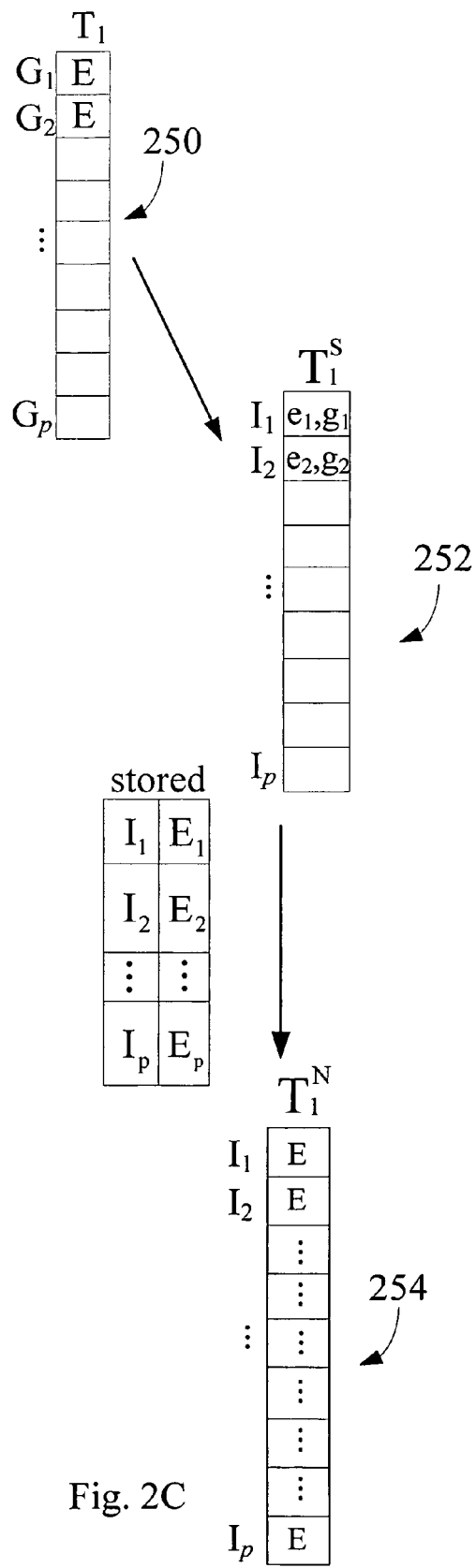

FIG. 2C illustrates the application of a standardization data structure, constructed in the manner illustrated in FIG. 2A, to a test microarray dataset in accordance with an embodiment of the present invention. FIG. 2C represents the case where each measure of central tendency in a standardization data structure is for a set of cellular constituent abundance values. Each cellular constituent abundance value in the set is the cellular constituent abundance value of a cellular constituent from a different training microarray dataset in a plurality of training microarray datasets that has the same ranking and the identifier for the corresponding measure of central tendency is the cellular constituent abundance value ranking in the training microarray datasets.

Figure 2D:
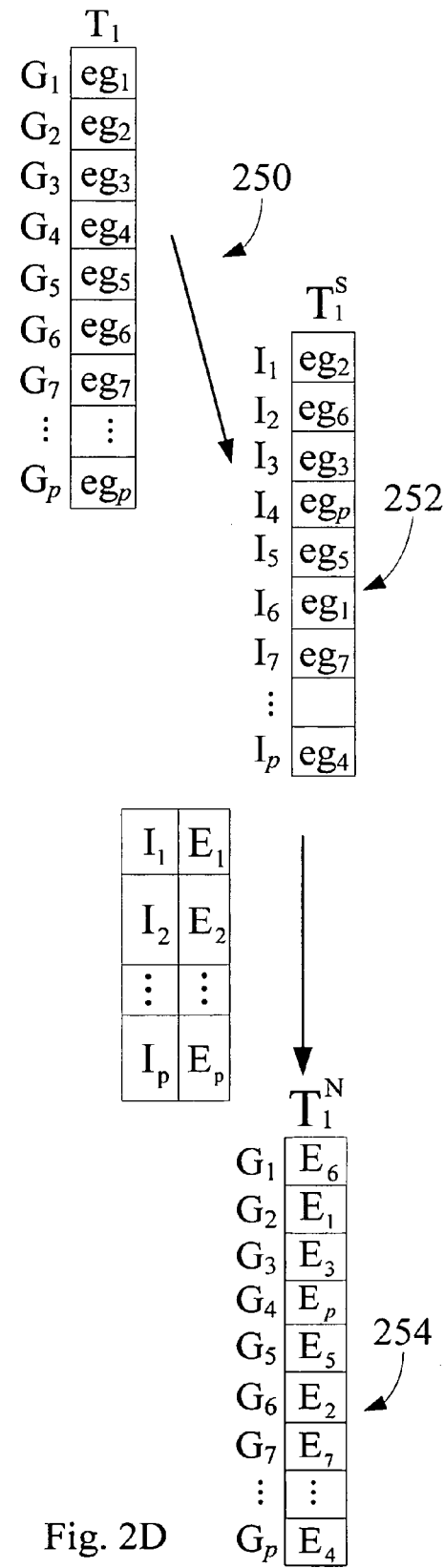

FIG. 2D illustrates a specific example of the application of a standardization data structure, constructed in the manner illustrated in FIG. 2A, to a test microarray dataset in accordance with an embodiment of the present invention.

Figure 3A:
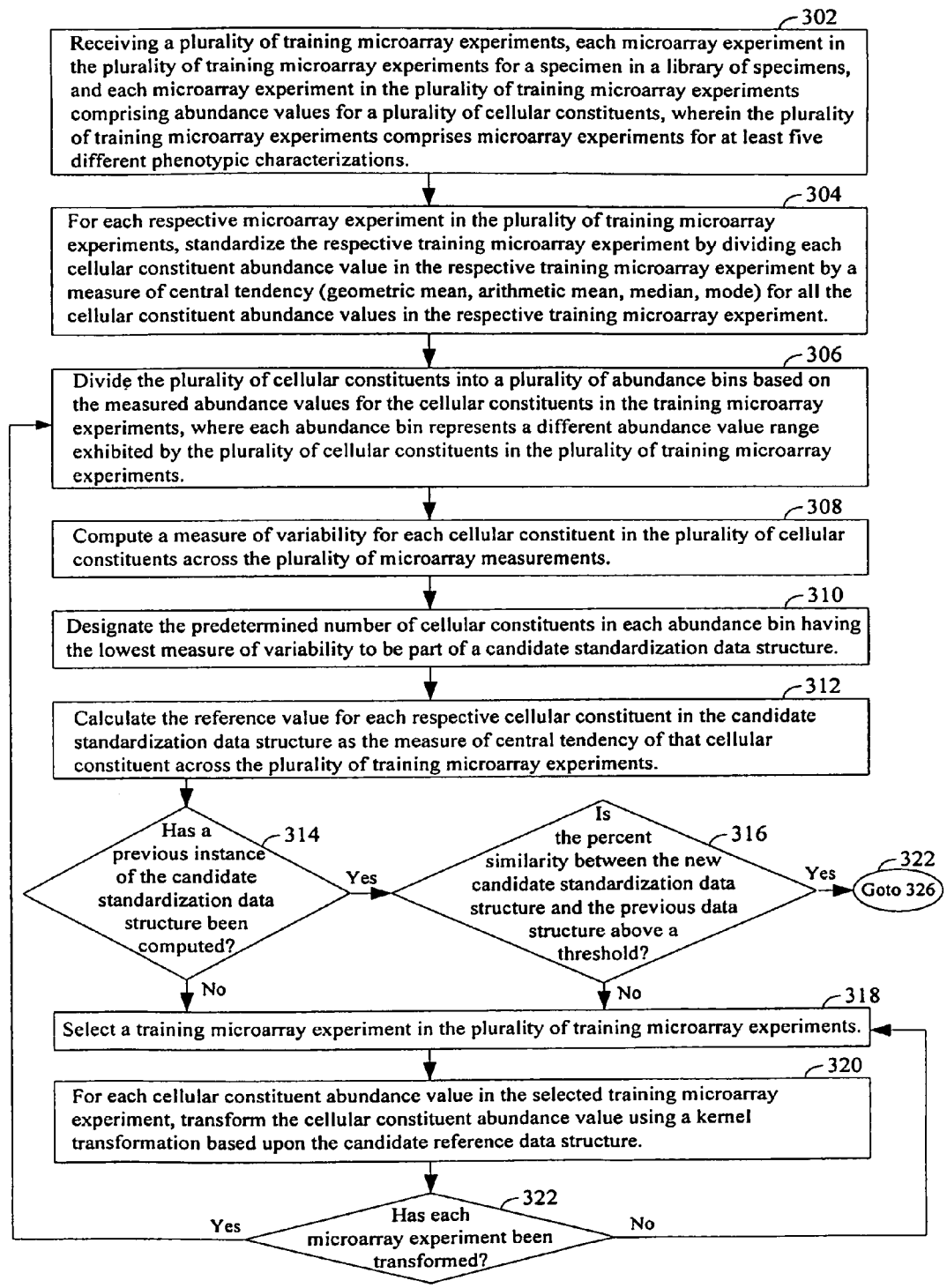
Figure 3B:
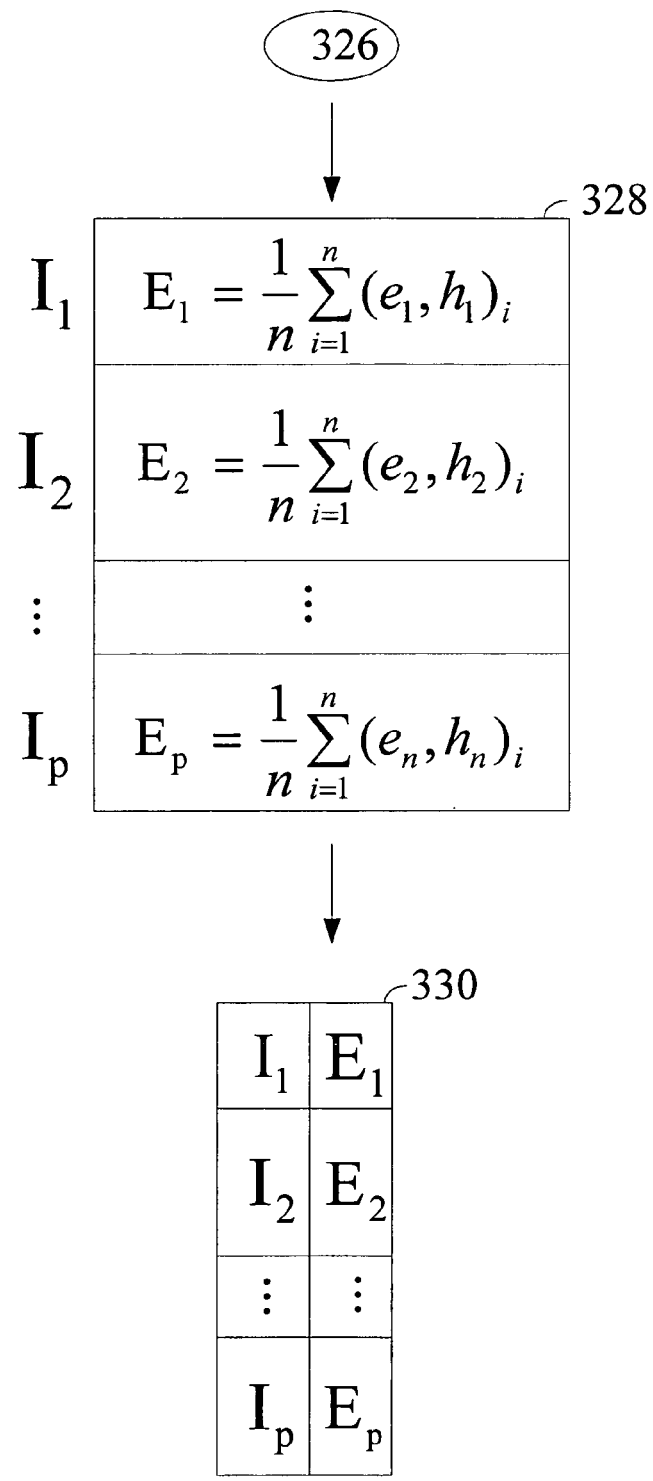

FIGS. 3A & 3B illustrate an algorithm for constructing a standardization data structure in accordance with another embodiment of the present invention.

Figure 3C:

FIG. 3C illustrates a specific example of the application of a standardization data structure, constructed in the manner illustrated in FIGS. 3A and 3B, to a test microarray dataset in accordance with an embodiment of the present invention. FIG. 3C represents the case where each measure of central tendency in a standardization data structure is for a set of cellular constituent abundance values. Each cellular constituent abundance value in the set is the cellular constituent abundance value of the same cellular constituent from a different training microarray dataset in a plurality of training microarray datasets and the identifier for the corresponding measure of central tendency is the identity of the cellular constituent.

Figure 4A:
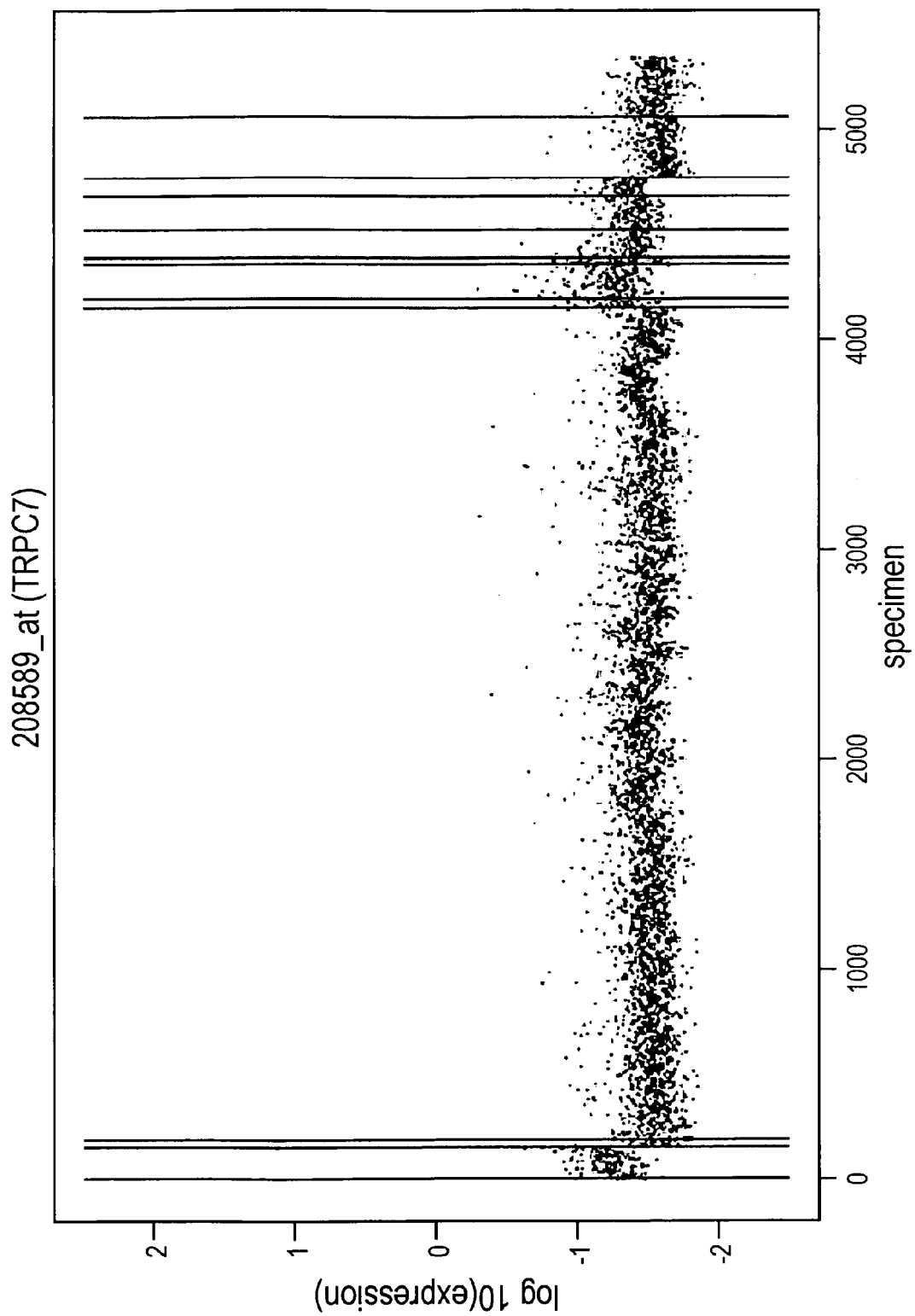

FIG. 4A illustrates the expression pattern for the housekeeping gene candidate (Affymetrix U133A ID 208589_at, gene symbol TRPC7, transient receptor potential cation channel) across 5,539 specimens. Vertical lines in FIG. 4A represent boundaries between processing laboratories.

Figure 4B:
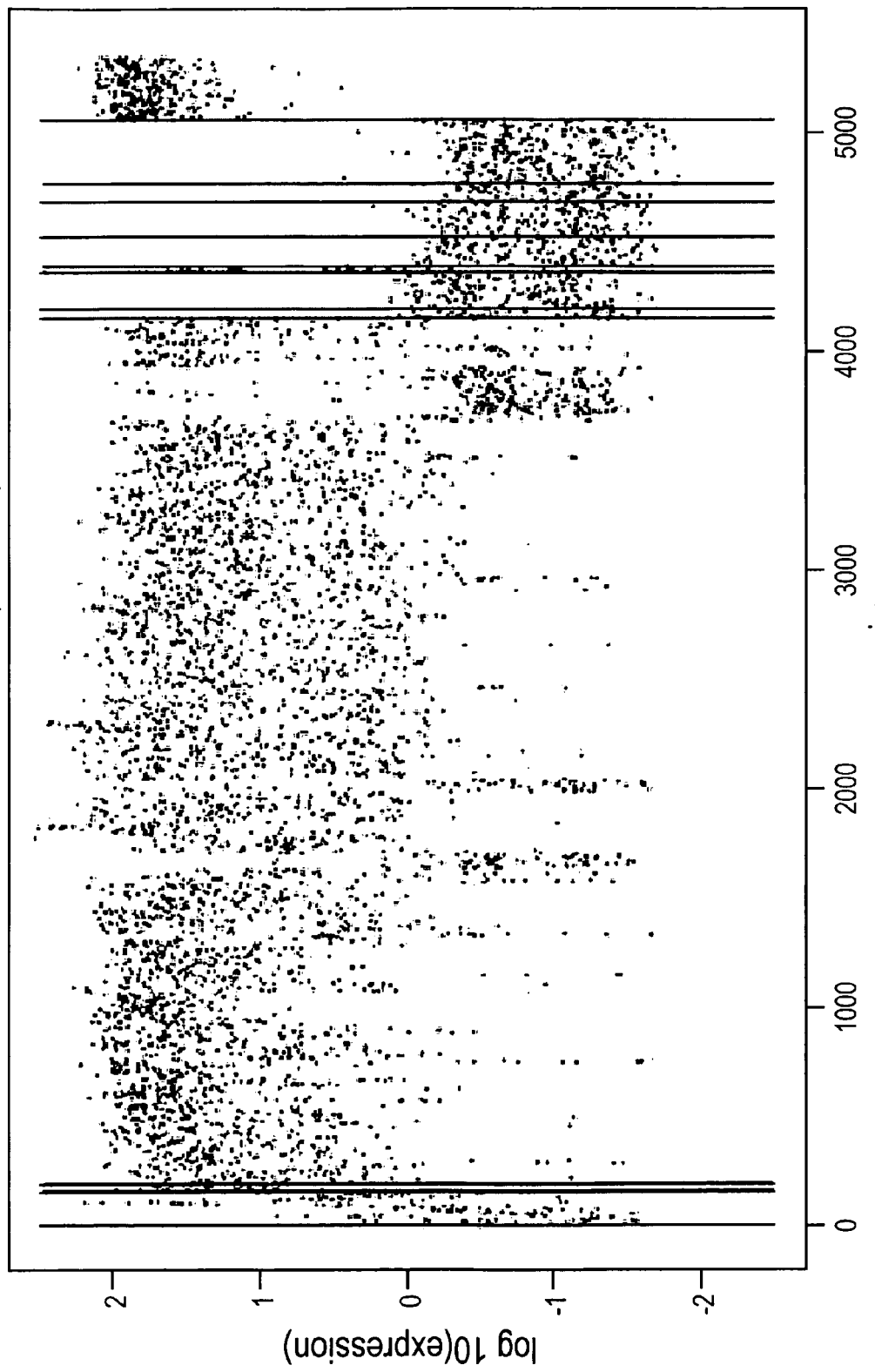

FIG. 4B illustrates the expression pattern for the non-housekeeping gene (Affymetrix U133A ID 202404_s_at, gene symbol COL1A2, collagen of skin, tendon and bone, alpha-2 chain) across the library of 5,539 specimens. Vertical lines represent boundaries between processing laboratories.

Figure 5:
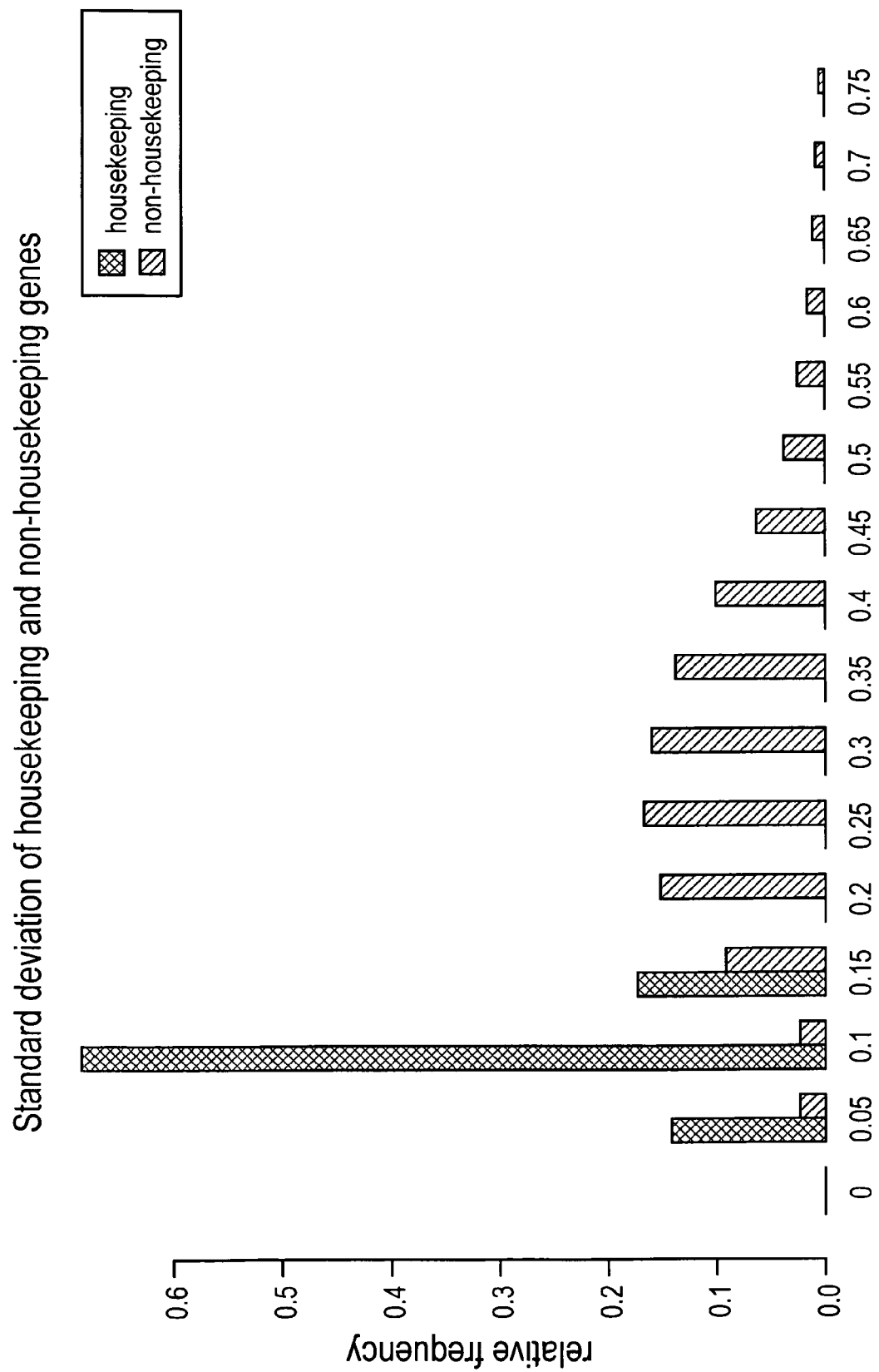

FIG. 5 illustrates histograms of standard deviation of expression values for 121 housekeeping and for nonhousekeeping genes across a library of 5,539 training microarray datasets corresponding to 5,539 specimens.

Figure 6:
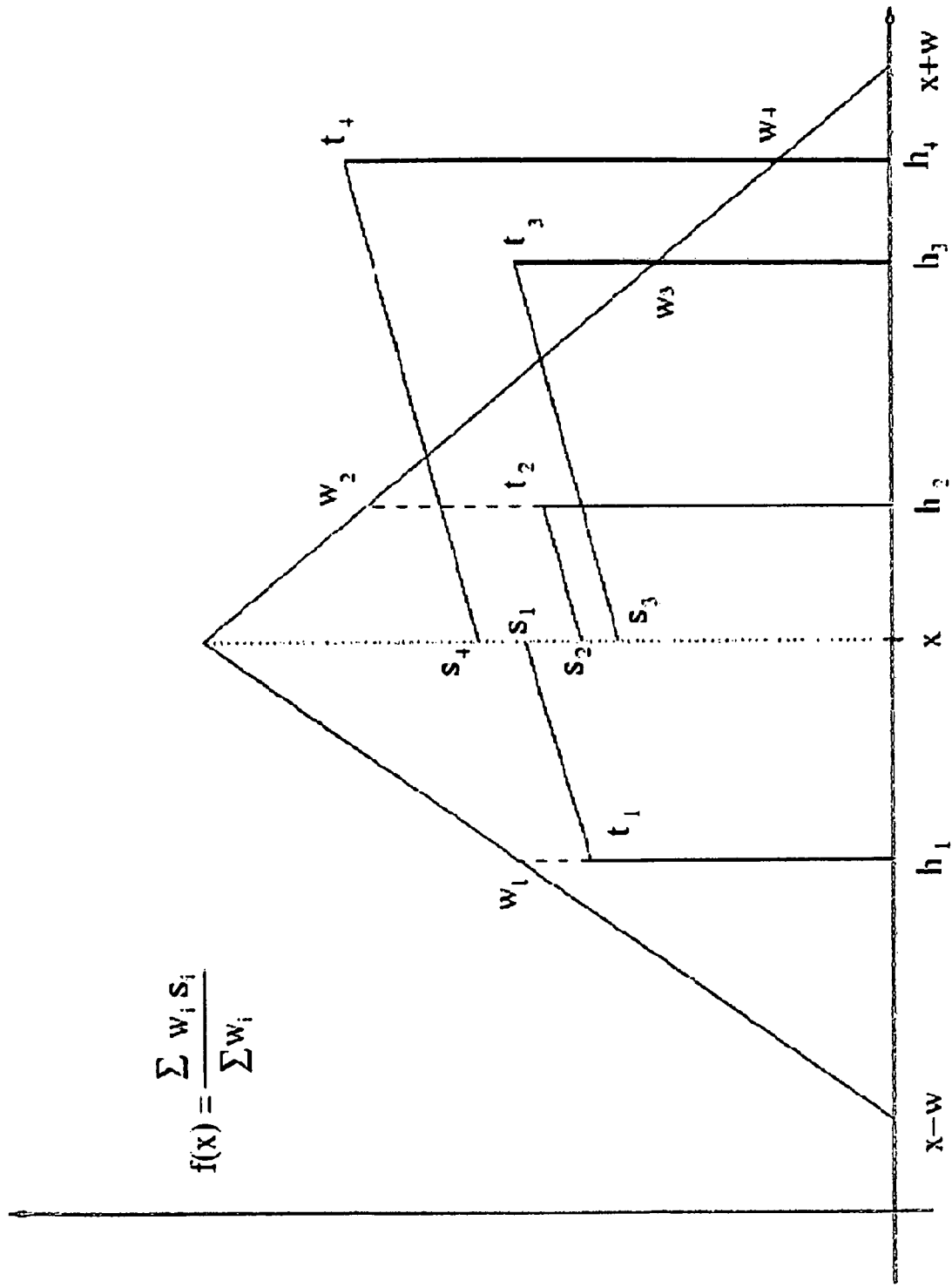

FIG. 6 illustrates a kernel transformation for a given cellular constituent abundance value x in accordance with an embodiment of the present invention.

Like reference numerals refer to corresponding parts throughout the several views of the drawings.

5 DETAILED DESCRIPTION OF THE INVENTION

FIG. 1 details an exemplary system 11 for use in the construction of a standardization data structure in accordance with the methods of the present invention. The system preferably comprises a computer system 10 having:

a central processing unit 22;
a main non-volatile storage unit 14, for example a hard disk drive, for storing software and data, the storage unit 14 controlled by storage controller 12;
a system memory 36, preferably high speed random-access memory (RAM), for storing system control programs, data, and application programs, comprising programs and data loaded from non-volatile storage unit 14; system memory 36 may also include read-only memory (ROM);
a user interface 32, comprising one or more input devices (e.g., keyboard 28, a mouse) and a display 26 or other output device;
a network interface card 20 (communications circuitry) for connecting to any wired or wireless communication network 34 (e.g., a wide area network such as the Internet);
a power source 24 to power the aforementioned elements; and
an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

a file system 42 for controlling access to the various files and data structures used by the present invention;
training microarray dataset data store 44 that comprises training microarray datasets 46 that are used in the construction of a standardization data structure 64;
an optional preprocessing module 60 that is optionally used to preprocess training microarray datasets 46;
a standardization data structure construction module 62 that is used to construct a standardization data structure 64.

As illustrated in FIG. 1, computer 10 comprises a training microarray dataset data store 44. Data store 44 can be any form of data storage system including, but not limited to, a flat file, a relational database (SQL), or an on-line analytical processing (OLAP) database (MDX and/or variants thereof). In some specific embodiments, data store 44 is a hierarchical OLAP cube. In some specific embodiments, data store 44 comprises a star schema that is not stored as a cube but has dimension tables that define hierarchy. Still further, in some embodiments, data store 44 has hierarchy that is not explicitly broken out in the underlying database or database schema (e.g., dimension tables that are not hierarchically arranged). In some embodiments, data store 44 is a single database that includes training microarray datasets 46. In other embodiments, data store 44 in fact comprises a plurality of databases that may or may not all be hosted by the same computer 10. In such embodiments, some components of data store 44 are stored on computer systems that are not illustrated by FIG. 1 but that are addressable by wide area network 34.

In some embodiments, data store 44 has training microarray datasets 46 for at least one phenotypic characterization, at least two phenotypic characterizations, at least three phenotypic characterizations, at least four phenotypic characterizations, or at least five different phenotypic characterizations. In some embodiments, data store 44 has at least 2, at least 5, at least 8, at least 10, at least twenty-five, at least fifty, at least one hundred, or at least two hundred different training microarray datasets 46 for each such phenotypic characterization.

Figure 1A:
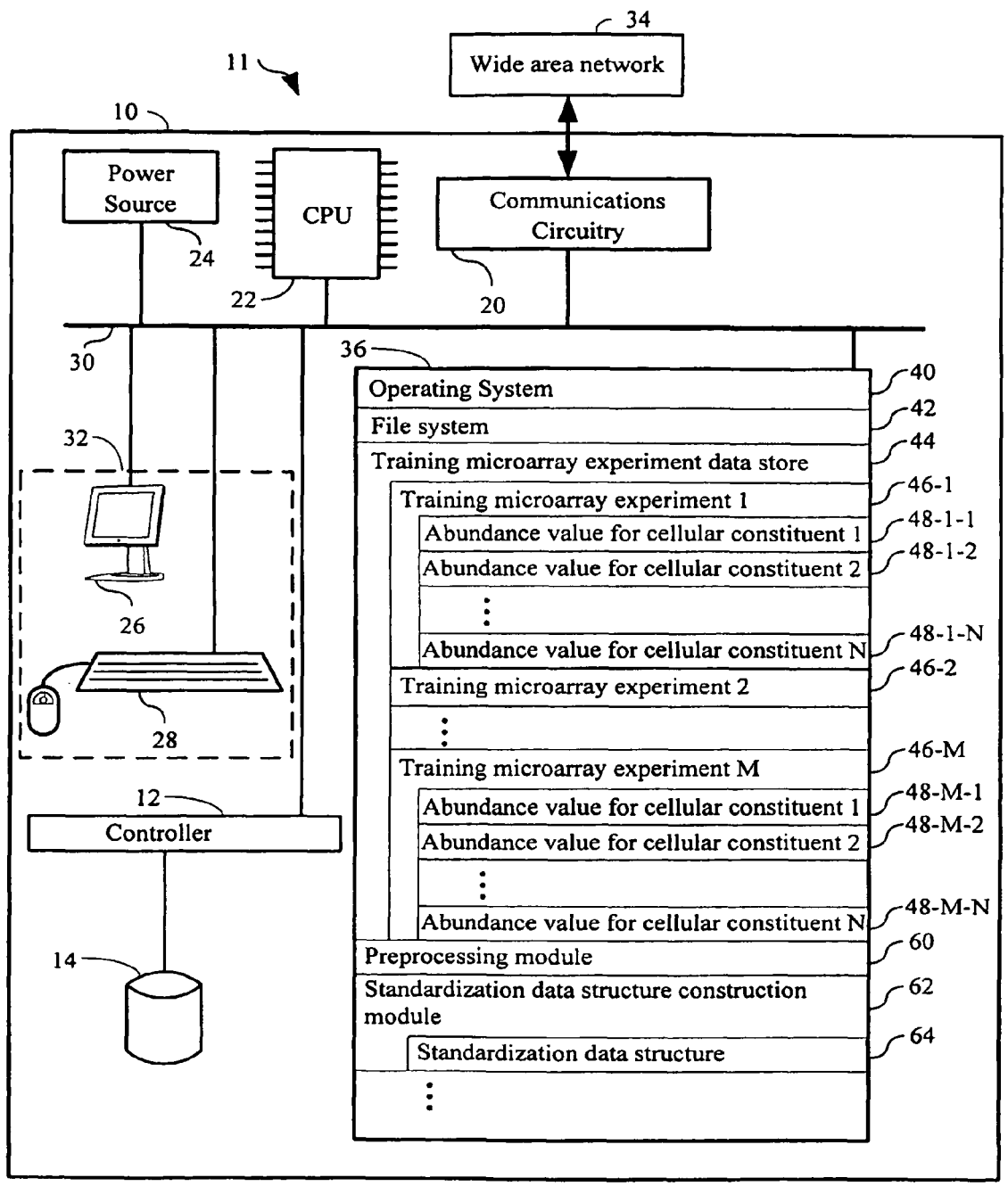
FIG. 1A shows an exemplary computer system for constructing a standardization data structure in accordance with an embodiment of the present invention.

In some embodiments, data store 44 and related software modules illustrated in FIG. 1A (e.g. modules 60 and 64) illustrated in FIG. 1A are on a single computer (e.g., computer 10) and in other embodiments data store 44 and related software modules illustrated in FIG. 1A are hosted by several computers (not shown). In fact, any arrangement of data store 44 and the modules illustrated in FIG. 1A on one or more computers is within the scope of the present invention so long as these components are addressable with respect to each other across network 34 or by other electronic means. Thus, the present invention fully encompasses a broad array of computer systems.

As discussed above, system 11 is used to construct a standardization data structure 64 in accordance with the methods of the present invention. The standardization data structure 64 is highly advantageous because it can be used to standardize microarray data from not only the laboratories that contributed training microarray datasets 46 that were used to construct the standardization data structure 64 but also labs that did not contribute training microarray datasets 46 to the construction of standardization data structure 64. Thus, of standardization data structure 64 can be used to standardize microarray datasets that have, for example, different exposure times, different exposure temperatures, different drying protocols, different washing protocols, or different scanners than the training microarray datasets 46 that were used to construct the standardization data structure 64.

As depicted in FIG. 1A, in typical embodiments each training microarray dataset 46 comprises abundance values 48 for a plurality of cellular constituents. In preferred embodiments, each training microarray dataset 46 is derived from a single micorarray. So, for example, if 10 training microarray datasets 46 are measured, they would be measured from ten corresponding microarrays, where there is a one-to-one correspondence between the microarrays and the training microarray datasets 46. As used herein, the term "cellular constituent" comprises a gene, a protein (e.g. a polypeptide, apeptide), a proteoglycan, a glycoprotein, a lipoprotein, a carbohydrate, a lipid, a nucleic acid, an mRNA, a cDNA, an oligonucleotide, a microRNA, a tRNA, or a protein with a particular (selected) modification. Thus, the term cellular constituent comprises a protein encoded by a gene, an mRNA transcribed from a gene, any and all splice variants encoded by a gene, cRNA of mRNA transcribed from a gene, any nucleic acid that contains the nucleic acid sequence of a gene, or any nucleic acid that is hybridizable to a nucleic acid that contains the nucleic acid sequence of a gene or mRNA translated from a gene under standard microarray hybridization conditions. Furthermore, an "abundance value" for a cellular constituent is a quantification of an amount of any of the foregoing, an amount of activity of any of the foregoing, or a degree of modification (e.g., phosphorylation) of any of the foregoing. As used herein, a gene is a transcription unit in the genome, including both protein coding and noncoding mRNAs, cDNAs, or cRNAs for mRNA transcribed from the gene, or nucleic acid derived from any of the foregoing. As such, a transcription unit that is optionally expressed as a protein, but need not be, is a gene. The abundance values used in the methods of the invention are all of the same class of abundance values. For example, they are all amounts of mRNA, all amounts of cDNA, all amounts of protein, all amounts of metabolites, all activity levels of proteins, or all degrees of a chosen modification (e.g., phosphorylation of proteins, etc.), etc. In some embodiments, the abundance value for a cellular constituent is determined by a degree of modification of a cellular constituent that is encoded by or is a product of a gene (e.g., is a protein or RNA transcript). In some embodiments, a cellular constituent is virtually any detectable compound, such as a protein, a peptide, a proteoglycan, a glycoprotein, a lipoprotein, a carbohydrate, a lipid, a nucleic acid (e.g., DNA, such as cDNA or amplified DNA, or RNA, such as mRNA), an organic or inorganic chemical, a natural or synthetic polymer, a small molecule (e.g., a metabolite) and/or any other variable cellular component or protein activity, a protein with a selected modification (e.g., phosphorylation), or a discriminating molecule or discriminating fragment of any of the foregoing, that is present in or derived from a biological sample that is modified by, regulated by, or encoded by a gene.

A cellular constituent can, for example, be isolated from a biological sample from a member of the first population, directly measured in the biological sample from the member of the first population, or detected in or determined to be in the biological sample from the member of the first population. A cellular constituent can, for example, be functional, partially functional, or non-functional. In addition, if the cellular constituent is a protein or fragment thereof, it can be sequenced and its encoding gene can be cloned using well-established techniques.

A cellular constituent can be an RNA encoding a gene that, in turn, encodes a protein or a portion of a protein. However, a cellular constituent can also be an RNA that does not necessarily encode for a protein or a portion of a protein. As such, in the present invention, a "gene" is any region of the genome that is transcriptionally expressed. Thus, examples of genes are regions of the genome that encode microRNAs, tRNAs, and other forms of RNA that are encoded in the genome as well as those genes that encode for proteins (e.g. messenger RNA).

In some embodiments, the cellular constituent abundance data for a gene is a degree of modification of the cellular constituent. Such a degree of modification can be, for example, an amount of phosphorylation of the cellular constituent. Such measurements are a form of cellular constituent abundance data. In one embodiment, the abundance of the at least one cellular constituent that is measured and stored as abundance value 48 for a cellular constituent comprises abundances of at least one RNA species present in one or more cells. Such abundances can be measured by a method comprising contacting a gene transcript array with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species.

Figure 1B:
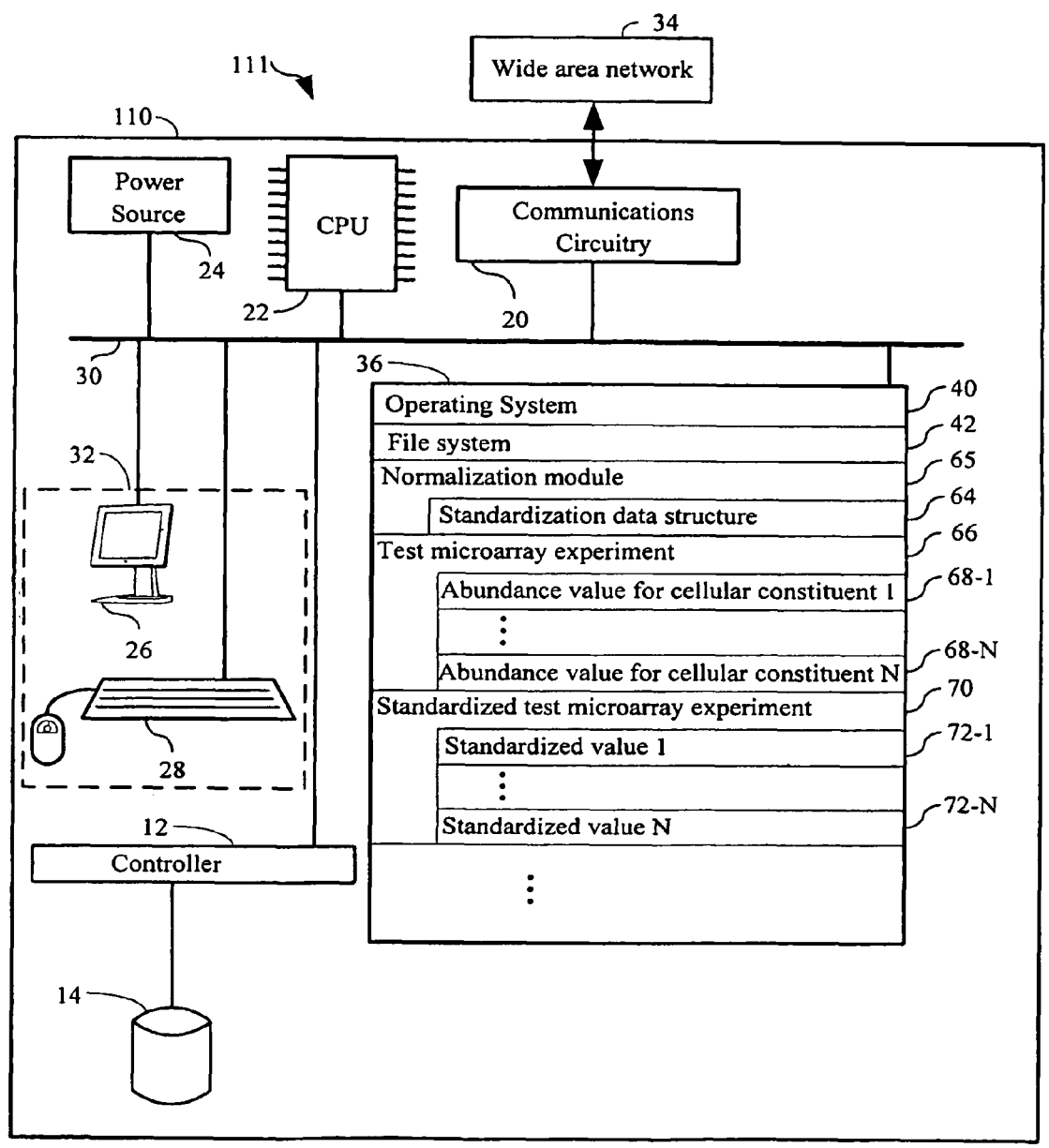
FIG. 1B illustrates an exemplary computer system for applying a standardization data structure to a test microarray dataset in accordance with an embodiment of the present invention.

In some embodiments, the standardization data structure 64 is retained in the same computer system 11 that was used to build the data structure in the first place, e.g. computer system 11 of FIG. 1A. There, the standardization data structure 64 can be used to standardize microarray datasets that, for example, were not used to build the data structure 64. In some embodiments, the standardization data structure 64 is transferred to a different computer system 111, depicted in FIG. 1B, once it has been constructed, where it is then used to standardize test microarray datasets 66. In preferred embodiments, a test microarray dataset 66 is any microarray dataset that was not used as a training microarray dataset 46 in the construction of the standardization data structure 64. As in the case of the training microarray datasets, in preferred embodiments, the training microarray datasets are each obtained from a single microarray. As depicted in FIG. 1B, system 111 includes components that are similar or identical to like referenced elements of system 11 (FIG. 1A). Further, system 111 includes a normalization module 65 that is used to standardize test microarray datasets 66. A test microarray dataset 66 comprises abundance values for cellular constituents 68. Cellular constituents 68 can be any of the cellular constituents described above for the cellular constituents 48 of the training microarray datasets 46.

In some embodiments, each training microarray dataset 46 and/or each test microarray dataset 66 comprises the cellular constituent abundance values from microarrays that are designed to quantify an amount of nucleic acid in a biological sample. Such microarrays are referred to herein as expression microarrays. Examples of such microarrays include, but are not limited to, the Affymetrix GENECHIP Human Genome U133A 2.0 Array (Santa Clara, Calif.) which is a single array representing 14,500 human genes. In the case of training microarray datasets 46, such values are referred to as abundance values 48 as depicted in FIG. 1A. In the case of test microarray datasets 66, such values are referred to as abundance values 68 as depicted in FIG. 1B. In some embodiments, each training microarray dataset 46 and/or each standardized test microarray dataset 66 comprises the cellular constituent abundance values from any Affymetrix expression (quantitation) analysis array including, but not limited to, the ENCODE 2.0R array, the HuGeneFL Genome Array, the Human Cancer G110 Array, the Human Exon 1.0 ST Array, the Human Genome Focus Array, the Human Genome U133 Array Plate Set, the Human Genome U133 Plus 2.0 Array, the Human Genome U133 Set, the Human Genome U133A 2.0 Array, the Human Genome U95 Set, the Human Promoter 1.0R array, the Human Tiling 1.0R Array Set, the Human Tiling 2.0R Array Set, and the Human X3P Array.

In some embodiments, each training microarray dataset 46 and/or each test microarray dataset 66 comprises the cellular constituent abundance values from microarrays that are designed for comparative genomic hybridization (CGH). CGH encompasses methods that are used to analyze copy number changes (gains/losses) in the DNA content of biological specimens, and/or discover or validate microdeletions or microinsertions in genomic DNA. Such microarrays are referred to herein as comparative genomic hybridization microarrays. Examples of comparative genomic hybridization microarrays include, but are not limited to, the submegabase resolution tiling arrays (SMRT version 1 & 2) which are tiling path resolution microarrays comprising 32,433 and 26,526 synthetic bacterial artificial chromosomes respectively. SMRT array version 1 is spotted in triplicate and SMRT array version 2 is spotted in duplicate on one slide. Both arrays are for use in comparative genomic hybridization experiments. The SMRT arrays are available from the Wan Lam Laboratory at the British Columbia Cancer Research Centre, (Vancouver, British Columbia, Canada). For a description of the use of SMRT arrays in one CGH analysis, see Shah et al., 2006, Bioinformatics 22, e431-e439, which is hereby incorporated by reference herein in its entirety. In some instances CGH arrays are constructed from BAC, PAC, or cosmid clones. Additional CGH microarrays include, but are not limited to, the Affymetrix Mapping 100K set, Mapping 10K 2.0 set, and Mapping 500K set. Additional CGH microarrays include, but are not limited to, the Agilent Human Genome CGH Microarray Kit 244K, the Agilent Human Genome CGH Microarray Kit 105K, and the Agilent Human Genome CGH Microarray Kit 44K.

In some embodiments, each training microarray dataset 46 and/or each test microarray dataset 66 comprises the cellular constituent abundance values from an exon microarray. Exon microarrays provide at least one probe per exon in genes traced by the microarray to allow for analysis of gene expression and alternative splicing. Examples of exon microarrays include, but are not limited to, the Affymetrix GENECHIP® Human Exon 1.0 ST array. The GENECHIP® Human Exon 1.0 ST array supports most exonic regions for both well-annotated human genes and abundant novel transcripts. A total of over one million exonic regions are registered in this microarray system. The probe sequences are designed based on two kinds of genomic sources, i.e. cDNA-based content which includes the human RefSeq mRNAs, GenBank and ESTs from dbEST, and the gene structure sequences which are predicted by GENSCAN, TWINSCAN, and Ensemble. The majority of the probe sets are each composed of four perfect match (PM) probes of length 25 bp, whereas the number of probes for about 10 percent of the exon probe sets is limited in less than four due to the length of probe selection region and sequence constraints. With this microarray platform, no mismatch (MM) probes are available to perform data normalization, for example, background correction of the monitored probe intensities. Instead of the MM probes, the existing systematic biases are removed based on the observed intensities of the background probe probes (BGP) which are designed by Affymetrix. The BGPs are composed of the genomic and antigenomic probes. The genomic BGPs were selected from a research prototype human exon array design based on NCBI build 31. The antigenomic background probe sequences are derived based on reference sequences that are not found in the human (NCBI build 34), mouse (NCBI build 32), or rat (HGSC build 3.1) genomes. Multiple probes per exon enable "exon-level" analysis provide a basis for distinguishing between different isoforms of a gene. This exon-level analysis on a whole-genome scale opens the door to detecting specific alterations in exon usage that may play a central role in disease mechanism and etiology.

In some embodiments, each training microarray dataset 46 and/or each test microarray dataset 66 comprises the cellular constituent abundance values from a microRNA microarray. MicroRNAs (miRNAs) are a class of non-coding RNA gene whose final product is a 22 nucleotide functional RNA molecule. MicroRNAs play roles in the regulation of target genes by binding to complementary regions of messenger transcripts to repress their translation or regulate degradation. MicroRNAs have been implicated in cellular roles as diverse as developmental timing in worms, cell death and fat metabolism in flies, haematopoiesis in mammals, and leaf development and floral patterning in plants. MicroRNAs may play roles in human cancers. Examples of exon microarrays include, but are not limited to, the Agilent Human miRNA Microarray kit which contains probes for 470 human and 64 human viral microRNAs from the Sanger database v9.1.

In some embodiments, each training microarray dataset 46 and/or each test microarray dataset 66 comprises protein abundance or protein modification measurements that are made using a protein chip assay (e.g., The PROTEINCHIP® Biomarker System, Ciphergen, Fremont, Calif.). See also, for example, Lin, 2004, Modern Pathology, 1-9; Li, 2004, Journal of Urology 171, 1782-1787; Wadsworth, 2004, Clinical Cancer Research 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, each of which is hereby incorporated by reference herein in its entirety. Protein chip assays (protein microarrays) are commercially available. For example, Ciphergen (Fremont, Calif.) markets the PROTEINCHIP® System Series 4000 for quantifying proteins in a sample. Furthermore, Sigma-Aldrich (Saint Lewis, Mo.) sells a number of protein microarrays including the PANORAMA™ Human Cancer v1 Protein Array, the PANORAMA™ Human Kinase v1 Protein Array, the PANORAMA™ Signal Transduction Functional Protein Array, the PANORAMA™ AB Microarray—Cell Signaling Kit, the PANORAMA™ AB Microarray—MAPK and PKC Pathways kit, the PANORAMA™ AB Microarray—Gene Regulation I Kit, and the PANORAMA™ AB Microarray—p53 pathways kit. Further, TeleChem International, Inc. (Sunnyvale, Calif.) markets a Colorimetric Protein Microarray Platform that can perform a variety of micro multiplexed protein microarray assays including microarray based multiplex ELISA assays. See also, MacBeath and Schreiber, 2000, "Printing Proteins as Microarrays for High-Throughput Function Determination," Science 289, 1760-1763, which is hereby incorporated by reference herein in its entirety.

In some embodiments, each training microarray dataset 46 and/or each test microarray dataset 66 comprises the cellular constituent abundance values measured using any of the techniques and microarrays disclosed in Section 5.5, below.

In some embodiments, each training microarray dataset 46 and/or each test microarray dataset 66 comprises data for a plurality of oligonucleotide probes, wherein the plurality of oligonucleotides consists of between 1,000 and $5 \times 10^6$ oligonucleotides. In some embodiments, each training microarray dataset 46 and/or each test microarray dataset 66 comprises data for a plurality of oligonucleotide probes, wherein the plurality of oligonucleotides consists of between 100 and $1 \times 10^8$ oligonucleotides, between 500 and $1 \times 10^7$ oligonucleotides, between 1000 and $1 \times 10^6$ oligonucleotides, or between 2000 and $1 \times 10^5$ oligonucleotides. In some embodiments, each training microarray dataset 46 and/or each test microarray dataset 66 comprises data for a plurality of oligonucleotide probes, wherein the plurality of oligonucleotides consists of more than 100, more than 1000, more than 5000, more than 10,000, more than 15,000, more than 20,000, more than 25,000, or more than 30,000 oligonucleotides. In some embodiments, each training microarray dataset 46 and/or each test microarray dataset 66 comprises data for a plurality of oligonucleotide probes, wherein the plurality of oligonucleotides consists of less than $1 \times 10^7$, less than $1 \times 10^6$, less than $1 \times 10^5$, or less than $1 \times 10^4$ oligonucleotides.

In some embodiments, each training microarray dataset 46 and/or each test microarray dataset 66 comprises data (e.g., abundance values) for a plurality of mRNAs, wherein the plurality of mRNAs consists of between 1,000 and 50,000 mRNAs. In some embodiments, each training microarray dataset 46 and/or each test microarray dataset 66 comprises data for a plurality of mRNAs, wherein the plurality of mRNAs consists of between 500 and 100,000 mRNAs, between 2000 and 80,000 mRNAs, or between 5000 and 40,000 mRNAs. In some embodiments, each training microarray dataset 46 and/or each test microarray dataset 66 comprises data for a plurality of mRNAs, wherein the plurality of mRNAs consists of more than 100 mRNAs, more than 500 mRNAs, more than 1000 mRNAs, more than 2000 mRNAs, more than 5000 mRNAs, more than 10,000 mRNAs, or more than 20,000 mRNAs. In some embodiments, each training microarray dataset 46 and/or each test microarray dataset 66 comprises data for a plurality of mRNAs, wherein the plurality of mRNAs consists of less than 100,000 mRNAs, less than 50,000 mRNAs, less than 25,000 mRNAs, less than 10,000 mRNAs, less than 5000 mRNAs, or less than 1,000 mRNAs.

In some embodiments, each training microarray dataset 46 and/or each test microarray dataset 66 comprises data (e.g., abundance values) for a plurality of proteins, wherein the plurality of proteins consists of between 50 and 200,000 proteins. In some embodiments, each training microarray dataset 46 and/or each test microarray dataset 66 comprises data for a plurality of proteins, wherein the plurality of proteins consists of between 25 and 500,000 proteins, between 50 and 400,000 proteins, or between 1000 and 100,000 proteins. In some embodiments, each training microarray dataset 46 and/or each test microarray dataset 66 comprises data for a plurality of proteins, wherein the plurality of proteins consists of more than 100 proteins, more than 500 proteins, more than 1000 proteins, more than 2000 proteins, more than 5000 proteins, more than 10,000 proteins, or more than 20,000 proteins. In some embodiments, each training microarray dataset 46 and/or each test microarray dataset 66 comprises data for a plurality of proteins, wherein the plurality of proteins consists of less than 500,000 proteins, less than 250,000 proteins, less than 50,000 proteins, less than 10,000 proteins, less than 5000 proteins, or less than 1,000 proteins.

In some embodiments, the training microarray dataset data store 44 consists of between 1,000 and 100,000 training microarray datasets. In some embodiments, training microarray dataset data store 44 consists of between 500 and 50,000 training microarray datasets. In some embodiments, training microarray dataset data store 44 consists of between 100 and 35,000 training microarray datasets. In some embodiments, training microarray dataset data store 44 consists of between 50 and 20,000 training microarray datasets.

In some embodiments, the test microarray dataset 66 and/or each training microarray dataset 46 is measured from a microarray comprising probes arranged with a density of 100 different probes per 1 cm$^2$ or higher. In some embodiments, the test microarray dataset 66 and/or each training microarray dataset 46 is measured from a microarray comprising probes arranged with a density of at least 2,500 different probes per 1 cm$^2$, at least 5,000 different probes per 1 cm$^2$, or at least 10,000 different probes per 1 cm$^2$.

In some embodiments, the test microarray dataset 66 and/or each training microarray dataset 46 is measured from a microarray comprising at least 10,000 different probes, at least 20,000 different probes, at least 30,000 different probes, at least 40,000 different probes, at least 100,000 different probes, at least 200,000 different probes, at least 300,000 different probes, at least 400,000 different probes, or at least 500,000 different probes.

In some embodiments, each respective training microarray dataset 46 and each respective test microarray dataset 66 contains measured cellular constituent abundance values from a particular corresponding biological specimen (specimen). Such biological specimens are obtained from subjects in order to measure the abundance values for cellular constituents. Unless otherwise indicated herein, any biological sample from an organ, tissue, or biological fluid, e.g., liver tissue sample, pancreatic tissue sample, soft tissue, muscle tissue, bone tissue, bladder tissue, lung tissue, epithelial tissue, endothelial tissue, blood sample, urine, mucosal swab, etc., obtained from any subject may serve as a biological specimen.

In some embodiments, as depicted in FIG. 1B, the computer 110 is in electrical communication with the wide area network 34 (e.g., the Internet) and the test microarray dataset 66 is received from a local or remote computer (not shown) over the wide area network. In some embodiments, normalization module 65 standardizes a test microarray dataset 66 thereby producing a standardized test microarray dataset 70. Then, the standardized test microarray dataset 70 is outputted by communicating the standardized test microarray dataset 70 to a local or remote computer system across the wide area network 34.

FIG. 1B illustrates a single test microarray dataset 66 and a single corresponding standardized test microarray dataset 70. In practice, normalization module 65 standardizes one test microarray dataset 66 at a time thereby producing a corresponding standardized test microarray dataset 70. In typical embodiments, the standardized test microarray dataset 70 will have the same number of cellular constituent abundance values (termed abundance values for cellular constituents 72) as the corresponding non-standardized test microarray dataset 66 (termed abundance values for cellular constituents 68), but many of the cellular constituent values 72 of the standardized test microarray dataset 70 will be adjusted relative to the corresponding cellular constituent values 68 of the corresponding test microarray dataset 66 in accordance with the methods disclosed below. It will be appreciated that computer 110 can store or access (e.g., from internal data storage 14 and/or memory 36 or from a remote computer over wide area network 34) any number of test microarray datasets 66 and produce and store any number of corresponding standardized test microarray datasets 70. However, in preferred embodiments, normalization module 65 standardizes a single test microarray dataset 66 to a single corresponding standardized test microarray dataset 70 at any given time by application of the standardization data structure 64 in accordance with the methods disclosed below.

FIG. 1C illustrates an exemplary standardization test structure 64 in accordance with an embodiment of the present invention. Standardization test structure 64 comprises a plurality of identifier 120 and, for each respective identifier, a corresponding measure of central tendency.

5.1 Exemplary Methods

In some embodiments, each measure of central tendency 140 in a standardization data structure 64 is for a set of cellular constituent abundance values. In some such embodiments, each cellular constituent abundance value in the set is the cellular constituent abundance value of a cellular constituent from a different training microarray dataset 46 in the training microarray dataset data store 44 that has the same ranking. Furthermore, the identifier 120 for the measure of central tendency in the standardization data structure is the cellular constituent abundance value ranking in the training microarray datasets. In some embodiments, the identifier 120 is not present and is simply derived from the order of a measure of central tendency in the standardization data structure 64. For example, the $10^{th}$ measure of central tendency is the measure of central tendency of the $10^{th}$ cellular constituent in each training microarray datasets after such datasets have been ranked based upon cellular constituent abundance. FIG. 2 illustrates methods for constructing the standardization data structure 64 in accordance with such embodiments as well as methods for applying the standardization data structure to an abundance value of each cellular constituent in a plurality of cellular constituents, thereby computing a standardized test microarray dataset.

In some embodiments, each measure of central tendency 140 in a standardization data structure 64 is for a set of cellular constituent abundance values. In some such embodiments, each cellular constituent abundance value in the set is the cellular constituent abundance value of the same cellular constituent from a different training microarray dataset 46 in the training microarray dataset data store 44. Furthermore, the identifier 120 for the measure of central tendency in the standardization data structure is the identity of the cellular constituent. FIG. 3 illustrates methods for constructing the standardization data structure 64 in accordance with such embodiments as well as methods for applying the standardization data structure to an abundance value of each cellular constituent in a plurality of cellular constituents, thereby computing a standardized test microarray dataset.

FIG. 2A illustrates one such method by which standardization data structure construction module 62 can generate a standardization data structure 64 from a plurality of training microarray datasets 46. In step 202 of FIG. 2A, the plurality of training microarray datasets 46 ($X_1 \ldots, X_n$) is considered as a two-dimensional table. Each column is a training microarray datasets 46 and each row is an abundance value (e) for a cellular constituent 68 ($G_1 \ldots, G_p$) in the training microarray datasets ($X_1 \ldots, X_n$). Thus, each box in the two-dimensional table of step 202 represents an abundance value (e) for a cellular constituent 48 in a training microarray dataset 46.

In step 204, the individual abundance values for cellular constituents are ranked on a column by column basis. In one ranking approach, cellular constituents 48 in a given training microarray dataset 46 are ranked from most abundant (top of the column) to least abundant (bottom of the column). In another ranking approach, cellular constituents 48 in a given training microarray dataset 46 are ranked from least abundant (top of the column) to most abundant (bottom of the column). In step 204, there is no guarantee that each of the cellular constituents in a given row of the table is the same after ranking. For example, cellular constituent "A" may be the most abundant in the first training microarray datasets 46 but only the second most abundant in the second training microarray datasets 46. So, in step 204, cellular constituent "A" would be in the top cell for the first training microarray datasets 46 but in the cell below the top cell for the second training microarray datasets 46 (in embodiments where cellular constituents are ranked from most abundant to least abundant). This point is illustrated in FIG. 2B which provides an illustration of the algorithm of FIG. 2A using exemplary data. As illustrated in step 202, each cell in the top row is the cellular constituent $eg_1$. But, when the cellular constituents are ranked by abundance value in step 204, it is seen that, for many of the exemplary training microarray datasets 46, the most abundant cellular constituent is $eg_6$ (those exemplary training microarray datasets 46 in which $eg_6$ rises to the top row of the two-dimensional chart). However, for exemplary training microarray dataset $X_2^S$, cellular constituent $eg_2$ is the most abundant and for exemplary training microarray dataset $X_7^S$, cellular constituent $eg_p$ is the most abundant. In the sorted two-dimensional table 204, each cellular constituent abundance value in a row ($e_1, g_1 \ldots, e_p, g_p$ in FIG. 2A; $eg_1 \ldots, eg_p$ in FIG. 2B) (collection of cellular constituent abundance values) is the cellular constituent abundance value for a cellular constituent from a different training microarray dataset 46 having the same cellular constituent abundance value ranking ($I_1 \ldots, I_p$) in the different training microarray datasets. The sorted training microarray datasets are denoted in FIGS. 2A-2B by $X_1^S \ldots, X_n^S$.

In step 206, a measure of central tendency ($E_1 \ldots, E_p$) is taken for each row of the sorted two-dimensional table 204. In some embodiments, the measure of central tendency is an average. In such embodiments, the average value across each row is taken as illustrated in FIG. 2A. That means that, for a given row in the sorted two-dimensional table 204, each element in the row is averaged together to form a value E as illustrated in FIG. 2A. In various embodiments, the measure of central tendency taken across each row of the sorted two-dimensional table 204 is a geometric mean, an arithmetic mean, median or mode of a collection of cellular constituent abundance values in the plurality of training microarray datasets.

In step 208, the measure of central tendency for each row, and the identity of each row is stored as standardization data structure 64. In this standardization data structure, the identity of each is the cellular constituent abundance ranking of the two-dimensional table 204. Thus, for example, in the first row of the standardization data structure 64 of FIG. 2A, the identity is 1, which means that the corresponding measure of central tendency is the measure of central tendency for the most abundant cellular constituent in each of the training microarray datasets 48 (in those embodiments where step 204 involves ranking from most abundant to least abundant cellular constituent in each training microarray datasets 46).

Once the standardization data structure 64 has been constructed it can be used to standardize test microarray datasets 66 as illustrated in FIGS. 2C and 2D. FIGS. 2C and 2D illustrate a method in which each measure of central tendency in the standardization data structure is for a set of cellular constituent abundance values where each cellular constituent abundance value in the set is the cellular constituent abundance value of a cellular constituent from a different training microarray dataset in the plurality of training microarray datasets that has the same ranking. The identifier $(I_1, \ldots, I_p)$ for each cellular constituent abundance value in the standardization data structure is the cellular constituent abundance value ranking of the cellular constituent in the training microarray datasets. In the method, the standardization data structure is applied to the abundance values of each cellular constituent in the test microarray dataset. For a given cellular constituent in the test microarray dataset having an abundance value x, this applying comprises transforming the abundance value x for the cellular constituent to the cellular constituent abundance value y in the standardized test microarray dataset by (i) determining a rank of the abundance value x for the cellular constituent in a ranking of the first plurality of cellular constituents in the test microarray dataset. Then, the cellular constituent abundance is assigned the value y in the standardized test microarray dataset, where y is the value of central tendency in the values of central tendency in the standardization data structure that has the same rank as the rank of the abundance value x.

In FIG. 2C, for example, at step 250 there is a test microarray dataset 66 ($T_1$) that is to be standardized. At step 252, the cellular constituent abundance values in the test microarray dataset 66 are ranked in the same manner that training microarray datasets 46 were ranked in step 204 of FIG. 2A, to provide a sorted test microarray dataset ($T_1^S$). Once ranked in this manner, the ranking of the individual cellular constituent abundances 68 within the test microarray dataset 66 serve as an index into the standardization data structure 64. For example, the $10^{th}$ most abundant cellular constituent abundance in the test microarray dataset 66 has the index "10" (in those embodiments in which the dataset is ranked from most abundant to least abundant in step 252) and is thus equated to the $10^{th}$ value in the standardization data structure 64. In step 254, each respective cellular constituent abundance value 68 in the test microarray dataset 66 is replaced with the value in the standardization data structure 64 that has the same index as the respective cellular constituent abundance value 68. For example, the $1^{st}$ ranked cellular constituent abundance value in the test microarray dataset 66 is replaced with the $1^{st}$ ranked value in the standardization data structure 64, the $2^{nd}$ ranked cellular constituent abundance value in the test microarray dataset 66 is replaced with the $2^{nd}$ ranked value in the standardization data structure 64, and so forth thereby creating the standardized test microarray dataset 70 ($T_1^N$) with standardized values 72. In the approach illustrated in FIG. 2, the test microarray dataset 66 must have the same number of cellular constituents as the training microarray datasets 48 so that, when the cellular constituent abundance values 68 of the test microarray dataset 66 are ranked, their ranking serves as an exact index into standardization data structure 64 in the manner described above.

FIG. 2D provides an illustration of the standardization method of FIG. 2C. In step 250 of FIG. 2D, a test microarray dataset 66 having cellular constituent abundance values 68 $\{eg_1, eg_2, eg_3, eg_4, eg_5, eg_7, \ldots, eg_p\}$ is obtained. In step 254, the cellular constituent abundance values 68 of the test microarray dataset 66 are ranked based on their abundance values such that the order of the cellular constituent abundance values is now $\{eg_1, eg_2, eg_3, eg_4, eg_5, eg_7, \ldots, eg_p\}$. In step 254, ranked cellular constituent abundance values 68 are replaced with the value having the same index from the standardization data structure 64. For example, $eg_2$ (ranked first in step 252 of FIG. 2D) is replaced with the first value in the standardization data structure 64 ($E_1$), $eg_6$ (ranked second in step 252 of FIG. 2D) is replaced with the second value in the standardization data structure 64 ($E_2$), $eg_3$ (ranked third in step 252 of FIG. 2D) is replaced with the third value in the standardization data structure ($E_3$) and so forth thereby constructing, in step 254, the standardization test microarray dataset 70 ($T_1^N$) with standardized values 70, which corresponds to the test microarray dataset 66.

Another method for constructing a standardization data structure 64 is disclosed in FIG. 3.

Step 302.

A plurality of training microarray datasets 46 is received. In some embodiments, the plurality of training microarray datasets 46 comprise microarray datasets for at least one phenotypic characterization, at least two different phenotypic characterizations, at least three different phenotypic characterizations, at least four different phenotypic characterizations, or at least five different phenotypic characterizations, at least ten different phenotypic characterizations, at least fifty different phenotypic characterizations, at least five hundred different phenotypic characterizations, at least one thousand different phenotypic characterizations, at least ten thousand different phenotypic characterizations, or between ten and one thousand phenotypic characterizations.

In some embodiments, one or more phenotypic characterizations represented by one or more training microarray datasets 46 in the plurality of training microarray datasets 46 is a tissue type or an organ type. As used herein, the term "represented" means that the training microarray dataset consists of cellular constituent abundance measurements of a biological specimen that either has the phenotypic characterization or is from a subject that has the phenotypic characterization. Exemplary tissue or organ types include, but are not limited to, bone, bladder, epithelial tissue, endothelial tissue, heart, skeletal muscle, white adipose, breast, blood, urine, mucosal fluid, bone marrow, lung, soft tissue, ovary, prostate, kidney, liver, thyroid gland, pancreas, endometrium, skin, stomach, myometrium, tonsil, rectum, brain, omentum, lymph node, cervix, colon, embryo, gut, hair root, muscle, placenta, eye, testicle, cervix, esophagus, cartilage, spleen, neuroendocrine cancers, normal tissue, sarcomas, and tumors.

In some embodiments, each phenotypic characterization represented by one or more training microarray datasets 46 in the plurality of training microarray datasets is a cell type. In some embodiments, this cell type is, for example, a cell type listed in Section 5.2.

In some embodiments, one or more phenotypic characterizations represented by one or more training microarray datasets 46 in the plurality of training microarray datasets 46 is a cell morphology. Examples of cell morphology include, but are not limited to, cell shape, cell surface area, changes in the spacing and proximity between cells, pathologic grade, pathologic stage, cell histology, and properties of multi-cellular colonies such as their shape, size and cell locations.

In some embodiments, one or more phenotypic characterizations represented by one or more training microarray datasets 46 in the plurality of training microarray datasets 46 is a disease state. In some embodiments, this disease state is, for example, an absence, presence, or stage of a disease listed in Section 5.3. In some embodiments, one or more phenotypic characterizations represented by one or more training microarray datasets 46 in the plurality of training microarray datasets 46 is an abnormal phenotypic characterization (e.g., an abnormal state in a tissue or organ, an abnormal cell type, an abnormal cell morphology, a disease state). In some embodiments, a phenotypic characterization is a drug response. In one example, some specimens used to construct the training microarray datasets 46 are obtained from specimens that have a positive response to a first drug and some specimens used to construct the training microarray datasets 46 are obtained from specimens that do not have a positive response to a first drug.

Step 304.

In step 304 each respective training microarray dataset 46 is standardized by dividing each cellular constituent abundance value in the respective training microarray dataset by a measure of central tendency for all the cellular constituent abundance values in the respective training microarray dataset. The measure of central tendency can be, for example, a geometric mean, an arithmetic mean, median or mode of all of the cellular constituent abundance values 48 in the respective training microarray dataset 46.

Step 306.

In typical embodiments, each of the training microarray datasets 46 contain abundance values for the same cellular constituents. It is possible that some training microarray datasets 46 do not have abundance values for all of these cellular constituents. In step 306, the plurality of cellular constituents represented by the training microarray datasets 46 in the training microarray dataset data store 44 are divided into a plurality of abundance bins based on the measured abundance values for the cellular constituents in the training microarray datasets 46. Each of the abundance bins represents a different abundance value range exhibited by the plurality of cellular constituents in the plurality of training microarray datasets 46. In some embodiments, the plurality of abundance bins is between 3 and 50 abundance bins, between 3 and 40 abundance bins, between 3 and 30 abundance bins, or between 3 and 15 abundance bins. In some embodiments, a measure of central tendency is determined for each cellular constituent for which abundance data is available in training microarray dataset data store 44 across the training microarray datasets 46 in the data store. Cellular constituents in the plurality of cellular constituents are then ranked. Then each cellular constituent is assigned to one abundance bin in a plurality of abundance bins based on the ranked measure of central tendency for the cellular constituent.

The measure of central tendency for a given cellular constituent can be, for example, a geometric mean, an arithmetic mean, median or mode of the given cellular constituent abundance value 48 across the training microarray datasets 46 in the training microarray dataset data store 44. In some embodiments, a first range of measured abundance values of cellular constituents in a first abundance bin in the plurality of abundance bins overlaps a second range of measured abundance values of cellular constituents in a second abundance bin in the plurality of abundance bins. In some embodiments, a first range of measured abundance values of cellular constituents in a first abundance bin in the plurality of abundance bins does not overlap a second range of measured abundance values of cellular constituents in a second abundance bin in the plurality of abundance bins.

In some embodiments, each abundance bin in the plurality of abundance bins is assigned cellular constituents in an abundance value range that does not overlap the abundance value range of any other abundance bin in the plurality of abundance bins. In some embodiments, the abundance value range for each abundance bin in the plurality of abundance bins is chosen so that approximately equal numbers of cellular constituents are assigned to each of the abundance bins based on cellular constituent abundance values.

Step 308.

In step 308, a measure of variability is computed for each cellular constituent in the plurality of cellular constituents for which abundance data is available in the training microarray dataset data store 44. In some embodiments, the measure of variability computed for each respective cellular constituent is based upon a coefficient of variation of cellular constituent abundance of the respective cellular constituent across the training microarray datasets 46 in training microarray dataset data store 44. Examples of measures of variability of the abundance value for a given cellular constituent across the training microarray datasets 46 include, but are not limited to, standard deviation, variance, range, and interquartile range of the abundance value of the cellular constituent across the training microarray datasets 46.

Step 308 does not require that there be a cellular constituent abundance value for a given cellular constituent in each of the training microarray datasets. A measure of variability of the abundance value for a given cellular constituent is computed based upon those training microarray datasets 46 in which there was an abundance value for the given cellular constituent.

Step 310.

Step 308 designated, for each respective abundance bin in the plurality of abundance bins, a predetermined number of cellular constituents in the respective abundance bin having the lowest abundance variability (as compared to the variability of the other cellular constituents in the respective abundance bin) to be part of a candidate standardization data structure. For example, in one embodiment, the fifty cellular constituents in each abundance bin having the lowest measure of cellular constituent abundance variability are designated to be part of a candidate standardization data structure 64. In some embodiments, the predetermined number is 2, 3, 4, 5, 6, 7, 8, 9, 10, or more than 10 cellular constituents. In some embodiments, the predetermined number is 10 or more cellular constituents, 40 or more cellular constituents, or 100 or more cellular constituents. In some embodiments, the predetermined number is up to five percent of the cellular constituents in the respective abundance bin that have the lowest cellular constituent abundance variability (as compared to the remaining cellular constituents in the respective abundance bin). In some embodiments, the predetermined number is up to ten percent, up to fifteen percent, up to twenty percent, or up to twenty-five percent of the cellular constituents in the respective abundance bin that have the lowest cellular constituent abundance variability (as compared to the remaining cellular constituents in the respective abundance bin).

Step 312.

In step 312, a reference value for each respective cellular constituent in the candidate reference data structure 64 is calculated as a measure of central tendency of that cellular constituent across the training microarray datasets 46 in the training microarray dataset data store 44. The measure of central tendency for each respective cellular constituent can be, for example, a geometric mean, an arithmetic mean, a median or a mode of the abundance of each respective cellular constituent across the training microarray datasets in the training microarray dataset data store 44. Thus, consider the case in which the measure of central tendency is an average. Thus, in this case, the average of the abundance of cellular constituent 1 in the candidate standardization data structure 64 across the training microarray datasets 46 in the training microarray dataset data store 44 is computed, the average of the abundance of cellular constituent of cellular constituent 2 in the candidate standardization data structure 64 across the training microarray datasets 46 in the training microarray dataset data store is computed, and so forth until an average is been computed for each of the cellular constituents in the candidate standardization data structure 64.

Step 312 does not require that there be a cellular constituent abundance value for a given cellular constituent in each of the training microarray datasets 46 in the training microarray dataset data store 44. For example, an average for a given cellular constituent can simply be computed based upon those training microarray datasets 46 in which there is an abundance value for the given cellular constituent.

Step 314.

In step 314, a determination is made as to whether a previous instance of the candidate standardization data structure 64 has been computed. The first time steps 306 through 312 are performed (i.e., the first instance of steps 306 through 312), condition 314 will be 314—No and process control will shift to step 318 because a previous instance of the candidate standardization data structure 64 has not been computed. The second and later times steps 306 through 312 are performed, condition 314 will be 314—Yes and process control will shift to step 316 because a previous instance of the candidate standardization data structure 64 has been computed.

Steps 318-322.

In steps 318 through 322, each of the cellular constituent values in the training microarray datasets 46 in the training microarray dataset data store is transformed using a kernel transformation based upon the candidate standardization data structure 64 computed in the previous instance of steps 306-312 (i.e., the last time steps 306-312 were run). Typically, this is performed on a training microarray dataset 46 by training microarray dataset 46 basis. For example, in step 318, a training microarray dataset 46 is selected. In step 320, for each respective cellular constituent abundance value in the selected training microarray dataset, the respective cellular constituent abundance value is transformed using a kernel transformation based upon the candidate standardization data structure 64.

In one embodiment, the kernel transformation transforms a cellular constituent abundance value x in the training microarray dataset to the cellular constituent abundance value y by the formula:

$$y = \frac{\sum_{j=0}^{m-1} w_j \cdot (t_j + s \cdot (x - h_j))}{\sum_{j=0}^{m-1} w_j}$$

where j is an index to a set of values M of cardinality m of cellular constituent abundance values in the candidate standardization data structure having values within a threshold value w of x;

$t_j$ is a value of central tendency, for a cellular constituent j, in the set of values M that is stored in the candidate standardization data structure 64;

$h_j$ is a cellular constituent abundance value for the cellular constituent j in the training microarray dataset selected in step 318;

$$w_j \text{ is } 1 - \left|\frac{x - h_j}{w}\right|^p;$$

w is the kernel function half-width (e.g., 1.5);
p is the kernel function parameter (e.g. 1); and $$s = \frac{t_{max} - t_{min}}{x_{max} - x_{min}}$$

$t_{max}$=the median value of a highest portion of the cellular constituent abundance values in the candidate standardization data structure;

$t_{min}$=the median value of a lowest portion of the cellular constituent abundance values in the candidate standardization data structure;

$x_{max}$=the median value of the cellular constituents in the training microarray dataset selected in step 318 that are the same as the cellular constituents that form the highest portion of the cellular constituent abundance values in the candidate standardization data structure; and $x_{min}$=the median value of the cellular constituents in the training microarray dataset selected in step 318 that are the same as the cellular constituents that form the lowest portion of the cellular constituent abundance values in the candidate standardization data structure.

In some embodiments, the highest portion of the cellular constituent abundance values in the candidate standardization data structure is the highest q quantile of cellular constituent abundance values in the candidate standardization data structure, where the q quantile is expressed on the 0 to 1 scale. In some embodiments, the lowest portion of the cellular constituent abundance values in the candidate standardization data structure is the lowest q quantile of cellular constituent abundance values in the candidate standardization data structure, where the q quantile is between 0 and 1. For example, in one embodiment, q is 0.1 and, therefore, the highest g quantile of cellular constituent abundance central tendency values in the candidate standardization data structure are the cellular constituent abundance values that are in the upper ten percent, in terms of the cellular constituent abundance central tendency values, in the candidate standardization data structure, and the lowest q quantile of cellular constituent abundance central tendency values in the candidate standardization data structure are the cellular constituent abundance values that are in the lower ten percent, in terms of the cellular constituent abundance central tendency values, in the candidate standardization data structure.

The kernel transformation for a given cellular constituent abundance value x is illustrated in FIG. 6. In FIG. 6, each $t_i$ is the cellular constituent abundance measure of central tendency for a cellular constituent j, in the set M that is stored in the standardization data structure and $w_i$ are weights assigned to each $t_i$. Further, each $s_i$ is a smoothed target value computed in the manner described below. In some embodiments w is between 0.1 and 2.0. In one embodiment, w is 1.5. In some embodiments, p is between 0.1 and 3.0. In one embodiment p is 1. In some embodiments $t_j$ is an average cellular constituent abundance value, for a cellular constituent j, in the set of values M that is stored in the candidate standardization data structure 64.

This kernel transformation is performed for each cellular constituent in the microarray datasets selected in the last instance of step 318. In step 322, a determination is made as to whether each of the training microarray datasets 46 in the training microarray dataset data store 44 have been normalized. If not (322—No), control passes to step 318 where an additional microarray is selected. If so, (322—Yes), control passes to step 306 and loop 306-316 is repeated.

Step 316.

Loop 306-316 is repeated until the percent similarity between the cellular constituents in the new candidate data structure and the previous candidate data structure is deemed above a threshold value. Step 316 determines whether the percent similarity between the cellular constituents in the new candidate data structure and the previous candidate data structure is deemed above a threshold value. In some embodiments, this threshold value is at least sixty percent, at least seventy percent, at least eighty percent, at least ninety percent, at least ninety-five percent, at least ninety-nine percent or at least 100 percent.

In some embodiments, the threshold value is ninety percent. This means that at least ninety percent of the cellular constituents in the standardization data structure 64 after the last iteration of loop 306-316 are found in the standardization data structure 64 computed by the iteration of loop 306-316 that was run just prior to the last iteration of loop 306-316. In some embodiments, the threshold value is eighty percent.

In some embodiments, a percent similarity between the identity of the cellular constituents in the last candidate standardization data structure and the identity of the cellular constituents in a previous instance of the candidate standardization data structure is deemed above a threshold value when there are less than one hundred cellular constituents in the candidate standardization data structure that are not in a previous instance of the candidate standardization data structure.

In some embodiments, a percent similarity between the identity of the cellular constituents in the last candidate standardization data structure and the identity of the cellular constituents in a previous instance of the candidate standardization data structure is deemed above a threshold value when there are less than fifty cellular constituents in the candidate standardization data structure that are not in a previous instance of the candidate standardization data structure.

In some embodiments, a percent similarity between the identity of the cellular constituents in the last candidate standardization data structure and the identity of the cellular constituents in a previous instance of the candidate standardization data structure is deemed above a threshold value when there are less than five cellular constituents in the candidate standardization data structure that are not in a previous instance of the candidate standardization data structure.

In some embodiments, a percent similarity between the identity of the cellular constituents in the last candidate standardization data structure and the identity of the cellular constituents in a previous instance of the candidate standardization data structure is deemed above a threshold value when loop 306-316 (consisting of steps 306-322 as needed) have been repeated two or more times, three or more times, four or more times, or five or more times.

Steps 322-330.

Once the percent similarity between the new candidate standardization data structure and the previous data structure is deemed above a threshold (316—Yes), process control ultimately passes to step 328 where the standardization data structure 64 is outputted to a user interface device, a monitor, a computer-readable storage medium, a computer-readable memory, or a local or remote computer system; or the standardization data structure 64 is displayed. As illustrated in Step 330, the standardization data structure 64 comprises an identity ($I_1 \ldots, I_p$), and for each identity, a standardized value ($E_1 \ldots E_p$). In the standardization data structure 64 produced by the method of FIGS. 3A-3B, each identity is the identity of a cellular constituent. For each respective cellular constituent identity in the standardization data structure 64, there is a corresponding standardization value for the respective cellular constituent that is a measure of central tendency of the cellular constituent across all of the training microarray datasets 46 in the training microarray dataset data store.

Once the standardization data structure 64 has been constructed it can be used to standardize test microarray datasets 66 as illustrated in FIG. 3C. FIG. 3C illustrates a method of standardizing a test microarray dataset 66 ($T_1$), where the test microarray dataset comprises abundance values 68 (e) for a plurality of cellular constituents ($G_1 \ldots, G_p$). In the method, a standardization data structure 64 is applied to each of the abundance values in the test microarray dataset thereby computing a standardized test microarray dataset 70 ($T_1^N$), containing standardized abundance values (E). Here, the standardization data structure 64 comprises a plurality of values of central tendency ($E_1 \ldots, E_p$) and a cellular constituent identifier ($I_1 \ldots I_p$) for each respective value of central tendency. The plurality of values of central tendency is derived from the training microarray datasets using the method described above in conjunction with FIGS. 3A and 3B. Advantageously, there is no requirement that the test microarray dataset be included in the training microarray datasets that were used to construct the standardize data structure 64.

In the embodiment illustrated in FIG. 3C, the application of the standardization data structure to an abundance value in the test microarray dataset comprises transforming the abundance value x for the cellular constituent in the test microarray dataset to the cellular constituent abundance value y in the standardized test microarray dataset by the formula:

$$y = \frac{\sum_{j=0}^{m-1} w_j \cdot (t_j + s \cdot (x - h_j))}{\sum_{j=0}^{m-1} w_j}$$

where j is an index to a set of values M of cardinality m of central tendency in the standardization data structure having values within a threshold value w of x;

$t_j$ is a value of central tendency, for a cellular constituent j, in the set M that is stored in the standardization data structure;

$h_j$ is a cellular constituent abundance value for the cellular constituent j in the test microarray dataset;

$$w_j \text{ is } 1 - \left|\frac{x - h_j}{w}\right|^p;$$

w is the kernel function half-width;
p is the kernel function parameter;
s is an average slope of the kernel function;

$$s = \frac{t_{max} - t_{min}}{x_{max} - x_{min}};$$

$t_{max}$=the median value of a highest portion of the plurality of values of central tendency in the standardization data structure;

$t_{min}$=the median value of a lowest portion of the plurality of values of central tendency in the standardization data structure;

$x_{max}$=the median value of the cellular constituents in the plurality of cellular constituents of the test microarray dataset that are the same as the cellular constituents that form the highest portion of the plurality of values of central tendency in the standardization data structure; and $x_{min}$=the median value of the cellular constituents in the plurality of cellular constituents of the test microarray dataset that are the same as the cellular constituents that form the lowest portion of the plurality of values of central tendency in the standardization data structure.

In some embodiments, the highest portion of the plurality of values of central tendency is the highest q quantile of the plurality of values of central tendency and the lowest portion of the plurality of values of central tendency is the lowest q quantile of the plurality of values of central tendency in the standardization data structure, where q is between 0 and 1 (e.g., 0.1, meaning that the top 10 percent and bottom 10 percent are used).

Once the standardization data structure 64 has been applied to each of the abundance values in the test microarray dataset using the kernel transformation described above, the standardized test microarray dataset is outputted to a user interface device, a monitor, a computer-readable storage medium, a computer-readable memory, or a local or remote computer system, or the standardized test microarray dataset is displayed. In some embodiments, the test microarray dataset is received from a remote source over a wide area network and the standardized test microarray dataset is communicated to the remote source over the wide area network.

Smoothing.

While the cellular constituents in the standardized data structure 64 are expected to have approximately constant expression across tissues both healthy and diseased, it is conceivable that under some abnormal biological circumstances a test microarray dataset 66 from a specimen will have a small number of cellular constituents whose expression levels differ significantly from the reference values for these cellular constituents set forth in the standardization data structure 64. In some embodiments, only a certain percentage of the cellular constituents in the test microarray that correspond to the cellular constituents in the standardized test microarray dataset are used in the kernel transformation. In some embodiments, housekeeping cellular constituents are removed from an input chip in the following manner:

1) for each i=0, . . . , N−1, where N is the number of cellular constituents in the standardization data structure 64, compute $y_i$ using the formula given above excluding $h_i$ itself from the input set H of cellular constituents in the target microarray dataset to be standardized;

2) compute standard deviation σ of values $y_i$−$t_j$ (where $t_j$ is the standardization data structure value corresponding to $y_j$), where $y_i$ is the formula given above; and 3) remove cellular constituents $h_i$ from H if σ exceeds a predetermined values such as 1, 2, 3, etc.

5.2 Exemplary Cell Types

In some embodiments, a phenotypic characterization is a cell type. Exemplary cell types include, but are not limited to, keratinizing epithelial cells such as epidermal keratinocytes (differentiating epidermal cells), epidermal basal cells (stem cells), keratinocytes of fingernails and toenails, nail bed basal cells (stem cells), medullary hair shaft cells, cortical hair shaft cells, cuticular hair shaft cells, cuticular hair root sheath cells, hair root sheath cells of Huxley's layer, hair root sheath cell of Henle's layer, external hair root sheath cells, hair matrix cells (stem cells).

Exemplary cell types further include, but are not limited to, wet stratified barrier epithelial cells such as surface epithelial cells of stratified squamous epithelium of cornea, tongue, oral cavity, esophagus, anal canal, distal urethra and vagina, basal cells (stem cell) of epithelia of cornea, tongue, oral cavity, esophagus, anal canal, distal urethra and vagina, and urinary epithelium cells (lining urinary bladder and urinary ducts).

Exemplary cell types further include, but are not limited to, exocrine secretory epithelial cells such as salivary gland mucous cells (polysaccharide-rich secretion), salivary gland serous cells (glycoprotein enzyme-rich secretion), Von Ebner's gland cells in tongue (washes taste buds), mammary gland cells (milk secretion), lacrimal gland cells (tear secretion), Ceruminous gland cells in ear (wax secretion), Eccrine sweat gland dark cells (glycoprotein secretion), Eccrine sweat gland clear cells (small molecule secretion), Apocrine sweat gland cells (odoriferous secretion, sex-hormone sensitive), Gland of Moll cells in eyelid (specialized sweat gland), Sebaceous gland cells (lipid-rich sebum secretion) Bowman's gland cells in nose (washes olfactory epithelium), Brunner's gland cells in duodenum (enzymes and alkaline mucus), seminal vesicle cells (secretes seminal fluid components, including fructose for swimming sperm), prostate gland cells (secretes seminal fluid components), Bulbourethral gland cells (mucus secretion), Bartholin's gland cells (vaginal lubricant secretion), gland of Littre cells (mucus secretion), Uterus endometrium cells (carbohydrate secretion), isolated goblet cells of respiratory and digestive tracts (mucus secretion), stomach lining mucous cells (mucus secretion), gastric gland zymogenic cells (pepsinogen secretion), gastric gland oxyntic cells (hydrochloric acid secretion), pancreatic acinar cells (bicarbonate and digestive enzyme secretion), Paneth cells of small intestine (lysozyme secretion), type II pneumocytes of lung (surfactant secretion), and Clara cells of lung.

Exemplary cell types further include, but are not limited to, hormone secreting cells such as anterior pituitary cells (somatotropes, lactotropes, thyrotropes, gonadotropes, corticotropes), intermediate pituitary cells (secreting melanocyte-stimulating hormone), magnocellular neurosecretory cells (secreting oxytocin, secreting vasopressin), gut and respiratory tract cells secreting serotonin (secreting endorphin, secreting somatostatin, secreting gastrin, secreting secretin, secreting cholecystokinin, secreting insulin, secreting glucagons, secreting bombesin), thyroid gland cells (thyroid epithelial cells, parafollicular cells), parathyroid gland cells (parathyroid chief cells, oxyphil cells), adrenal gland cells (chromaffin cells, secreting steroid hormones), Leydig cells of testes secreting testosterone, Theca interna cells of ovarian follicle secreting estrogen, Corpus luteum cells of ruptured ovarian follicle secreting progesterone, kidney juxtaglomerular apparatus cells (renin secretion), macula densa cells of kidney, peripolar cells of kidney, and mesangial cells of kidney.

Exemplary cell types further include, but are not limited to, gut, exocrine glands and urogenital tract cells such as intestinal brush border cells (with microvilli), exocrine gland striated duct cells, gall bladder epithelial cells, kidney proximal tubule brush border cells, kidney distal tubule cells, ductulus efferens nonciliated cells, epididymal principal cells, and epididymal basal cells.

Exemplary cell types further include, but are not limited to, metabolism and storage cells such as hepatocytes (liver cells), white fat cells, brown fat cells, and liver lipocytes. Exemplary cell types further include, but are not limited to, barrier function cells (lung, gut, exocrine glands and urogenital tract) such as type I pneumocytes (lining air space of lung), pancreatic duct cells (centroacinar cell), nonstriated duct cells (of sweat gland, salivary gland, mammary gland, etc.), kidney glomerulus parietal cells, kidney glomerulus podocytes, loop of Henle thin segment cells (in kidney), kidney collecting duct cells, and duct cells (of seminal vesicle, prostate gland, etc.).

Exemplary cell types further include, but are not limited to, epithelial cells lining closed internal body cavities such as blood vessel and lymphatic vascular endothelial fenestrated cells, blood vessel and lymphatic vascular endothelial continuous cells, blood vessel and lymphatic vascular endothelial splenic cells, synovial cells (lining joint cavities, hyaluronic acid secretion), serosal cells (lining peritoneal, pleural, and pericardial cavities), squamous cells (lining perilymphatic space of ear), squamous cells (lining endolymphatic space of ear), columnar cells of endolymphatic sac with microvilli (lining endolymphatic space of ear), columnar cells of endolymphatic sac without microvilli (lining endolymphatic space of ear), dark cells (lining endolymphatic space of ear), vestibular membrane cells (lining endolymphatic space of ear), stria vascularis basal cells (lining endolymphatic space of ear), stria vascularis marginal cells (lining endolymphatic space of ear), cells of Claudius (lining endolymphatic space of ear), cells of Boettcher (lining endolymphatic space of ear), Choroid plexus cells (cerebrospinal fluid secretion), pia-arachnoid squamous cells, pigmented ciliary epithelium cells of eye, nonpigmented ciliary epithelium cells of eye, and corneal endothelial cells Exemplary cell types further include, but are not limited to, ciliated cells with propulsive function such as respiratory tract ciliated cells, oviduct ciliated cells (in female), uterine endometrial ciliated cells (in female), rete testis ciliated cells (in male), ductulus efferens ciliated cells (in male), and ciliated ependymal cells of central nervous system (lining brain cavities).

Exemplary cell types further include, but are not limited to, extracellular matrix secretion cells such as ameloblast epithelial cells (tooth enamel secretion), planum semilunatum epithelial cells of vestibular apparatus of ear (proteoglycan secretion), organ of Corti interdental epithelial cells (secreting tectorial membrane covering hair cells) loose connective tissue fibroblasts, corneal fibroblasts, tendon fibroblasts, bone marrow reticular tissue fibroblasts, pericytes, nucleus pulposus cells of intervertebral disc, cementoblast/cementocytes (tooth root bonelike cementum secretion), odontoblast/odontocyte (tooth dentin secretion), hyaline cartilage chondrocytes fibrocartilage chondrocytes, elastic cartilage chondrocytes, osteoblasts/osteocytes, osteoprogenitor cells (stem cell of osteoblasts), hyalocyte of vitreous body of eye, and stellate cells of perilymphatic space of ear.

Exemplary cell types further include, but are not limited to, contractile cells such as red skeletal muscle cells (slow), white skeletal muscle cells (fast), intermediate skeletal muscle cells, nuclear bag cells of Muscle spindle, nuclear chain cells of Muscle spindle, satellite cells (stem cell), ordinary heart muscle cells, nodal heart muscle cells, purkinje fiber cells, smooth muscle cells (various types), myoepithelial cells of iris, myoepithelial cells of exocrine glands, and red blood cells.

Exemplary cell types further include, but are not limited to, blood and immune system cells such as erythrocytes (red blood cell), megakaryocytes (platelet precursor), monocytes, connective tissue macrophages (various types), epidermal Langerhans cells, osteoclasts (in bone), dendritic cells (in lymphoid tissues), microglial cells (in central nervous system), neutrophil granulocytes, eosinophil granulocytes, basophil granulocytes, mast cells, helper T cells, suppressor T cells, cytotoxic T cells, B cells, natural killer cells, and reticulocytes.

Exemplary cell types further include, but are not limited to, sensory transducer cells such as auditory inner hair cells of organ of Corti, auditory outer hair cells of organ of Corti, basal cells of olfactory epithelium (stem cell for olfactory neurons), cold-sensitive primary sensory neurons, heat-sensitive primary sensory neurons, merkel cell of epidermis (touch sensor), olfactory receptor neurons, photoreceptor rod cell of eyes, photoreceptor blue-sensitive cone cells of eye, photoreceptor green-sensitive cone cells of eye, photoreceptor red-sensitive cone cells of eye, type I carotid body cells (blood pH sensor), Type II carotid body cells (blood pH sensor), type I hair cells of vestibular apparatus of ear (acceleration and gravity), type II hair cells of vestibular apparatus of ear (acceleration and gravity), and type I taste bud cells.

Exemplary cell types further include, but are not limited to, autonomic neuron cells such as cholinergic neural cells, adrenergic neural cells, and peptidergic neural cells. Exemplary cell types further include, but are not limited to, sense organ and peripheral neuron supporting cells such as inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, type I taste bud supporting cells, olfactory epithelium supporting cells, Schwann cells, satellite cells (encapsulating peripheral nerve cell bodies), and enteric glial cells.

Exemplary cell types further include, but are not limited to, central nervous system neurons and glial cells such as astrocytes, neuron cells, oligodendrocytes, and spindle neurons. Exemplary cell types further include, but are not limited to, lens cells such as anterior lens epithelial cells, crystallin-containing lens fiber cells, and karan cells. Exemplary cell types further include, but are not limited to, pigment cells such as melanocytes and retinal pigmented epithelial cells. Exemplary cell types further include, but are not limited to, IC germ cells such as oogoniums/oocytes, spermatids, spermatocytes, spermatogonium cells, (stem cell for spermatocyte), and spermatozoon. Exemplary cell types further include, but are not limited to, nurse cells such as ovarian follicle cells, sertoli cells (in testis), and thymus epithelial cells. For more reference on cell types see Freitas Jr., 1999, *Nanomedicine*, Volume I: Basic Capabilities, Landes Bioscience, Georgetown, Tex.

5.3 Exemplary Disease States

Some embodiments of the present invention contain training and/or test microarray datasets for one or more phenotypic characterizations, where the phenotypic characterization is disease state. As used herein, the term "disease state" refers to the absence, presence, or stage of disease in a biological specimen and or a subject from which the biological specimen was obtained. Exemplary diseases include, but are not limited to, asthma, ataxia telangiectasia (Jaspers and Bootsma, 1982, *Proc. Natl. Acad. Sci. U.S.A.* 79: 2641), bipolar disorder, a cancer, common late-onset Alzheimer's disease, diabetes, heart disease, hereditary early-onset Alzheimer's disease (George-Hyslop et al., 1990, *Nature* 347: 194), hereditary nonpolyposis colon cancer, hypertension, infection, maturity-onset diabetes of the young (Barbosa et al., 1976, *Diabete Metab.* 2: 160), mellitus, migraine, nonalcoholic fatty liver (NAFL) (Younossi, et al., 2002, Hepatology 35, 746-752), nonalcoholic steatohepatitis (NASH) (James & Day, 1998, *J. Hepatol.* 29: 495-501), non-insulin-dependent diabetes mellitus, obesity, polycystic kidney disease (Reeders et al., 1987, *Human Genetics* 76: 348), psoriases, schizophrenia, steatohepatitis and xeroderma pigmentosum (De Weerd-Kastelein, *Nat. New Biol.* 238: 80). Genetic heterogeneity hampers genetic mapping, because a chromosomal region may cosegregate with a disease in some families but not in others.

Auto-immune and immune disease states include, but are not limited to, Addison's disease, ankylosing spondylitis, antiphospholipid syndrome, Barth syndrome, Graves' Disease, hemolytic anemia, IgA nephropathy, lupus erythematosus, microscopic polyangiitis, multiple sclerosis, myasthenia gravis, myositis, osteoporosis, pemphigus, psoriasis, rheumatoid arthritis, sarcoidosis, scleroderma, and Sjogren's syndrome. Cardiology disease states include, but are not limited to, arrhythmia, cardiomyopathy, coronary artery disease, angina pectoris, and pericarditis.

Cancers addressed by the systems and the methods of the present invention include, but are not limited to, sarcoma or carcinoma. Examples of such cancers include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, and heavy chain disease.

5.4 Exemplary Preprocessing Routines

Optionally, a number of different preprocessing routines can be performed by preprocessing module 60 to prepare training microarray datasets 46 for use in the methods disclosed above in conjunction with FIGS. 2 and 3. Although not shown in FIG. 1B, such exemplary preprocessing techniques could be performed on test microarray datasets 66 prior to application of the standardized test data structure 64 to the test microarray datasets 66. Some such preprocessing protocols are described in this section. Typically, the preprocessing comprises normalizing the cellular constituent abundance measurement of each cellular constituent in a plurality of cellular constituents that is measured in a biological sample. Many of the preprocessing protocols described in this section are used to normalize microarray data and are therefore called normalization protocols. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA). In some embodiments, any of the protocols described in this section are used in addition to, or instead of, the normalization disclosed in step 304 of FIG. 3.

One normalization protocol is Z-score of intensity. In this protocol, cellular constituent abundance values are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij} = (I_{ij} - mnI_i)/sdI_i,$$

and $$Zdiff_j(x,y) = Z\text{-score}_{xj} - Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $$Im_{ij} = (I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $$Im_{ij} = \log(1.0 + (I_{ij}/\text{median}I_i)).$$

Yet another normalization protocol is the Z-score standard deviation log of intensity protocol. In this protocol, raw expression intensities are normalized by the mean log intensity ($mnLI_i$) and standard deviation log intensity ($sdLI_1$). For microarray data, the mean log intensity and the standard deviation log intensity is computed for the log of raw intensity of control genes. Then, the Z-score intensity $Z \log S_{ij}$ for probe i and spot j is:

$$Z \log S_{ij} = (\log(I_{ij}) - mnLI_i)/sdLI_i.$$

Still another normalization protocol is the Z-score mean absolute deviation of log intensity protocol. In this protocol, raw intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity $mnLI_i$ and the mean absolute deviation log intensity $madLI_i$ are computed for the log of raw intensity of control genes. Then, the Z-score intensity Z log $A_{ij}$ for probe i and spot j is:

$$Z \log A_{ij} = (\log(I_{ij}) - mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

An intensity dependent normalization can be implemented in R, a language and environment for statistical computing and graphics. In a specific embodiment, the normalization method uses a lowess( ) scatter plot smoother that can be applied to all or a subgroup of probes on the array. For a description of lowess( ), see, e.g., Becker et al., "The New S Language," *Wadsworth and Brooks/Cole* (S version),1988; Ripley, 1996, *Pattern Recognition and Neural Networks*, Cambridge University Press; and Cleveland, 1979, *J. Amer. Statist. Assoc.* 74, 829:836, each of which is hereby incorporated by reference in its entirety.

5.5 Transcriptional State Measurements

This section provides some exemplary methods for measuring the expression level of gene products, which are one type of cellular constituent. One of skill in the art will appreciate that this invention is not limited to the following specific measurement methods.

5.5.1 Transcript Assay Using Microarrays

The techniques described in this section are particularly useful for the determination of the expression state or the transcriptional state of a cell or cell type or any other biological sample. These techniques include the provision of polynucleotide probe arrays that can be used to provide simultaneous determination of the expression levels of a plurality of genes. These techniques further provide methods for designing and making such polynucleotide probe arrays.

The expression level of a nucleotide sequence of a gene can be measured by any high throughput techniques. However measured, the result is either the absolute or relative amounts of transcripts or response data, including but not limited to, values representing abundances or abundance ratios. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

As used herein, a microarray is an array of positionally-addressable binding (e.g., hybridization) sites on a support. In a preferred embodiment, the sites are for binding to many of the nucleotide sequences encoded by the genome of a cell or organism, preferably most or almost all of the transcripts of genes or to transcripts of more than half of the genes having an open reading frame in the genome. In a preferred embodiment, each of such binding sites consists of polynucleotide probes bound to the predetermined region on the support. Microarrays can be made in a number of ways, of which several are described herein below. However produced, preferably microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between 1 $cm^2$ and 25 $cm^2$, preferably 1 to 3 $cm^2$. However, both larger and smaller arrays (e.g., nanoarrays) are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 $cm^2$ or higher. In some embodiments, a microarray can have at least 550 different probes per 1 $cm^2$, at least 1,000 different probes per 1 $cm^2$, at least 1,500 probes different per 1 $cm^2$ or at least 2,000 different probes per 1 $cm^2$. In some embodiments, the microarray is a high density array, preferably having a density of at least 2,500 different probes per 1 $cm^2$. A microarray can contain at least 2,500, at least 5,000, at least 10,000, at least 15,000, at least 20,000, at least 25,000, at least 50,000 or at least 55,000 different (e.g., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, a microarray can comprise binding sites for products encoded by fewer than 50% of the genes in the genome of an organism. Alternatively, a microarray can have binding sites for the products encoded by at least 50%, at least 75%, at least 85%, at least 90%, at least 95%, at least 99% or 100% of the genes in the genome of an organism. In other embodiments, a microarray can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. In some embodiments, the profiling arrays comprise one probe specific to each target gene or exon. However, if desired, the profiling arrays can contain at least 2, 5, 10, 100, or 1000 or more probes specific to some target genes or exons.

5.5.1.1 Preparing Probes for Microarrays

As noted above, the "probe" to which a particular polynucleotide molecule, such as an exon, specifically hybridizes is a complementary polynucleotide sequence. Preferably one or more probes are selected for each target exon. For example, when a minimum number of probes are to be used for the detection of an exon, the probes normally comprise nucleotide sequences greater than 40 bases in length. Alternatively, when a large set of redundant probes is to be used for an exon, the probes normally comprise nucleotide sequences of 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

In some embodiments, the probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (e.g., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between 15 and 600 bases in length, more typically between 20 and 100 bases, most preferably between 40 and 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; and U.S. Pat. No. 5,539,083).

In alternative embodiments, the hybridization sites (e.g., the probes) are made from plasmid or phage clones of genes, cDNAs (e.g., expressed sequence tags), or inserts therefrom (Nguyen et al., 1995, *Genomics* 29:207-209).

5.5.1.2 Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

One method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al, 1996, *Genome Res.* 6:639-645; and Schena et al., 1995, *Proc. Natl. Acad. Sci. U.S.A.* 93:10539-11286).

A second method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used.

In one embodiment, microarrays are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays can be synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3N end of the polynucleotide. Alternatively, polynucleotide probes can be attached to the surface covalently at the 5N end of the polynucleotide (see for example, Blanchard, 1998, in *Synthetic DNA Arrays in Genetic Engineering*, Vol. 20, J. K. Setlow, Ed., Plenum Press, New York at pages 111-123).

5.5.1.3 Target Polynucleotide Molecules

Target polynucleotides that can be analyzed include RNA molecules such as, but by no means limited to, messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides that can also be analyzed by the methods of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules can be naturally occurring nucleic acid molecules such as genomic or extragenoinic DNA molecules isolated from a patient, or RNA molecules, such as mRNA molecules, isolated from a patient. Alternatively, the polynucleotide molecules can be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In spme embodiments, the target polynucleotides will correspond to particular genes or to particular gene transcripts (e.g., to particular mRNA sequences expressed in cells or to particular cDNA sequences derived from such mRNA sequences). However, in many embodiments, the target polynucleotides can correspond to particular fragments of a gene transcript. For example, the target polynucleotides may correspond to different exons of the same gene, e.g., so that different splice variants of the gene can be detected and/or analyzed.

In some embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In some embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. Pat. Nos. 6,271,002, and 7,229,765. Both oligo-dT primers (U.S. Pat. Nos. 5,545,522 and 6,132,997) or random primers (U.S. Pat. No. 7,229,765) that contain an RNA polymerase promoter or complement thereof can be used. The target polynucleotides can be short and/or fragmented polynucleotide molecules that are representative of the original nucleic acid population of the cell.

The target polynucleotides to be analyzed are typically detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

In some instances, the detectable label is a fluorescent label, e.g., by incorporation of nucleotide analogs. Other labels suitable for use include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Some radioactive isotopes include, but are not limited to, $^{32}$P, $^{35}$S, $^{14}$C, $^{15}$N and $^{125}$I. Fluorescent molecules include, but are not limited to, fluorescein and its derivatives, rhodamine and its derivatives, texas red, 5Ncarboxy-fluorescein ("FMA"), 2N,7N-dimethoxy-4N,5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41. Fluorescent molecules further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable, but are not limited to, ferritin, hemocyanin, and colloidal gold. Alternatively, in some embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.5.1.4 Hybridization to Microarrays

As described supra, nucleic acid hybridization and wash conditions are chosen so that the polynucleotide molecules to be analyzed (referred to herein as the "target polynucleotide molecules) specifically bind or specifically hybridize to the complementary polynucleotide sequences of the array, preferably to a specific array site, where its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (e.g., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization with Nucleic Acid Probes*, Elsevier Science Publishers B.V. and Kricka, 1992, Nonisotopic DNA Probe Techniques, Academic Press, San Diego, Calif.

Exemplary hybridization conditions for use with the screening and/or signaling chips include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.5.1.5 Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal.

When fluorescently labeled probes are used, the fluorescence emissions at each site of a transcript array can be, preferably, detected by scanning confocal laser microscopy. In one embodiment, a separate scan, using the appropriate excitation line, is carried out for each of two fluorophores used in such embodiments. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In some embodiments, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, can be used to monitor mRNA abundance levels at a large number of sites simultaneously.

Signals are recorded and, in a preferred embodiment, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors can be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

5.6 Apparatus, Computer and Computer Program Product Implementations

The present invention can be implemented as a computer program product that comprises a computer program mechanism embedded in a computer-readable storage medium. Further, any of the methods of the present invention can be implemented in one or more computers or other forms of apparatus. Examples of apparatus include but are not limited to, a computer, and a spectroscopic measuring device (e.g., a microarray reader or microarray scanner). Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer program product that contains any or all of the program modules shown in FIG. 1A and/or FIG. 1B. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

5.7 EXEMPLARY EMBODIMENTS

Provided hereinbelow are nonlimiting examples in accordance with various aspects of the present invention.

Embodiment 1

A method of standardizing a dataset from a test microarray experiment (hereinafter "test microarray dataset"), wherein the test microarray dataset comprises an abundance value for each cellular constituent in a first plurality of cellular constituents, the method comprising:

(A) applying a standardization data structure to an abundance value of each cellular constituent in the first plurality of cellular constituents, thereby computing a standardized test microarray dataset, wherein the standardization data structure comprises a plurality of values of central tendency and, for each respective value of central tendency in the plurality of values of central tendency, an identifier, wherein each value of central tendency in the plurality of values of central tendency is a measure of central tendency of cellular constituent abundance values in a plurality of training microarray datasets, wherein each training microarray dataset in the plurality of training microarray datasets comprises abundance values for a second plurality of cellular constituents (in some embodiments the second plurality of cellular constituents is a subset of the first plurality of cellular constituent; in some embodiments the first plurality of cellular constituents is identical to the second plurality of cellular constituents; in some embodiments at least 10, at least 20, at least 40, at least 50, at least 100, or at least five hundred cellular constituents are found in both the first plurality of cellular constituents and the second plurality of cellular constituents; in some embodiments there are no cellular constituents in the first plurality of cellular constituents in the second plurality of cellular constituents; in preferred embodiments the test and training microarrays contain binding sites for cellular constituents of the same species); and the test microarray dataset is not included in the plurality of training microarray datasets; and (B) optionally outputting the standardized test microarray dataset to a user interface device, a monitor, a computer-readable storage medium, a computer-readable memory, or a local or remote computer system; or displaying the standardized test microarray dataset.

Embodiment 2

The method of embodiment 1, wherein each training microarray dataset in the plurality of training microarray datasets is for a different specimen in a plurality of specimens.

Embodiment 3

The method of embodiments 1 or 2, wherein the plurality of training microarray datasets comprises microarray datasets for at least four different phenotypic characterizations.

Embodiment 4

The method of embodiments 1 or 2, wherein the plurality of training microarray datasets comprises microarray datasets for at least five different phenotypic characterizations.

Embodiment 5

The method of embodiments 1 or 2, wherein the plurality of training microarray datasets comprises microarray datasets for at least ten different phenotypic characterizations.

Embodiment 6

The method of embodiments 1 or 2, wherein the plurality of training microarray datasets comprises microarray datasets for at least fifty different phenotypic characterizations.

Embodiment 7

The method of embodiments 1 or 2, wherein the plurality of training microarray datasets comprises microarray datasets for at least five hundred different phenotypic characterizations.

Embodiment 8

The method of embodiment 4, wherein a phenotypic characterization in the at least five different phenotypic characterizations is a tissue type or an organ type.

Embodiment 9

The method of embodiment 4, wherein a phenotypic characterization in the at least five different phenotypic characterizations is a cell type.

Embodiment 10

The method of embodiment 4, wherein a phenotypic characterization in the at least five different phenotypic characterizations is a cell morphology.

Embodiment 11

The method of embodiment 4, wherein a phenotypic characterization in the at least five different phenotypic characterizations is a disease state.

Embodiment 12

The method of any one of embodiments 1 through 11, wherein a training microarray dataset in the plurality of training microarray datasets is for an abnormal phenotypic characterization.

Embodiment 13

The method of embodiment 12, wherein the abnormal phenotypic characterization is an abnormal state in a tissue or organ.

Embodiment 14

The method of embodiment 12, wherein the abnormal phenotypic characterization is an abnormal cell type.

Embodiment 15

The method of embodiment 12, wherein the abnormal phenotypic characterization is an abnormal cell morphology.

Embodiment 16

The method of embodiment 12, wherein the abnormal phenotypic characterization is a disease state.

Embodiment 17

The method of embodiment 4, wherein, for each respective phenotypic characterization in the at least five different phenotypic characterizations, the plurality of training microarray datasets comprises at least ten different microarray datasets for the respective phenotypic characterization.

Embodiment 18

The method of embodiment 4, wherein, for each respective phenotypic characterization in the at least five different phenotypic characterizations, the plurality of training microarray datasets comprises at least one hundred different microarray datasets for the respective phenotypic characterization.

Embodiment 19

The method of any one of embodiments 1 through 18, wherein a cellular constituent in said first plurality of cellular constituents is a gene, a protein, a peptide, a proteoglycan, a glycoprotein, a lipoprotein, a carbohydrate, a lipid, an mRNA, a cDNA, an oligonucleotide, a microRNA, a tRNA, or a protein with a selected modification.

Embodiment 20

The method of any one of embodiments 1 through 19, wherein a cellular constituent in said second plurality of cellular constituents is a gene, a protein, a peptide, a proteoglycan, a glycoprotein, a lipoprotein, a carbohydrate, a lipid, an mRNA, a cDNA, an oligonucleotide, a microRNA, a tRNA, or a protein with a selected modification.

Embodiment 21

The method of any one of embodiments 1 through 20, wherein the test microarray dataset is measured from a microarray comprising probes arranged with a density of 100 different probes per 1 $cm^2$ or higher.

Embodiment 22

The method of any one of embodiments 1 through 20, wherein the test microarray dataset is measured from a microarray comprising probes arranged with a density of at least 2,500 different probes per 1 $cm^2$.

Embodiment 23

The method of any one of embodiments 1 through 22, wherein the test microarray dataset is measured from a microarray wherein the microarray probes on the microarray consist of at least 10,000 different probes.

Embodiment 24

The method of any one of embodiments 1 through 23, wherein the test microarray dataset or a training microarray dataset is measured from an expression microarray, a comparative genomic hybridization microarray, an exon microarray, or a microRNA microarray.

Embodiment 25

The method of any one of embodiments 1 through 24, wherein a training microarray dataset in the plurality of training microarray datasets is measured from a microarray comprising probes arranged with a density of 100 different probes per 1 $cm^2$ or higher.

Embodiment 26

The method of any one of embodiments 1 through 24, wherein a training microarray dataset in the plurality of training microarray datasets is measured from a microarray comprising probes arranged with a density of at least 2,500 different probes per 1 $cm^2$.

Embodiment 27

The method of any one of embodiments 1 through 26, wherein a training microarray dataset in the plurality of training microarray datasets is measured from a microarray comprising at least 10,000 different probes.

Embodiment 28

The method of any one of embodiments 1 through 27, wherein a value of central tendency in said plurality of values of central tendency is a geometric mean, an arithmetic mean, median or mode.

Embodiment 29

The method of embodiment 28, wherein each respective value of central tendency in said plurality of values of central tendency is a value of central tendency of a respective collection of cellular constituent abundance values, wherein each cellular constituent abundance value in the respective collection of cellular constituent values is the cellular constituent abundance of the same cellular constituent from a different training microarray dataset in said plurality of training microarray datasets, and the identifier for said value of central tendency is an identity of said cellular constituent.

Embodiment 30

The method of embodiment 28, wherein each respective value of central tendency in said plurality of values of central tendency is a value of central tendency of a respective collection of cellular constituent abundance values, and wherein each cellular constituent abundance value in the respective collection of cellular constituent abundance values is the cellular constituent abundance value for a cellular constituent from a different training microarray dataset in said plurality of training microarray datasets having the same cellular constituent abundance value ranking in the different training microarray dataset and wherein the identifier for said value of central tendency is the cellular constituent abundance value ranking, wherein the test microarray dataset and each of the training microarray datasets consists of data for the same cellular constituents and wherein there are data for at least forty cellular constituents, at least forty-five cellular constituents, at least fifty cellular constituents, at least sixty cellular constituents, at least seventy cellular constituents, at least 100 cellular constituents in the test microarray dataset and each of the training microarray datasets.

Embodiment 31

The method of any one of embodiments 1 through 30, wherein the oligonucleotide probes on the test microarray consist of between 1,000 and $5\times10^6$ different oligonucleotides.

Embodiment 32

The method of any one of embodiments 1 through 30, wherein the first plurality of cellular constituents is between 1,000 and 50,000 mRNAs.

Embodiment 33

The method of any one of embodiments 1 through 30, wherein the first plurality of cellular constituents is between 50 and 200,000 proteins.

Embodiment 34

The method of any one of embodiments 1 through 33, wherein the plurality of values of central tendency is between 25 and 50,000 values of central tendency.

Embodiment 35

The method of any one of embodiments 1 through 34, wherein the plurality of training microarray datasets is between 50 and 20,000 training microarray datasets.

Embodiment 36

The method of any one of embodiments 1 through 35, wherein the second plurality of cellular constituents is between 25 and 50,000 cellular constituents.

Embodiment 37

The method of any one of embodiments 1 through 36, wherein the second plurality of cellular constituents is a subset of the cellular constituents measured in microarray experiments giving rise to said plurality of training microarray datasets.

Embodiment 38

The method of any one of embodiments 1 through 37, wherein each respective value of central tendency in said plurality of values of central tendency is for a cellular constituent in the second plurality of cellular constituents, wherein each respective value of central tendency in said plurality of values of central tendency is a value of central tendency of a respective collection of cellular constituent abundance values for a cellular constituent in the second plurality of cellular constituents, wherein each cellular constituent abundance value in the respective collection of cellular constituent abundance values is for the same cellular constituent from a different training microarray dataset in the plurality of training microarray datasets.

Embodiment 39

The method embodiment 38, wherein the method further comprises identifying said second plurality of cellular constituents by a method comprising:

(i) standardizing, for each respective training microarray dataset in the plurality of training microarray datasets, the respective training microarray dataset by dividing each cellular constituent abundance value in the respective training microarray dataset by a measure of central tendency for all of the cellular constituent abundance values in the respective training microarray dataset;

(ii) dividing a third plurality of cellular constituents that is in each of the plurality of training microarray datasets into a plurality of abundance bins based on the measured abundance values for the third plurality of cellular constituents in the plurality of training microarray datasets, wherein each abundance bin represents an abundance value range exhibited by the third plurality of cellular constituents in the plurality of training microarray datasets;

(iii) computing a measure of variability for each respective cellular constituent in the third plurality of cellular constituents across the plurality of training microarray datasets;

(iv) designating, for each respective abundance bin in the plurality of abundance bins, a predetermined number of cellular constituents in the respective abundance bin having the lowest cellular constituent abundance variability in the plurality of training microarray datasets, relative to all other cellular constituents in the respective abundance bin, to be part of a candidate standardization data structure;

(v) calculating a training value for each respective cellular constituent in the candidate standardization data structure, wherein the training value for the respective cellular constituent is a measure of central tendency of an abundance of the respective cellular constituent across the plurality of training microarray datasets;

(vi) transforming each cellular constituent abundance value in a training microarray dataset in the training microarray datasets using a kernel transformation based upon the training microarray dataset;

(vii) repeating the transforming step (vi) until cellular constituent abundance values in each training microarray dataset in the plurality of training microarray datasets have been transformed; and (viii) repeating steps (ii) through (vii), using the transformed values produced by step (vi) and the repetition of step (vi) as set forth in step (vii), until a percent similarity between the identity of the cellular constituents in the candidate standardization data structure and the identity of the cellular constituents in a previous instance of the candidate standardization data structure is deemed above a threshold value, wherein the cellular constituents in the candidate standardization data structure at a time when the percent similarity between the identity of the cellular constituents in the candidate standardization data structure and the identity of the cellular constituents in a previous instance of the candidate standardization data structure is deemed above a threshold value is deemed to be said second plurality of cellular constituents.

Embodiment 40

The method of embodiment 39, wherein a first range of measured abundance values of cellular constituents in a first abundance bin in the plurality of abundance bins overlaps a second range of measured abundance values of cellular constituents in a second abundance bin in the plurality of abundance bins.

Embodiment 41

The method of embodiment 39, wherein a first range of measured abundance values of cellular constituents in a first abundance bin in the plurality of abundance bins does not overlap a second range of measured abundance values of cellular constituents in a second abundance bin in the plurality of abundance bins.

Embodiment 42

The method of any one of embodiments 39 through 41, wherein the threshold value is ninety percent.

Embodiment 43

The method of any one of embodiments 39 through 41, wherein the threshold value is eighty percent.

Embodiment 44

The method of any one of embodiments 39 through 43, wherein the candidate standardization data structure comprises at least two hundred cellular constituents, and wherein a percent similarity between the identity of the cellular constituents in the candidate standardization data structure and the identity of the cellular constituents in a previous instance of the candidate standardization data structure is deemed above a threshold value when there are less than one hundred cellular constituents in the candidate standardization data structure that are not in a previous instance of the candidate standardization data structure.

Embodiment 45

The method of any one of embodiments 39 through 43, wherein the candidate standardization data structure comprises at least two hundred cellular constituents, and wherein a percent similarity between the identity of the cellular constituents in the candidate standardization data structure and the identity of the cellular constituents in a previous instance of the candidate standardization data structure is deemed above a threshold value when there are less than fifty cellular constituents in the candidate standardization data structure that are not in a previous instance of the candidate standardization data structure.

Embodiment 46

The method of any one of embodiments 39 through 43, wherein the candidate standardization data structure comprises at least two hundred cellular constituents, and wherein a percent similarity between the identity of the cellular constituents in the candidate standardization data structure and the identity of the cellular constituents in a previous instance of the candidate standardization data structure is deemed above a threshold value when there are less than five cellular constituents in the candidate standardization data structure that are not in a previous instance of the candidate standardization data structure.

Embodiment 47

The method of any one of embodiments 39 through 43, wherein a percent similarity between the identity of the cellular constituents in the candidate standardization data structure and the identity of the cellular constituents in a previous instance of the candidate standardization data structure is deemed above a threshold value when steps (ii) through (vii) have been repeated five or more times.

Embodiment 48

The method of any one of embodiments 39 through 43, wherein a percent similarity between the identity of the cellular constituents in the candidate standardization data structure and the identity of the cellular constituents in a previous instance of the candidate standardization data structure is deemed above a threshold value when steps (ii) through (vii) have been repeated one or more times.

Embodiment 49

The method of any one of embodiments 39 through 48, wherein the measure of central tendency in step (i) is the median of cellular constituent abundance values in the respective training microarray dataset.

Embodiment 50

The method of any one of embodiments 39 through 49, wherein the plurality of abundance bins in step (ii) is between 3 and 15 abundance bins.

Embodiment 51

The method of any one of embodiments 39 through 50, wherein the measure of variability computed for each respective cellular constituent in step (iii) is based upon a coefficient of variation of cellular constituent abundance value of the respective cellular constituent across the plurality of training microarray datasets.

Embodiment 52

The method of any one of embodiments 39 through 51, wherein the predetermined number in step (iv) is 10 or more cellular constituents.

Embodiment 53

The method of any one of embodiments 39 through 51, wherein the predetermined number in step (iv) is 40 or more cellular constituents.

Embodiment 54

The method of any one of embodiments 39 through 53, wherein the measure of central tendency computed for a respective cellular constituent in step (v) is the arithmetic mean of the abundance values for the respective cellular constituent across the plurality of training microarray datasets.

Embodiment 55

The method of any one of embodiments 39 through 54, wherein the kernel transformation transforms a cellular constituent abundance value x in the training microarray dataset to the cellular constituent abundance value y by the formula:

$$y = \frac{\sum_{j=0}^{m-1} w_j \cdot (t_j + s \cdot (x - h_j))}{\sum_{j=0}^{m-1} w_j}$$

wherein
j is an index to a set of values M of cardinality m of central tendency in the standardization data structure having values within a threshold value w of x;
$t_j$ is a cellular constituent abundance value of central tendency, for a cellular constituent j, in the set of values M that is stored in the standardization data structure;

$h_j$ is a cellular constituent abundance value for the cellular constituent j in the training microarray dataset;

$$w_j \text{ is } 1 - \left|\frac{x - h_j}{w}\right|^p;$$

w is the kernel function half-width;
p is the kernel function parameter; and
s is an average slope of the kernel function.

Embodiment 56

The method of embodiment 55, wherein $$s = \frac{t_{max} - t_{min}}{x_{max} - x_{min}}$$

wherein
$t_{max}$=the median value of a highest portion of said plurality of values of central tendency;
$t_{min}$=the median value of a lowest portion of said plurality of values of central tendency;
$x_{max}$=the median value of the cellular constituents in the training microarray dataset that are the same as the cellular constituents that form the highest portion of said plurality of values of central tendency;
$x_{min}$=the median value of the cellular constituents in the training microarray dataset that are the same as the cellular constituents that form the lowest portion of said plurality of values of central tendency.

Embodiment 57

The method of embodiment 56 wherein
the highest portion of said plurality of values of central tendency is the highest q quantile of said plurality of values of central tendency; and
the lowest portion of said plurality of values of central tendency is the lowest q quantile of said plurality of values of central tendency,
wherein the q quantile is expressed on the 0 to 1 scale.

Embodiment 58

The method of embodiment 56, wherein outlier values of central tendency are removed from m prior to computation of y.

Embodiment 59

The method of embodiment 1, wherein each respective value of central tendency in said plurality of values of central tendency is an arithmetic mean of a respective collection of cellular constituent abundance values, wherein a cellular constituent abundance of each cellular constituent in the respective collection of cellular constituent abundance values has the same cellular constituent abundance ranking in all of the training microarray datasets in the plurality of training microarray datasets.

Embodiment 60

The method of embodiment 59, wherein a cellular constituent abundance value of a first cellular constituent and a cellular constituent abundance value of a second cellular constituent are used in a value of central tendency in the plurality of values of central tendency and wherein an identity of the first cellular constituent is different from an identity of the second cellular constituent.

Embodiment 61

The method of embodiment 59, wherein a cellular constituent abundance value of a first cellular constituent and a cellular constituent abundance value of a second cellular constituent are used in a value of central tendency in the plurality of values of central tendency and wherein an identity of the first cellular constituent is the same as an identity of the second cellular constituent.

Embodiment 62

The method of any one of embodiments 59 through 61, the method further comprising, for each respective training microarray dataset in the plurality of training microarray datasets, before the applying step (A), ranking, the cellular constituents in the training microarray dataset by cellular constituent abundance.

Embodiment 63

The method of any one of embodiment 1 through 58, wherein
each respective value of central tendency in said plurality of values of central tendency is an arithmetic mean of a respective collection of cellular constituent abundance values for a cellular constituent in the second plurality of cellular constituents, wherein each cellular constituent abundance value in the respective collection of cellular constituent abundance values is for the same cellular constituent from a different training microarray dataset in the plurality of training microarray datasets; and wherein
said applying step (A) comprises transforming an abundance value x for a cellular constituent in the first plurality of cellular constituents in the test microarray dataset to the cellular constituent abundance value y in the standardized test microarray dataset by the formula:

$$y = \frac{\sum_{j=0}^{m-1} w_j \cdot (t_j + s \cdot (x - h_j))}{\sum_{j=0}^{m-1} w_j}$$

wherein
j is an index to a set of values M of cardinality m of central tendency in the standardization data structure having values within a threshold value w of x;
$t_j$ is a value of central tendency, for a cellular constituent j, in the set M that is stored in the standardization data structure;
$h_j$ is a cellular constituent abundance value for the cellular constituent j in the first plurality of cellular constituents of the test microarray dataset;

$$w_j \text{ is } 1 - \left|\frac{x - h_j}{w}\right|^p;$$

w is the kernel function half-width;
p is the kernel function parameter; and
s is an average slope of the kernel function.

Embodiment 64

The method of embodiment 63, wherein $$s = \frac{t_{max} - t_{min}}{x_{max} - x_{min}}$$

wherein
$t_{max}$=the median value of a highest portion of said plurality of values of central tendency;
$t_{min}$=the median value of a lowest portion of said plurality of values of central tendency;
$x_{max}$=the median value of the cellular constituents in the first plurality of cellular constituents of the test microarray dataset that are the same as the cellular constituents that form the highest portion of said plurality of values of central tendency; and
$x_{min}$=the median value of the cellular constituents in the first plurality of cellular constituents of the test microarray dataset that are the same as the cellular constituents that form the lowest portion of said plurality of values of central tendency.

Embodiment 65

The method of embodiment 64 wherein
the highest portion of said plurality of values of central tendency is the highest q quantile of said plurality of values of central tendency; and
the lowest portion of said plurality of values of central tendency is the lowest q quantile of said plurality of values of central tendency,
wherein q is between 0 and 1.

Embodiment 66

The method of embodiment 1 or any one of embodiments 59-63, wherein
each respective value of central tendency in said plurality of values of central tendency is an arithmetic mean of a respective collection of cellular constituent abundance values, wherein a cellular constituent abundance of each cellular constituent in the respective collection of cellular constituent abundance values has the same cellular constituent abundance ranking in all of the training microarray datasets in the plurality of training microarray datasets; and wherein
said applying step (A) comprises transforming an abundance value x for a cellular constituent in the first plurality of cellular constituents in the test microarray dataset to the cellular constituent abundance value y in the standardized test microarray dataset by the method comprising:
(i) determining a rank of the abundance value x for the cellular constituent in a ranking of the first plurality of cellular constituents in the test microarray dataset; and
(ii) assigning the cellular constituent abundance value y in the standardized test microarray dataset the value of central tendency in said plurality of values of central tendency that has the same rank as the rank of the abundance value x for the cellular constituent in the ranking of the first plurality of cellular constituents.

Embodiment 67

The method of any one of embodiments 1 through 66 wherein the test microarray dataset is received from a remote source over a wide area network and wherein the standardized test microarray dataset is communicated to the remote source over said wide area network.

Embodiment 68

The method of any one of embodiments 1 through 67, wherein the first plurality of cellular constituents is greater than a number of cellular constituents in a training microarray dataset in the plurality of training microarray datasets.

Embodiment 69

The method of any one of embodiments 1 through 67, wherein the first plurality of cellular constituents is equal to a number of cellular constituents in a training microarray dataset in the plurality of training microarray datasets.

Embodiment 70

The method of any one of embodiments 1 through 67, wherein the first plurality of cellular constituents is less than a number of cellular constituents in a training microarray dataset in the plurality of training microarray datasets.

Embodiment 71

A computer-readable medium storing a computer program executable by a computer to standardizing a dataset from a test microarray experiment (hereinafter "test microarray dataset"), wherein the test microarray dataset comprises an abundance value for each cellular constituent in a first plurality of cellular constituents, the computer program comprising:
(A) computer executable instructions for applying a standardization data structure to an abundance value of each cellular constituent in the first plurality of cellular constituents, thereby computing a standardized test microarray dataset, wherein
the standardization data structure comprises a plurality of values of central tendency and, for each respective value of central tendency in the plurality of values of central tendency, an identifier; wherein each value of central tendency in the plurality of values of central tendency is a measure of central tendency of cellular constituent abundance values in a plurality of training microarray datasets, wherein each training microarray dataset in the plurality of training microarray datasets comprises abundance values for a second plurality of cellular constituents; and
the test microarray dataset is not included in the plurality of training microarray datasets; and, optionally,
(B) computer executable instructions for outputting the standardized test microarray dataset to a user interface device, a monitor, a computer-readable storage medium, a computer-readable memory, or a local or remote computer system; or displaying the standardized test microarray dataset.

Embodiment 72

The computer-readable medium of embodiment 71, wherein the plurality of training microarray datasets comprises microarray datasets for at least five different phenotypic characterizations.

Embodiment 73

An apparatus for standardizing a dataset from a test microarray experiment (hereinafter "test microarray dataset"), wherein the test microarray dataset comprises an abundance value for each cellular constituent in a first plurality of cellular constituents, the apparatus comprising:

a processor; and a memory, coupled to the processor, the memory storing a module comprising:

(A) computer executable instructions for applying a standardization data structure to an abundance value of each cellular constituent in the first plurality of cellular constituents, thereby computing a standardized test microarray dataset, wherein the standardization data structure comprises a plurality of values of central tendency and, for each respective value of central tendency in the plurality of values of central tendency, an identifier; wherein each value of central tendency in the plurality of values of central tendency is a measure of central tendency of cellular constituent abundance values in a plurality of training microarray datasets, wherein each training microarray dataset in the plurality of training microarray datasets comprises abundance values for a second plurality of cellular constituents; and the test microarray dataset is not included in the plurality of training microarray datasets; and, optionally, (B) computer executable instructions for outputting the standardized test microarray dataset to a user interface device, a monitor, a computer-readable storage medium, a computer-readable memory, or a local or remote computer system; or displaying the standardized test microarray dataset.

Embodiment 74

The apparatus of embodiment 73, wherein the plurality of training microarray datasets comprises microarray datasets for at least five different phenotypic characterizations.

Embodiment 75

The apparatus of embodiment 73 or 74, wherein the apparatus is in electrical communication with a wide area network and wherein the test microarray dataset is received from a remote computer over said wide area network.

Embodiment 76

The apparatus of embodiment 73 or 74, wherein the apparatus is in electrical communication with a wide area network and wherein the computer executable instructions for outputting the standardized test microarray dataset comprise communicating the standardized test microarray dataset to a remote computer system across said wide area network.

Embodiment 77

The apparatus of embodiment 73 or 74, wherein the apparatus is a computer.

Embodiment 78

A computer-readable medium storing a computer program executable by a computer, the computer program comprising instructions for carrying out the method of any one of embodiments 1 through 70.

Embodiment 79

A computer system comprising a processor and a memory, the memory storing instructions for using the processor to carry out the method of any one of embodiments 1 through 70.

6 EXAMPLES

Example 1

Computing a Standardization Data Structure

Diagnostic tests based on DNA microarrays have emerged as a technology with a potential to revolutionize personalized medicine. One of the challenges on the path to widespread clinical adoption is a lack of reproducibility among microarray expression measurements conducted under varying experimental conditions. In this example, robust methods for standardization of the measurements are described. A total of 121 cellular constituents with stable abundance values over a broad range of cell types were identified, and used to convert raw microarray measurements to mutually comparable levels.

This example further demonstrates that the process provides the stability required for the development of reliable clinical diagnostic tests. In particular, methods for standardization of Affymetrix U133A specimens processed at multiple laboratories, based on the identification and transformation of housekeeping cellular constituent abundance measurements, are provided. The methods can be used to standardize a single microarray at a time. To demonstrate the validity of the standardization methods, the following was shown: (i) after the processing, the chosen housekeeping cellular constituents exhibited stable abundance levels, consistent with their role in maintaining cellular function across a very broad range of cell and tissue types and, (ii) the obscuring variation of expression values of marker cellular constituents used for classification of cancers did not affect the predictive power of a diagnostic test utilizing these markers.

The present example is based on the principle of transforming cellular constituent abundance values of each specimen such that the resulting housekeeping cellular constituent values are consistent with the values found for the same cellular constituents in the standardization data structure 64. In the present example, the standardization data structure 64 consisted of the 121 cellular constituents listed in Table 1 below with their associated reference values.

TABLE 1

Cellular Constituents in the Exemplary Standardization Data Structure

| Affymetrix Probeset Identifier | Unigene Identifier | Gene Description |
|---|---|---|
| 200061_s_a | Hs.356794 | ribosomal protein S24 |
| 200717_x_at | Hs.421257 | ribosomal protein L7 |
| 200829_x_at | Hs.500775 | zinc finger protein 207 |
| 200926_at | Hs.386384 | ribosomal protein S23 |
| 200933_x_at | Hs.446628 | ribosomal protein S4, X-linked |
| 201217_x_at | Hs.119598 | ribosomal protein L3 |
| 201244_s_at | Hs.159130 | v-raf-1 murine leukemia viral oncogene homolog 1 |
| 201254_x_at | Hs.408073 | ribosomal protein S6 |
| 201630_s_at | Hs.130873 | acid phosphatase 1, soluble |
| 201643_x_at | Hs.483486 | putative zinc finger protein |
| 201871_s_at | Hs.351296 | uba/ubx 33.3 kda protein. |
| 202135_s_at | Hs.98791 | centractin beta |
| 202292_x_at | Hs.533479 | lysophospholipase II |

TABLE 1-continued

Cellular Constituents in the Exemplary Standardization Data Structure

| Affymetrix Probeset Identifier | Unigene Identifier | Gene Description |
|---|---|---|
| 202360_at | Hs.484349 | mastermind homolog |
| 202513_s_at | Hs.533308 | protein phosphatase 2, regulatory subunit B (B56), delta isoform |
| 203107_x_at | Hs.551669 | ribosomal protein S2 |
| 203546_at | Hs.158497 | importin 13 |
| 203993_x_at | Hs.517331 | nuclear encoded mitochondrial protein, cDNA A2-YF5 |
| 204322_at | Hs.143600 | golgi phosphoprotein 4 |
| 204665_at | Hs.24808 | hypothetical protein FLJ21168 |
| 205189_s_at | Hs.494529 | Fanconi anemia, complementation group C |
| 206040_s_at | Hs.57732 | mitogen-activated protein kinase 11 |
| 206257_at | Hs.227782 | Coiled-coil domain containing 9 |
| 206406_at | Hs.111850 | mitochondrial capsule selenoprotein |
| 206431_x_at | Hs.155829 | KIAA0676 protein |
| 206559_x_at | Hs.549262 | eukaryotic translation elongation factor 1 alpha 1 |
| 206596_s_at | Hs.89606 | Neural retina leucine zipper |
| 206846_s_at | Hs.6764 | histone deacetylase 6 |
| 207035_at | Hs.467981 | solute carrier family 30 (zinc transporter), member 3 |
| 207466_at | Hs.278959 | galanin |
| 207683_at | Hs.198313 | forkhead box N1 |
| 207685_at | Hs.533322 | crystallin, beta B3 |
| 207780_at | Hs.3232 | Cylicin, basic protein of sperm head cytoskeleton 2 |
| 208234_x_at | Hs.533683 | FGF receptor |
| 208448_x_at | Hs.56303 | interferon, alpha 6 |
| 208494_at | Hs.241597 | solute carrier family 6 (neurotransmitter transporter, L-proline), member 7 |
| 208589_at | Hs.283104 | transient receptor potential cation channel, subfamily C, member 7 |
| 208904_s_at | Hs.153177 | ribosomal protein S28 |
| 209134_s_at | Hs.408073 | ribosomal protein S6 |
| 210391_at | — | |
| 210723_x_at | Hs.459927 | hypothetical protein MGC4771 |
| 211073_x_at | Hs.119598 | ribosomal protein L3 |
| 211201_at | Hs.1428 | follicle stimulating hormone receptor |
| 211345_x_at | Hs.444467 | collagen, type XIII, alpha 1 |
| 211486_s_at | Hs.161851 | potassium voltage-gated channel, KQT-like subfamily, member 2 |
| 211788_at | Hs.170835 | three prime repair exonuclease 2 |
| 211927_x_at | Hs.444467 | myosin, heavy polypeptide 9, non-muscle |
| 211975_at | Hs.436204 | zinc finger protein 289, ID1 regulated |
| 211982_x_at | Hs.460468 | exportin 6 |
| 212004_at | Hs.252967 | putative MAPK activating protein PM20,PM21 |
| 212100_s_at | Hs.360940 | polymerase (DNA-directed), delta interacting protein 3 |
| 212447_at | Hs.539472 | kelch repeat and BTB (POZ) domain containing 2 |
| 212986_s_at | Hs.445078 | tousled-like kinase 2 |
| 213360_s_at | Hs.520575 | nuclear pore membrane protein 121 kda |
| 213477_x_at | Hs.549262 | eukaryotic translation elongation factor 1 alpha 1 |
| 213583_at | Hs.549262 | eukaryotic translation elongation factor 1 alpha 1 |
| 213614_x_at | Hs.547129 | eukaryotic translation elongation factor 1 alpha 1 |
| 214003_x_at | Hs.8102 | ribosomal protein S20 |
| 214010_s_at | Hs.465475 | ATPase, Class II, type 9B |
| 214080_x_at | Hs.512640 | protein kinase C substrate 80K-H |
| 214127_s_at | Hs.111801 | arsenate resistance protein ARS2 |
| 214756_at | Hs.520575 | postmeiotic segregation increased 2-like 1 |
| 214824_at | — | zinc finger protein 204 |
| 215366_at | Hs.487648 | sorting nexin 13 |
| 215693_x_at | Hs.65234 | DEAD/H (Asp-Glu-Ala-Asp/His) box polypeptide 27 |
| 215766_at | Hs.446309 | glutathione S-transferase A1 |
| 215994_at | Hs.155829 | KIAA0676 protein |
| 216049_at | Hs.445030 | Rho-related BTB domain containing 3 |
| 216116_at | Hs.529198 | NCK interacting protein with SH3 domain |
| 216213_at | Hs.481181 | NIMA (never in mitosis gene a)-related kinase 1 |
| 216372_at | — | transketolase-like 1 |
| 216437_at | Hs.167805 | enhancer of polycomb 1 |
| 216671_x_at | Hs.553338 | mucin 8, tracheobronchial |
| 216726_at | Hs.447377 | VENT-like homeobox 2 pseudogene 1 |
| 216854_at | Hs.550500 | growth differentiation factor 11 |
| 216916_s_at | Hs.113287 | PSD-95/SAP90-binding protein 2 |
| 217029_at | Hs.159428 | apoptosis regulator bax, cytoplasmic isoform beta |
| 217108_at | — | putative dimethyladenosine transferase |
| 217442_at | Hs.365689 | immunoglobulin superfamily, member 4B |
| 217484_at | Hs.334019 | complement component (3b/4b) receptor 1, including Knops blood group system |
| 217740_x_at | Hs.499839 | ribosomal protein L7a |
| 217742_s_at | Hs.435610 | WW domain containing adaptor with coiled-coil |
| 217830_s_at | Hs.12865 | NSFL1 (p97) cofactor (p47) |
| 217928_s_at | Hs.503022 | similar to sit4 (sporulation-induced transcript 4) protein family, of yeast |
| 218020_s_at | Hs.36959 | testis expressed sequence 27 |
| 218089_at | Hs.11314 | protein c20orf4 (cgi-23) (pro0225). |
| 218159_at | Hs.471975 | chromosome 20 open reading frame 116 |
| 218216_x_at | Hs.103561 | ADP-ribosylation-like factor 6 interacting protein 4 |
| 218753_at | Hs.55024 | hypothetical protein FLJ10307 |
| 218912_at | Hs.521168 | GRIP and coiled-coil domain containing 1 |
| 219428_s_at | Hs.368717 | peroxisomal membrane protein 4, 24kDa |
| 219535_at | Hs.109437 | hormonally upregulated Neu-associated kinase |
| 219639_x_at | Hs.270244 | poly (ADP-ribose) polymerase family, member 6 |
| 220127_s_at | Hs.12439 | F-box and leucine-rich repeat protein 12 |
| 220531_at | — | hypothetical protein FLJ14126 |
| 220882_at | — | hypothetical protein PRO2964 |
| 220947_s_at | Hs.513498 | DKFZP434P1750 protein |
| 220957_at | Hs.406709 | cutaneous T-cell lymphoma-associated antigen 1 |
| 221199_at | Hs.302025 | GDNF family receptor alpha 4 |
| 221417_x_at | Hs.501561 | endothelial differentiation, sphingolipid G-protein-coupled receptor, 8 |
| 221784_at | Hs.442138 | widely-interspaced zinc finger motifs |
| 221817_at | Hs.21701 | dolichyl pyrophosphate phosphatase 1 |
| 221855_at | Hs.356460 | Homo sapiens, clone IMAGE:3626627, mRNA |
| 34846_at | Hs.351887 | calcium/calmodulin-dependent protein kinase (CaM kinase) II beta |
| 35685_at | — | ring finger protein 1 |
| 36004_at | Hs.43505 | inhibitor of kappa light polypeptide gene enhancer in B-cells, kinase gamma |
| 36129_at | Hs.513861 | RUN and TBC1 domain containing 1 |
| 36907_at | Hs.130607 | mevalonate kinase (mevalonic aciduria) |
| 38703_at | Hs.258551 | aspartyl aminopeptidase |
| 45526_g_at | Hs.513296 | hypothetical protein FLJ14154 |
| 45749_at | Hs.152717 | hypothetical protein FLJ13725 |
| 47608_at | Hs.520145 | tight junction protein 4 (peripheral) |
| 48612_at | Hs.511839 | Nedd4 binding protein 1 |
| 49327_at | Hs.19306 | likely ortholog of mouse synembryn |
| 49878_at | Hs.100915 | peroxisomal membrane protein pex16 (peroxin-16) |
| 56829_at | Hs.26814 | Tularik gene 1 |
| 65521_at | Hs.19196 | ubiquitin-conjugating enzyme HBUCE1 |
| 65635_at | Hs.29288 | endo-beta-N-acetylglucosaminidase |
| 77508_r_at | Hs.183075 | rabaptin, RAB GTPase binding effector protein 2 |
| 78047_s_at | Hs.5215 | integrin beta 4 binding protein |
| 79005_at | Hs.134074 | solute carrier family 35, member E1 |

The exemplary standardization data structure set forth in Table 1 was developed using a library of 5,539 specimens processed by twelve different laboratories using the Affymetrix U133A microarray. The specimens represent both normal and diseased tissue, including more than 200 different morphologies representing a broad range of tissue types and clinical and laboratory conditions likely to be encountered in diagnostic practice.

Table 2 below lists the sample sites that contributed microarrays, and the percentage of microarrays from each respective sample site that was used in the construction of the standardization data structure described in Table 1.

TABLE 2

Sample Sites Represented in Study

| Sample Site | Percentage |
|---|---|
| breast | 12.7 |
| blood/bone marrow | 12.0 |
| lung | 5.0 |
| soft tissues | 4.0 |
| ovary | 3.9 |
| epithelial cell | 3.1 |
| prostate | 3.0 |
| kidney | 3.0 |
| liver | 2.6 |
| thyroid gland | 2.6 |
| pancreas | 2.5 |
| endometrium | 2.4 |
| skin | 1.9 |
| stomach | 1.6 |
| Myometrium | 1.6 |
| tonsil | 1.6 |
| rectum | 1.5 |
| various cell lines | 1.4 |
| brain | 1.4 |
| omentum | 1.3 |
| lymph node | 2.2 |
| cervix | 1.2 |
| colon | 2.1 |
| esophagus | 1.0 |
| other | 24.4 |

The exemplary standardization methods were based on identification of a standardization data structure consisting of housekeeping cellular constituents and their reference abundance values. To illustrate the distinction between a housekeeping cellular constituent and a non-housekeeping cellular constituent, FIG. 4 shows raw cellular constituent abundance measurements ($\log_{10}$) for an exemplary gene housekeeping gene (FIG. 4A) and a non-housekeeping gene for each of the 5,539 specimens used in the present example. Each dot in FIGS. 4A and 4B represents the gene expression value of the single indicated gene for a single specimen. In particular, FIG. 4A illustrates the expression pattern for the housekeeping gene candidate (Affymetrix U133A ID 208589_at, gene symbol TRPC7, transient receptor potential cation channel) across 5,539 specimens. Vertical lines in FIG. 4A represent boundaries between processing laboratories. FIG. 4B illustrates the expression pattern for the non-housekeeping gene (Affymetrix U133A ID 202404_s_at, gene symbol COL1A2, collagen of skin, tendon and bone, alpha-2 chain) across the library of 5,539 specimens. As in FIG. 4A, vertical lines represent boundaries between processing laboratories.

To produce a standardization data structure 64, the method illustrated in FIGS. 3A and 3B was taken. What follows is how the steps identified in FIGS. 3A and 3B were performed in the instant example. The description of how the steps illustrated in FIGS. 3A and 3B in no way limits the ways in which the steps in FIGS. 3A and 3B could be performed in accordance with the instant invention.

Step 302.

A plurality of training microarray datasets was received. Here, the plurality of training microarray datasets was the 5,539 microarray datasets described in conjunction with Table 2 above, where each of the 5,539 microarray represent cellular constituent abundance measurements for a corresponding specimen in 5,539 specimen samples. The plurality of training microarray datasets comprises microarray datasets for at least five different phenotypic characterizations. Here, a phenotypic characterization is a tissue of origin (e.g., breast, blood/bone marrow, lung, soft tissue, ovary, etc.).

Step 304.

For each respective training microarray dataset in the 5,539 training microarray datasets, the respective training microarray dataset was standardized by dividing each cellular constituent abundance value in the respective training microarray dataset by a measure of central tendency for all the cellular constituent abundance values in the respective training microarray dataset. In the present example, the measure of central tendency that was used was the median of the expression values of all genes in the respective microarray training dataset. For example, each of the expression values of the first training microarray dataset in the 5,539 training microarray datasets was divided by the median expression value of all the expression values of the first training microarray dataset, each of the expression values of the second training microarray dataset in the 5,539 microarray training microarray datasets was divided by the median expression value of all the expression values of the second training microarray dataset, and so forth until each of the 5,539 training microarray datasets was normalized.

Step 306.

In step 306 the plurality of cellular constituents was divided into five abundance bins based on the measured abundance values for the cellular constituents in the training microarray datasets. Each of the five abundance bins represents a different abundance value range exhibited by the plurality of cellular constituents in the plurality of training microarray datasets.

Step 308.

In step 308, a measure of variability was computed for each cellular constituent in the plurality of cellular constituents across the 5,539 training microarray datasets. In this particular example, the measure of variability was the standard deviation of gene expression. Thus, the standard deviation of cellular constituent 1 across the 5,539 training microarray datasets was computed, the standard deviation of cellular constituent 2 across the 5,539 training microarray datasets was computed, and so forth until a standard deviation had been computed for each cellular constituent in the 5,539 training microarray datasets. Step 308 did not require that there be a cellular constituent abundance value for a given cellular constituent in each of the 5,539 training microarray datasets. A standard deviation for a given cellular constituent was simply computed based upon those training microarray datasets in which there was an abundance value for the given cellular constituent.

Step 310.

In step 310, fifty cellular constituents in each abundance bin having the lowest measure of variability were designated to be part of a candidate standardization data structure 64.

Step 312.

In step 312, the reference value for each respective cellular constituent in the candidate reference data structure was calculated as the average of the abundance of that cellular constituent across the 5,539 training microarray datasets. Thus, the average of the abundance of cellular constituent 1 in the candidate standardization data structure 64 across the 5,539 training microarray datasets was computed, the average of the abundance of the cellular constituent of cellular constituent 2 in the candidate standardization data structure 64 across the 5,539 training microarray datasets was computed, and so forth until an average had been computed for each of the 250 cellular constituents in the candidate standardization data structure 64. Step 312 did not require that there be a cellular constituent abundance value for a given cellular constituent in each of the 5,539 training microarray datasets. An average for the abundance of a given cellular constituent was simply computed based upon those training microarray datasets in which there was an abundance value for the given cellular constituent.

Step 314.

In step 314, a determination was made as to whether a previous instance of the candidate standardization data structure 64 has been computed. The first time steps 306 through 312 were performed (i.e., the first instance of steps 306 through 312), condition 314 was 314—No and process control shifted to step 318 because a previous instance of the candidate standardization data structure 64 had not been computed. When the second and later times steps 306 through 312 were performed, condition 314 was 314—Yes and process control shifted to step 316 because a previous instance of the candidate standardization data structure 64 had been computed.

Steps 318-322.

In steps 318 through 322, each of the cellular constituent values in the 5,539 training microarray datasets was transformed using a kernel transformation based upon the candidate standardization data structure 64 computed in the previous instance of steps 306-312 (e.g., the last time steps 306-312 were run). The kernel transformation transforms a cellular constituent abundance value x in the training microarray dataset to the cellular constituent abundance value y by the formula:

$$y = \frac{\sum_{j=0}^{m-1} w_j \cdot (t_j + s \cdot (x - h_j))}{\sum_{j=0}^{m-1} w_j}$$

where j is an index to a set of values M of cardinality m of cellular constituent abundance values in the candidate standardization data structure having values within a threshold value w of x;

$t_j$ is a value of an average cellular constituent abundance value, for a cellular constituent j, in the set of values M that is stored in the candidate standardization data structure 64;

$h_j$ is a cellular constituent abundance value for the cellular constituent j in the training microarray dataset selected in step 318;

$$w_j \text{ is } 1 - \left|\frac{x - h_j}{w}\right|^p;$$

w is the kernel function half-width which equals 1.5 in this example;

p is the kernel function parameter which equals 1 in this example; and $$s = \frac{t_{max} - t_{min}}{x_{max} - x_{min}}$$

$t_{max}$=the median value of the upper 10% quantile of the 250 cellular constituent abundance values in the candidate standardization data structure;

$t_{min}$=the median value of the lowest 10% quantile of the 250 of cellular constituent abundance values in the candidate standardization data structure;

$x_{max}$=the median value of the cellular constituents in the training microarray dataset selected in step 318 that are the same as the cellular constituents that form the upper 10% quantile of the 250 cellular constituent abundance values in the candidate standardization data structure; and $x_{min}$=the median value of the cellular constituents in the training microarray dataset selected in step 318 that are the same as the cellular constituents that form the lowest 10%) quantile of the 250 cellular constituent abundance values in the candidate standardization data structure. This kernel transformation was performed for each cellular constituent in the microarray datasets selected in the last instance of step 318. In step 322, a determination was made as to whether each of the 5,539 training microarray datasets had been normalized. If not (322—No), control passed to step 318 where an additional microarray was selected. If so, (322—Yes), control passed to step 306 and loop 306-316 was repeated until the percent similarity between the cellular constituents in the new candidate data structure and the previous candidate data structure were the same.

Housekeeping cellular constituents were removed from an input chip in the following manner:

1) for each i=0, . . . , N−1, where N is the number of housekeeping genes in the standardization data structure 64, compute $y_i$ using the formula given above excluding $h_i$ itself from the input set H of housekeeping genes in the target microarray dataset to be standardized;

2) compute standard deviation a of values $y_i$−$t_i$ (where $t_j$ is the standardization data structure value corresponding to $y_j$), where $y_i$ is the formula given above in conjunction with step 320; and 3) remove all cellular constituents $h_i$ from H for which σ exceeds 2.

Steps 322-330.

Once the percent similarity between the identity of the cellular constituents in the new candidate standardization structure and the candidate standardization structure from a previous iteration of loop 306-316 was greater than eighty percent (316—Yes) a candidate standardization data structure with 250 candidate housekeeping genes was outputted as the final standardization data structure 64. The final standardization data structure 64 included the identity of the 250 candidate housekeeping genes, and for each of the 250 candidate housekeeping genes, the average value of the housekeeping gene across the 5,539 training microarray datasets.

The expression patterns of the genes in the final standardization data structure 64 were visually inspected for residual tissue- or study-specific expression aberrations. Those exhibiting such aberrations, from a visual perspective, were removed from the final list. This resulted in a standardization data structure with 121 housekeeping genes listed in Table 1. FIG. 5 compares the standard deviations of the housekeeping genes with those of the non-housing keeping genes.

The standardization data structure developed in this example can be applied to the cellular constituent abundance data of each new specimen using the kernel described above to transform the raw data from each such specimen into a standardized set of cellular constituent abundance values. Thus, the standardization transforms raw expression values in a way that reduces the obscuring variation, and does not impact the predictive power of marker genes. Thus, the method compensates for run-to-run and processing variations in a way that is advantageous for the use of microarrays, such as the Affymetrix U133A, in clinical diagnostics.

Example 2

Comparing the Performance of the Standardization Data Structure of Example 1 to Other Standardization Methods To assess the performance of the standardization method outlined in Example 1 and described above in conjunction with FIG. 3 above, the performance of the standardization of Example 1 was compared with the rank order method described above in conjunction with FIG. 2, as well as the Affymetrix scaling method. The Affymetrix scaling method is described in Bolstad et al., 2005, *Bioinformatics and Computational Biology Solutions Using R and Bioconductor*, Gentleman et al. eds., pp. 13-32, Springer, N.Y., which is hereby incorporated by reference herein in its entirety. The standardization method of example 1 and the rank order method outlined in FIG. 2 utilize a reference array to adjust intensity levels of microarrays processed under different conditions.

To evaluate performance of the standardization methods two measures were considered: (i) assessment of reproducibility, and (ii) comparison of model prediction accuracy. The reproducibility refers to comparison of normalized expression values of biological replicates across three labs. Model prediction consists in building a tissue of origin test model using a learning dataset, and evaluating the predictive accuracy of the model on a clinical validation dataset.

The reproducibility assessment utilized a set of 56 biological replicates processed in three labs. Each of the tumor specimens was sliced in three sections that were subsequently processed in three labs, named LAB1, LAB2 and LAB3, to obtain 56 microarray expression profiles for each lab. Reproducibility analysis of the expression profiles applied the following steps to the raw expression values:

(i) Apply the relevant normalization to the raw values in each reproducibility array. For the standardization in accordance with FIG. 2 and the standardization of Example 1 (FIG. 3), this means applying the array normalization as described above in conjunction with step 304 of Example 1. For Affymetrix scaling, the normalization was applied by choosing the default Affymetrix scaling parameters in the GCOS software;

(ii) Extract the 1668 probes utilized in the tissue or origin test from the normalized arrays. This step generates three sets of 56 arrays with 1668 expression values each (one set for each lab); and (iii) Compute Pearson correlation coefficient between normalized expression values in each pair of labs.

The results of this analysis are shown in Table 3. The results clearly show that highly reproducible expression values were produced by the standardization method of Example 1 and the rank order illustrated in FIG. 2, whereas the expression values computed by Affymetrix scaling lacked sufficient reproducibility for clinical applications.

TABLE 3

Reproducibility assessment of standardization algorithms. The values shown are Pearson correlation coefficients of normalized expression values between different labs, produced using the three standardization algorithms.

| Algorithm | Labs | Pearson Correlation Coefficient |
|---|---|---|
| Example 1 standardization/FIG. 3 | LAB1, LAB2 | 0.87 |
| Example 1 standardization/FIG. 3 | LAB1, LAB3 | 0.88 |
| Example 1 standardization/FIG. 3 | LAB2, LAB3 | 0.90 |
| Affymetrix scaling | LAB1, LAB2 | 0.70 |
| Affymetrix scaling | LAB1, LAB3 | 0.46 |
| Affymetrix scaling | LAB2, LAB3 | 0.59 |
| rank order/FIG. 2 | LAB1, LAB2 | 0.88 |
| rank order/FIG. 2 | LAB1, LAB3 | 0.89 |
| rank order/FIG. 2 | LAB2, LAB3 | 0.91 |

Based on the results of reproducibility analysis summarized in Table 3, the Affymetrix scaling was eliminated from further consideration, and model performance was applied to standardization method of Example 1/FIG. 3 and the rank order method of FIG. 2. The analysis consisted of the following steps:

(i) apply the relevant normalization to the raw expression values in the training dataset (2039 specimens) and clinical validation dataset (502 specimens);

(ii) build an optimal tissue of origin model using the training dataset and the normalized values. As a side-effect, this step generates a 10-fold cross-validation error estimate of the optimal model;

(iii) apply the optimal model to the normalized values in the clinical validation dataset and report error rate.

The results of this analysis are shown in Table 4.

TABLE 4

Model performance assessment of standardization algorithms. The values shown are 10-fold cross-validation error rate of the optimal model on the training dataset, and error rate of the optimal model applied to the clinical validation dataset. All values are given as percentiles.

| Algorithm | Training dataset | Clinical validation dataset |
|---|---|---|
| Example 1 standardization/FIG. 3 | 5.2 | 9.6 |
| rank order/FIG. 2 | 5.2 | 10.4 |

Table 4 shows that the standardization method of example 1 produces the same error on the training set as the rank order method of FIG. 2 and has improved error on the clinical validation dataset.

7 REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8 MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A method for standardizing a test microarray dataset from a test microarray experiment comprising:
   a) obtaining the test microarray dataset from the test microarray experiment, wherein the test microarray dataset comprises a first plurality of cellular constituents ($P_1$) and wherein each of the first plurality of cellular constituents is associated with an abundance value ($x_j$);
   b) providing a standardization data structure comprising (i) a plurality of values of central tendency associated with a second plurality of cellular constituents ($P_2$) and (ii) an identifier associated with each of said second plurality of cellular constituents, each respective cellular constituent in $P_2$ being selected on the basis of having a low measure of cellular constituent abundance variability across a plurality of training micro array datasets relative to the cellular constituent abundance variability of other cellular constituents in a respective corresponding abundance bin in a plurality of abundance bins associated with the plurality of training microarray datasets; and
   c) applying the standardization data structure to the first plurality of cellular constituents ($P_1$) in the test microarray dataset using a mathematical transformation, the mathematical transformation comprising applying a smoothing regression which comprises transforming abundance value $x_j$ associated with the test microarray dataset into abundance value $y_j$ by (i) identifying a subset of cellular constituents in $P_1$ that have abundance values within a threshold value w of $x_j$, (ii) selecting, by their respective identifiers, a subset of cellular constituents in $P_2$ that correspond to the subset of cellular constituents in $P_1$, and (iii) smoothing, by way of smoothing regression, the values of central tendency of the subset of cellular constituents in $P_2$, thereby providing a standardized test microarray dataset, and wherein the above steps a) through c) are performed on a suitably programmed computer.

2. The method of claim 1, wherein each training microarray dataset in the plurality of training microarray datasets is for a different specimen in a plurality of specimens.

3. The method of claim 1, wherein a cellular constituent in said first plurality of cellular constituents or said second plurality of cellular constituents is a gene, a protein, a peptide, a proteoglycan, a glycoprotein, a lipoprotein, a carbohydrate, a lipid, an mRNA, a cDNA, an oligonucleotide, a microRNA, a tRNA, or a protein with a selected modification.

4. The method of claim 1, wherein the test microarray dataset or a training microarray dataset is measured from an expression microarray, a comparative genomic hybridization microarray, an exon microarray, or a microRNA microarray.

5. The method of claim 1, wherein a value of central tendency in said plurality of values of central tendency is a geometric mean, an arithmetic mean, median or mode.

6. The method of claim 1, wherein said mathematical transformation is a kernel transformation, and wherein the method further comprises, prior to said providing b), selecting said second plurality of cellular constituents ($P_2$) by:
   (i) standardizing each respective training microarray dataset in the plurality of training microarray datasets by dividing each cellular constituent abundance value in the respective training microarray dataset by a measure of central tendency for all of the cellular constituent abundance values in the respective training microarray dataset;
   (ii) dividing the respective cellular constituents present in one or more of the plurality of training microarray datasets into the plurality of abundance bins based on the central tendencies of the measured abundance values for the respective cellular constituents in the plurality of training microarray datasets, wherein each abundance bin represents an abundance value range exhibited by cellular constituents in the plurality of training microarray datasets;
   (iii) computing a measure of cellular constituent abundance variability for each respective cellular constituent in each abundance bin in plurality of abundance bins across the plurality of training microarray datasets;
   (iv) designating, for each respective abundance bin in the plurality of abundance bins, a predetermined number of cellular constituents in the respective abundance bin having the low measure of cellular constituent abundance variability as part of a candidate standardization data structure;
   (v) calculating a training value for each respective cellular constituent in the candidate standardization data structure as a measure of central tendency of an abundance of the respective cellular constituent across the plurality of training microarray datasets;
   (vi) transforming each cellular constituent abundance value in a training microarray dataset in the plurality of training microarray datasets using a kernel transformation based upon the candidate standardization data structure;
   (vii) repeating the transforming of step (vi) until cellular constituent abundance values in each training microarray dataset in the plurality of training microarray datasets have been transformed; and
   (viii) repeating steps (ii) through (vii), using the transformed values produced by an instance of step (vi) and the repetition of step (vi) as set forth in step (vii), each time determining the percent similarity between the identity of the cellular constituents in the candidate standardization data structure and the identity of the cellular constituents in a previous instance of the candidate standardization data structure, until said percent similarity is above a threshold value, wherein the cellular constituents in the candidate standardization data structure at a time when the percent similarity between the identity of the cellular constituents in the candidate standardization data structure and the identity of the cellular constituents in a previous instance of the candidate standardization data structure is above a threshold value are thereby selected to be said second plurality of cellular constituents; wherein said steps (i)-(viii) are performed on a suitably programmed computer.

7. The method of claim 6, wherein the measure of cellular constituent abundance variability computed for each respective cellular constituent in step (iii) is based upon a coefficient of variation of cellular constituent abundance value of the respective cellular constituent across the plurality of training microarray datasets.

8. The method of claim 6, wherein the kernel transformation transforms a cellular constituent abundance value x in the respective training microarray dataset to the cellular constituent abundance value y by the formula:

$$y = \frac{\sum_{j=0}^{m-1} w_j \cdot (t_j + s \cdot (x - h_j))}{\sum_{j=0}^{m-1} w_j}$$

wherein
   j is an index to a set of values M of cardinality m of central tendency in the standardization data structure having values within a threshold value w of x;

$t_j$ is a cellular constituent abundance value of central tendency, for a cellular constituent j, in the set of values M that is stored in the standardization data structure;

$h_j$ is a cellular constituent abundance value for the cellular constituent j in the training microarray dataset;

$$w_j \text{ is } 1 - \left| \frac{x - h_j}{w} \right|^p ;$$

w is the kernel function half-width;
p is the kernel function parameter; and
s is an average slope of the kernel function.

9. The method of claim 8, wherein $$s = \frac{t_{max} - t_{min}}{x_{max} - x_{min}},$$

wherein
$t_{max}$=the median value of a highest portion of said plurality of values of central tendency;
$t_{min}$=the median value of a lowest portion of said plurality of values of central tendency;
$x_{max}$=the median value of the cellular constituents in the training microarray dataset that are the same as the cellular constituents that form the highest portion of said plurality of values of central tendency;
$x_{min}$=the median value of the cellular constituents in the training microarray dataset that are the same as the cellular constituents that form the lowest portion of said plurality of values of central tendency.

10. A system for standardizing a test microarray dataset from a test microarray experiment comprising a processor and a non-transitory computer-readable storage medium encoded with computer-executable instructions that, as a result of being executed by the processor, control the system to perform a method comprising:
a) obtaining the test microarray dataset from the test microarray experiment, wherein the test microarray dataset comprises a first plurality of cellular constituents ($P_1$) and wherein each of the first plurality of cellular constituents is associated with an abundance value ($x_j$);
b) providing a standardization data structure comprising (i) a plurality of values of central tendency associated with a second plurality of cellular constituents ($P_2$) and (ii) an identifier associated with each of said second plurality of cellular constituents, each respective cellular constituent in $P_2$ being selected on the basis of having a low measure of cellular constituent abundance variability across a plurality of training microarray datasets relative to the cellular constituent abundance variability of other cellular constituents in a respective corresponding abundance bin in a plurality of abundance bins associated with the plurality of training microarray datasets; and
c) applying the standardization data structure to the first plurality of cellular constituents ($P_1$) in the test microarray dataset using a mathematical transformation, the mathematical transformation comprising applying a smoothing regression which comprises transforming abundance value $x_j$ associated with the test microarray dataset into abundance value $y_j$ by (i) identifying a subset of cellular constituents in $P_1$ that have abundance values within a threshold value w of $x_j$, (ii) selecting, by their respective identifiers, a subset of cellular constituents in $P_2$ that correspond to the subset of cellular constituents in $P_1$, and (iii) smoothing, by way of smoothing regression, the values of central tendency of the subset of cellular constituents in $P_2$, thereby providing a standardized test microarray dataset.

11. The method of claim 1, wherein the smoothing regression is a kernel transformation.

12. The method of claim 11 wherein the kernel transformation transforms a cellular constituent abundance value x in the test microarray dataset to the cellular constituent abundance value y by the formula:

$$y = \frac{\sum_{j=0}^{m-1} w_j \cdot (t_j + s \cdot (x - h_j))}{\sum_{j=0}^{m-1} w_j}$$

wherein
j is an index to a set of values M of cardinality m of central tendency in the standardization data structure having values within a threshold value w of x;
$t_j$ is a cellular constituent abundance value of central tendency, for a cellular constituent j, in the set of values M that is stored in the standardization data structure;
$h_j$ is a cellular constituent abundance value for the cellular constituent j in the training microarray dataset;

$$w_j \text{ is } 1 - \left| \frac{x - h_j}{w} \right|^p ;$$

w is the kernel function half-width;
p is the kernel function parameter; and
s is an average slope of the kernel function.

13. The method of claim 12, wherein $$s = \frac{t_{max} - t_{min}}{x_{max} - x_{min}},$$

wherein
$t_{max}$=the median value of a highest portion of said plurality of values of central tendency;
$t_{min}$=the median value of a lowest portion of said plurality of values of central tendency;
$x_{max}$=the median value of the cellular constituents in the test microarray dataset that are the same as the cellular constituents that form the highest portion of said plurality of values of central tendency; and
$x_{min}$=the median value of the cellular constituents in the test microarray dataset that are the same as the cellular constituents that form the lowest portion of said plurality of values of central tendency.

14. The method of claim 1, wherein the smoothing regression is a kernel transformation, wherein the test microarray dataset is not included in the plurality of training microarray datasets; wherein the first plurality of cellular constituents and the second plurality of cellular constituents are mRNAs; wherein the abundance value $x_j$ is a quantification of an amount of mRNA; wherein the first plurality of cellular constituents is more than 100 mRNAs; wherein the low measure of cellular constituent abundance variability is a standard deviation; wherein there are at least 100 values of central tendency in the standardization data structure, one for each of at least 100 different cellular constituents; and wherein the second plurality of cellular constituents comprises a subset of the first plurality of cellular constituents.

* * * * *